United States Patent
Crooke et al.

(10) Patent No.: US 10,619,157 B2
(45) Date of Patent: *Apr. 14, 2020

(54) CANCER TREATMENT

(71) Applicant: Ionis Pharmaceuticals, Inc., Carlsbad, CA (US)

(72) Inventors: Stanley T. Crooke, Carlsbad, CA (US); Mason Yamashita, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/822,692

(22) Filed: Nov. 27, 2017

(65) Prior Publication Data

US 2018/0346907 A1    Dec. 6, 2018

Related U.S. Application Data

(63) Continuation of application No. 15/356,947, filed on Nov. 21, 2016, now Pat. No. 9,873,876, which is a continuation of application No. 14/439,363, filed as application No. PCT/US2013/067469 on Oct. 30, 2013, now Pat. No. 9,540,641.

(60) Provisional application No. 61/720,939, filed on Oct. 31, 2012, provisional application No. 61/777,875, filed on Mar. 12, 2013.

(51) Int. Cl.
| | | |
|---|---|---|
| *C07H 21/04* | (2006.01) | |
| *C12N 15/113* | (2010.01) | |
| *A61K 31/7125* | (2006.01) | |
| *A61K 31/712* | (2006.01) | |
| *A61K 31/7115* | (2006.01) | |
| *C07K 14/47* | (2006.01) | |

(52) U.S. Cl.
CPC .......... *C12N 15/113* (2013.01); *A61K 31/712* (2013.01); *A61K 31/7115* (2013.01); *A61K 31/7125* (2013.01); *C07K 14/4718* (2013.01); *C12N 2310/11* (2013.01); *C12N 2310/111* (2013.01); *C12N 2310/315* (2013.01); *C12N 2310/3231* (2013.01); *C12N 2310/3233* (2013.01); *C12N 2310/3341* (2013.01); *C12N 2310/341* (2013.01); *C12N 2310/346* (2013.01); *C12N 2320/35* (2013.01)

(58) Field of Classification Search
CPC .................................................. C12N 15/111
See application file for complete search history.

(56) References Cited

U.S. PATENT DOCUMENTS

| | | |
|---|---|---|
| 6,784,290 B1 | 8/2004 | Monia et al. |
| 7,611,839 B2 | 3/2009 | Twine et al. |
| 8,816,056 B2 | 8/2014 | Swayze et al. |
| 9,359,608 B2 | 6/2016 | Swayze et al. |
| 2007/0213288 A1 | 9/2007 | Haura et al. |
| 2010/0298409 A1 | 11/2010 | Xie et al. |
| 2011/0054003 A1 | 3/2011 | Karras |
| 2012/0065125 A1 | 3/2012 | Yu et al. |
| 2012/0202874 A1 | 9/2012 | Karras |
| 2016/0002625 A1 | 1/2016 | Crooke et al. |

FOREIGN PATENT DOCUMENTS

| | | |
|---|---|---|
| WO | 2000/061602 A1 | 10/2000 |
| WO | 2005/083124 A1 | 9/2005 |
| WO | 2008/109494 A1 | 12/2008 |
| WO | 2012/135736 A2 | 4/2012 |

OTHER PUBLICATIONS

Blakey; AZD9150, A Next Generation Antisense Oligonucleotide Targeting Stat 3, Preclinical and Early Clinical Experience, SMI Conference on RNA Therapeutics, London Jun. 5-6, 2013.
Blakey; Advances in novel technologies to tackle intractable intracellular targets, Next generation antisense oligonucleotides (ASOs), 13th Tumour Microenvironment Workshop, Miami, May 2-4, 2013.
Callies et al., 'Integrated Analysis of Preclinical Data to Support the Design of the First in Man Study of LY2181308, A Second Generation Antisense Oligonucleotide', British Journal of Clinical Pharmacology (2011); vol. 71; No. 3; 416-428.
Chiarle et al., 'Stat3 is Required for ALK-mediated Lymphomagenesis and Provides a Possible Therapeutic Target', Nature Medicine (2005); vol. 11; No. 6; 623-629.
Darnell et al; Jak-STAT Pathways and Transcriptional Activation in Response to IFNs and Other Extracellular Signaling Proteins, Science, New Series, vol. 264, No. 5164 (Jun. 3, 1994), pp. 1415-1421.
Ding et al., 'Constitutively Activated STAT3 Promotes Cell Proliferation and Survival in the Activated B-cell Subtype of Diffuse Large B-cell Lymphomas', Blood Journal (2008); vol. 111; No. 3; 1515-1523.
Extended European Search Report for European Patent Application No. 13850047.5; dated May 30, 2016 (comprises supplementary European search report and European search opinion).
Fukada et al; Two signals are necessary for cell proliferation induced by a cytokine receptor gp130: involvement of STAT3 in Anti-Apoptosis; Immunity, vol. 5, Nov. 1996, pp 449-460
Geary et al., 'Pharmacokinetics of a Tumor Necrosis Factor-α Phosphorothioate 2'-O-(2-methoxyethyl) Modified Antisense Oligonucleotide: Comparison Across Species', Drug Metabolism & Disposition (2003); vol. 31; No. 11; 1419-1428.
Gough et al; Mitochonridal Stat3 supports Ras-dependent Oncogenic Transformation; Science. Jun. 26, 2009; 324(5935): pp. 1713-1716.

(Continued)

*Primary Examiner* — Kimberly Chong

(57) ABSTRACT

In certain embodiments, methods, compounds, and compositions for treating B-cell lymphoma or hepatocellular carcinoma by inhibiting expression of STAT3 mRNA or protein in an animal are provided herein. Such methods, compounds, and compositions are useful to treat, prevent, or ameliorate B-cell lymphoma or hepatocellular carcinoma.

32 Claims, No Drawings

Specification includes a Sequence Listing.

(56) References Cited

OTHER PUBLICATIONS

Hong et al., 'AZD9150, A Next-generation Antisense Oligonucleotide Inhibitor of STAT3 with Early Evidence of Clinical Activity in Lymphoma and Lung Cancer', Science Translational Medicine (2005); vol. 7; Issue 314; 1-12.
Hong et al; A Phase 1 Dose Escalation, Pharmacokinetic and Pharmacodynamic Evaluation of eLF-4E Antisense Oligonucleotide LY2275796 in patients with advanced cancer; Clin Cancer Res, 17(20), Oct. 15, 2011, pp. 6582-6591.
International Search Report dated Feb. 26, 2014 and Written Opinion dated Feb. 26, 2014 for PCT/US2013/067469 (12 pages).
Jain et al; Repression of Stat3 Activity by activation of mitogen-activated protein kinase (MAPK), Oncogene, 1998, 17, pp. 3157-3167.
Li et al., 'Inhibition of Growth and Metastasis of Human Hepatocellular Carcinoma by Antisense Oligonucleotide Targeting Signal Transducer and Activator of Transcription 3', Clinical Cancer Research (2006); vol. 12; No. 23; 7140-7148.
Monia; Development of anti-sense drugs for cancer, 8th Annual OTS Meeting, Oct. 31, 2012.
Scuto, et al.,"STAT3 inhibition is a therapeutic strategy for ABC-like diffuse large B-cell lymphoma", Cancer Res., May 1, 2011;71(9):3182-8.

Su et al., 'Advances in Understanding the Role of STAT3 in the Pathogenesis of Hepatocellular Carcinoma', World Chinese Journal of Digestology (2010); vol. 18; No. 21; 2240-2246 (English Abstract only).
Woessner et al; AZD9150, a new generation antisense molecule targeting STAT3, with potent pre-clinical pharmacodynamic and tumour growth inhibition activity, and early signs of clinical activity in large B-cell lymphoma, 2nd FEBS Special Meeting on JAK-STAT Signalling: Model Organisms and Beyond, Sep. 12-15, 2013 in Nottingham UK.
Yang et al; STAT3 complements defects in an interferon-resistant cell line: Evidence for an essential role for STAT3 in interferon signaling and biological activities; Proc Natl Acad Sci, USA, Cell Biology, vol. 95, May 1998, pp. 5568-5572.
Yu et al., 'Cross-Species Pharmacokinetic Comparison from Mouse to Man of a Second-generation Antisense Oligonucleotide, ISIS 301012, Targeting Human Apolipoprotein B-100', Drug Metabolism & Disposition (2007); vol. 35; No. 3; 460-468.
Zhong et al; Stat3 and Stat4: Members of the family of signal transducers and activators of transcription, Prod Natl Acad Sci, USA, vol. 91, May 1994, Biochemistry, pp. 4806-4810.
Wu Zhuli et al., 'Expression of STAT3 in Diffuse Large B Cell Lymphoma and the Prognosis Significance', Essay Collection of the 11th Chinese Conference on Malignant Lymphoma, CACA (2009); p. 442.

SEQUENCE LISTING

```
<160> NUMBER OF SEQ ID NOS: 129

<210> SEQ ID NO 1
<211> LENGTH: 4978
<212> TYPE: DNA
<213> ORGANISM: Homo sapiens

<400> SEQUENCE: 1
ggtttccgga gctgcggcgg cgcagactgg gagggggagc cggggggttcc gacgtcgcag      60 ccgagggaac aagccccaac cggatcctgg acaggcaccc cggcttggcg ctgtctctcc     120
ccctcggctc ggagaggccc ttcggcctga gggagcctcg ccgcccgtcc ccggcacacg     180
cgcagccccg gcctctcggc ctctgccgga gaaacagttg ggaccactga ttttagcagg     240
atggcccaat ggaatcagct acagcagctt gacacacggt acctggagca gctccatcag     300
ctctacagtg acagcttccc aatggagctg cggcagtttc tggccccttg gattgagagt     360
caagattggg catatgcggc cagcaaagaa tcacatgcca ctttggtgtt tcataatctc     420
ctgggagaga ttgaccagca gtatagccgc ttcctgcaag agtcgaatgt tctctatcag     480
cacaatctac gaagaatcaa gcagtttctt cagagcaggg atcttgagaa gccaatggag     540
attgcccgga ttgtggcccg gtgcctgtgg gaagaatcac gccttctaca gactgcagcc     600
actgcggccc agcaagggg ccaggccaac cacccacag cagccgtggt gacggagaag     660
cagcagatgc tggagcagca ccttcaggat gtccggaaga gagtgcagga tctagaacag     720
aaaatgaaag tggtagagaa tctccaggat gactttgatt tcaactataa aacccctcaag     780 agtcaaggag acatgcaaga tctgaatgga aacaaccagt cagtgaccag gcagaagatg     840
```

```
cagcagctgg aacagatgct cactgcgctg gaccagatgc ggagaagcat cgtgagtgag    900 ctggcgggc  ttttgtcagc gatggagtac gtgcagaaaa ctctcacgga cgaggagctg    960
gctgactgga agaggcggca acagattgcc tgcattggag gcccgcccaa catctgccta   1020
gatcggctag aaaactggat aacgtcatta gcagaatctc aacttcagac ccgtcaacaa   1080
attaagaaac tggaggagtt gcagcaaaaa gtttcctaca aggggaccc  cattgtacag   1140 caccggccga tgctgaggga gagaatcgtg gagctgttta gaaacttaat gaaaagtgcc   1200
tttgtggtgg agcggcagcc ctgcatgccc atgcatcctg accggcccct cgtcatcaag   1260
accggcgtcc agttcactac taaagtcagg ttgctggtca aattccctga gttgaattat   1320
cagcttaaaa ttaaagtgtg cattgacaaa gactctgggg acgttgcagc tctcagagga   1380
tcccggaaat ttaacattct gggcacaaac acaaaagtga tgaacatgga agaatccaac   1440
aacggcagcc tctctgcaga attcaaacac ttgaccctga gggagcagag atgtgggaat   1500
gggggccgag ccaattgtga tgcttccctg attgtgactg aggagctgca cctgatcacc   1560
tttgagaccg aggtgtatca ccaaggcctc aagattgacc tagagaccca ctccttgcca   1620
gttgtggtga tctccaacat ctgtcagatg ccaaatgcct gggcgtccat cctgtggtac   1680
aacatgctga ccaacaatcc caagaatgta aactttttta ccaagccccc aattggaacc   1740
tgggatcaag tggccgaggt cctgagctgg cagttctcct ccaccaccaa gcgaggactg   1800
agcatcgagc agctgactac actggcagag aaactcttgg gacctggtgt gaattattca   1860
gggtgtcaga tcacatgggc taaattttgc aaagaaaaca tggctggcaa gggcttctcc   1920
ttctgggtct ggctggacaa tatcattgac cttgtgaaaa agtacatcct ggcccttggg   1980
aacgaagggt acatcatggg ctttatcagt aaggagcggg agcgggccat cttgagcact   2040
aagcctccag gcaccttcct gctaagattc agtgaaagca gcaaagaagg aggcgtcact   2100
ttcacttggg tggagaagga catcagcggt aagacccaga tccagtccgt ggaaccatac   2160
acaaagcagc agctgaacaa catgtcattt gctgaaatca tcatgggcta taagatcatg   2220
gatgctacca atatcctggt gtctccactg gtctatctct atcctgacat tcccaaggag   2280
gaggcattcg gaaagtattg tcggccagag agccaggagc atcctgaagc tgacccaggt   2340
agcgctgccc cataccctgaa gaccaagttt atctgtgtga caccaacgac ctgcagcaat   2400
accattgacc tgccgatgtc cccccgcact ttagattcat tgatgcagtt tggaaataat   2460
ggtgaaggtg ctgaaccctc agcaggaggg cagtttgagt ccctcacctt tgacatggag   2520
ttgacctcgg agtgcgctac ctcccccatg tgaggagctg agaacggaag ctgcagaaag   2580
atacgactga ggcgcctacc tgcattctgc caccctcac  acagccaaac cccagatcat   2640
ctgaaactac taactttgtg gttccagatt ttttttaatc tcctacttct gctatctttg   2700
agcaatctgg gcacttttaa aaatagagaa atgagtgaat gtgggtgatc tgcttttatc   2760
taaatgcaaa taaggatgtg ttctctgaga cccatgatca ggggatgtgg cgggggtgg   2820 ctagagggag aaaaaggaaa tgtcttgtgt tgttttgttc cctgccctc  ctttctcagc   2880 agcttttgt  tattgttgtt gttgttctta gacaagtgcc tcctggtgcc tgcggcatcc   2940
ttctgcctgt ttctgtaagc aaatgccaca ggccacctat agctacatac tcctggcatt   3000 gcactttta  accttgctga catccaaata gaagatagga ctatctaagc cctaggtttc   3060 ttttttaaatt aagaaataat aacaattaaa gggcaaaaaa cactgtatca gcatagcctt   3120 tctgtatta  agaaacttaa gcagccgggc atggtggctc acgcctgtaa tcccagcact   3180
ttgggaggcc gaggcggatc ataaggtcag gagatcaaga ccatcctggc taacacggtg   3240
```

| | | |
|---|---|---|
| aaacccgtc tctactaaaa gtacaaaaaa ttagctgggt gtggtggtgg gcgcctgtag | 3300 |
| tcccagctac tcgggaggct gaggcaggag aatcgcttga acctgagagg cggaggttgc | 3360 |
| agtgagccaa aattgcacca ctgcacactg cactccatcc tgggcgacag tctgagactc | 3420 |
| tgtctcaaaa aaaaaaaaaa aaaaagaaa cttcagttaa cagcctcctt ggtgctttaa | 3480 |
| gcattcagct tccttcaggc tggtaattta tataatccct gaaacgggct tcaggtcaaa | 3540 |
| cccttaagac atctgaagct gcaacctggc ctttggtgtt gaaataggaa ggtttaagga | 3600 |
| gaatctaagc attttagact ttttttttata aatagactta ttttcctttg taatgtattg | 3660 |
| gccttttagt gagtaaggct gggcagaggg tgcttacaac cttgactccc tttctccctg | 3720 |
| gacttgatct gctgtttcag aggctaggtt gtttctgtgg gtgccttatc agggctggga | 3780 |
| tacttctgat tctggcttcc ttcctgcccc accctcccga ccccagtccc cctgatcctg | 3840 |
| ctagaggcat gtctccttgc gtgtctaaag gtccctcatc ctgtttgttt taggaatcct | 3900 |
| ggtctcagga cctcatggaa gaagagggg agagagttac aggttggaca tgatgcacac | 3960 |
| tatggggccc cagcgacgtg tctggttgag ctcagggaat atggttctta gccagtttct | 4020 |
| tggtgatatc cagtggcact tgtaatgcg tcttcattca gttcatgcag gcaaaggct | 4080 |
| tactgataaa cttgagtctg ccctcgtatg agggtgtata cctggcctcc ctctgaggct | 4140 |
| ggtgactcct ccctgctggg gccccacagg tgaggcagaa cagctagagg gcctccccgc | 4200 |
| ctgcccgcct tggctggcta gctcgcctct cctgtgcgta tgggaacacc tagcacgtgc | 4260 |
| tggatgggct gcctctgact cagaggcatg gccggatttg gcaactcaaa accaccttgc | 4320 |
| ctcagctgat cagagtttct gtggaattct gtttgttaaa tcaaattagc tggtctctga | 4380 |
| attaaggggg agacgacctt ctctaagatg aacagggttc gccccagtcc tcctgcctgg | 4440 |
| agacagttga tgtgtcatgc agagctctta cttctccagc aacactcttc agtacataat | 4500 |
| aagcttaact gataaacaga atatttagaa aggtgagact tgggcttacc attgggttta | 4560 |
| aatcataggg acctagggcg agggttcagg gcttctctgg agcagatatt gtcaagttca | 4620 |
| tggccttagg tagcatgtat ctggtcttaa ctctgattgt agcaaaagtt ctgagaggag | 4680 |
| ctgagccctg ttgtggccca ttaaagaaca gggtcctcag gccctgcccg cttcctgtcc | 4740 |
| actgccccct ccccatcccc agcccagccg agggaatccc gtgggttgct tacctaccta | 4800 |
| taaggtggtt tataagctgc tgtcctggcc actgcattca aattccaatg tgtacttcat | 4860 |
| agtgtaaaaa tttatattat tgtgaggttt tttgtctttt ttttttttt ttttttttgg | 4920 |
| tatattgctg tatctacttt aacttccaga aataaacgtt atataggaac cgtaaaaaa | 4978 |

<210> SEQ ID NO 2
<211> LENGTH: 79001
<212> TYPE: DNA
<213> ORGANISM: Homo sapiens

<400> SEQUENCE: 2

| | | |
|---|---|---|
| ataaaaatta aaaccctga tagtatcagc acatacacag aaatcactcc attatgcaaa | 60 |
| gttcatcctc tattatgaaa ggcaaaatgt ctacatttcc tatcaaccac tggcttcaat | 120 |
| tcagtaaaac ttgcatacca agtaggcaag gtggaaaaga aaaaggcaga acatttcatg | 180 |
| tatttcaatt cagacgcata aaaatgtcaa gccctacacg ttatcagctt tcgtatacac | 240 |
| cgtcttctgc attcgcctgt acgggccaat gggctagctg gtcggcgttt gatgcttgaa | 300 |
| gtgatggaac ggagtacggg gttaaatcca ctaccctctc cccacgcact ctagtaatta | 360 |

```
ctctatttcc acgtcatgtt tccgggtgtg tgtgtccctg ctcacgcaga aactgaagtt      420
caaagcaggc ggagtcaccc atgttctttt tgttgtcccc agaacccaat tcaggagttg      480
ggtccccaga ggatctggag atacctgggg actatctaac tagctgattc ccgcgtggta      540
agaggctctc aacctcgcca ccacgtggtg ccaaggggccg ggaaaaggga gagcgggcag     600
gagggagctg tatcagggggc atttaaagtg ccttgacgtc acgcactgcc aggaactcag     660
ctgagttttc agcaggacat tccggtcatc ttccctccct cccccggggc ttctgtgccc      720
aagtcctcgg ctcttccctc gctgtggcgg agggaggagc accgaactgt cggaacagcc      780
agcacagggg cgtatcagtc tcctcttggc tccgcccttt ctcctagctg ctctcctcat      840
tggtcagtgg gcggggcttc ggctgtaccg cacacgcact gggacctctg ggtggccgaa      900
cgagctggcc tttcatgaat tatgcatgac ggcgtgcctc ggccaggctg gggctgggcg      960
aggattggct gaaggggctg taattcagcg gtttccggag ctgcggcggc gcagactggg     1020 aggggagcc gggggttccg acgtcgcagc cgagggaaca agccccaacc ggatcctgga      1080
caggcacccc ggcttggcgc tgtctctccc cctcggctcg gagaggccct tcggcctgag     1140
ggagcctcgc cgcccgtccc cggcacacgc gcagccccgg cctctcggcc tctgccggag     1200
aaacaggtga agggggtgca gggtggggcc gttggggagg cctggggacc cggggggctcc   1260 gcagcggcag ggggcctctg ggaccttggg gatgttgtga tggacgctgc agtggggccg     1320
ggagagatga agagacgcgg agggtcgccc tgagggaaga ctcttcggga tgacaggagc     1380
gggcctcgga agggactcgg ggcgctggag ggaagtttcg ttcttcggag aaacagaacg     1440
cgctcgaggg ggcaccgtgg ggcgagggcg cactcggttg cggcggcagg agtgagggac     1500
agtcccccga tttcctgctc cctgggggccc tggggacgtt ccggccaccg gagcgactgt     1560
cacgccgacg gggatcaccg gcgcgagtgg ggggtcggaa agcgcctcct ccccgcccgg    1620
tcggcggctc ccgctgagcc acttcctccg cttgccctgt tcccgctcct tcaggagaca     1680
gctgtgccct tttggaggca ggaataggtg tgtctgtcgc ctgcagcctt acgggctggc     1740
tggtcgtggg taggctttat tgcataagaa tcaagtttcc tgtagggaaa ttgacagacc     1800
ggtactcttt ctaaattccc tcgcatcttt ttctaggtta aattatgctc ccccacgtc      1860 cccgccttgt aaaaaagaga aaaaaagaca aaataaaatc cccatcaacc cgtcaagcca     1920
gctctagaga gagaaataaa cctcttgaca ttgtcctttt ccaaatacct ggtaaagtcg     1980
gccagaagat aaataattga gccattgcat ttactggatt gtggtgttgc ttaattgcat     2040
aggacggaat gaaccaattg agagtgggag ttttctgtct cagagccaag atcttgggta     2100
aatgcagagg agagggaaac aaagacaggc tggccttgaa aaaccatgt gtgcaaactt      2160 tacatgcatt tgggggggtgt ggttgcactg aagttaacaa gattcaaacc gtcgcccaag    2220
ttggtatttc catgtttggt acacatcact ctgtgccata tcaggtcgtt gttaagtgtg     2280
gtgacaaaat cagtggttag tcattttttt aattaaaaat gtgtatagtg tgtacctgct     2340
ggtcttactg tatgtgcaac taaaggttta catagtctgt gtatgggttg taaatttttg     2400
gctggctgtg ctgataaagc attgggcttg aataaagcaa agcagaaaat catctcaatc     2460
ttttatatgt ggatttagac tgtgttatga cttggttcag ccagttttct atcttatttt     2520
atattaaata tgtctgtgtt ctctgagtca gcacatttat ttccttatta catgttccag     2580
acaggagtgc tagcccagtt tttgttcagt ttgcacagtg ggatgggggaa acaagtctgg   2640 aatttaaaaa aaaatgtttt agaggttgga gccttgattt tagtctctat attagcacat     2700
ccatcacaaa gaaccattag taaattcatg aatctttgt tttttatgta gttcatttga      2760
```

```
gaagaataat cacttagaaa tatccacagt gccaggcatg gtggtgcaca cctctgatcc    2820
cagctaattg aaggctgagg tgggaggatt ccttgagtcc aggagttgag tctggtctgg    2880
gcaacatggt gagaggccag gaattgggtc tagagtctag tctaagcacc ataatgagaa    2940
cccatcttta agaagaaag aaaggaaagg aggaagaaag gaaagaaaaa gaaatacccca   3000 cagcacagtt atgaattaac ccacaaagga cttgtgaggt gggtagttca cataacaatt    3060
accctaatat cgtagataag aaaattgagg ccaaaggatc aagacacttg ccaacgcag    3120 cagagtgcca tagtggtgga atttgtgcct ccttctgtat attttgtgaa aagtatcagt    3180
gaaattcttt ttttttttt ttttgagtca gagtcttgct ctgttgccca ggctagagtg    3240
cagtggcgca atcttggctc actgcaacct ctgcctcctg ggttcaagcg attctcctgc    3300
ctcagcctcc caagtagctg ggactacagg cgtgcgccac cacgcccagc taattttgt    3360 attttagta gagaccgggg ttttaccata ttggccaggc tggtcttgaa ctcctgacct    3420
tgtgatttgc ccacctctat ctcccaaagt gctgggatta caggtgtgag ccaccgcgcc    3480
cagtaagtat cagtgaaatt ctaacatata tctgaacagt aaaataccac caataggctg    3540
aaagacttca tgggaggtaa atattcaata aacaggtgaa aaaagaaata caaatggagc    3600
ttgcttagat tattttcta attgctatgt ctaacttggg aagtgaggaa ctgttttgg      3660 tcagcataat ttaccatcag aatttagcta tttactaatg aaaagaaata ctaatctagg    3720
tttgttttag attaaggaca gtcatgacct aaatgtcatt taaaccagag tgcattgtgg    3780
cttgatcagt ggtcatttct gtctctagaa agttgcttta acttctctgc ctctacgtgt    3840
ctcttgacat tcagatatga ggtggggtag aggtggtgac caacttcca gacgcctgag     3900 tccaaacctt cttagcttat ggttttctta ggtgatgtgc aaatcaacaa atatatactt    3960
tttttttttt tttttgagt tggagttgca ctctatcacc caggctggag tgcagtggca    4020
tgatcgtggc tcactgcaac ctcctcctcc cgggttcaag tgattctcgc acctcagcct    4080
cctgagtagc tgggattaca ggtgcccgcc actacgcccg ctaatttttt gtattttag    4140 tagagataag gtttcactat attgaccagg ctggtctcaa actcctgacc tcaagagatc    4200
tgcccacctc agcctcccaa agtgctggga ttacaggcgt gaaccacctt gcctggccaa    4260
catatatata ccttttgcaa cttttgtcaga gttgctatga agaataagtt gtatcttgtt    4320
cacagaaatt gcagtctact gggggagctg ataaatgttt taaccatcca atgtaacatg    4380
ttgtcatcaa agagatggtg agactttaca cttgtgctaa caaggtagct gttctacata    4440
aaagaacata cagtacagat gtagaacttt tctgttatca tagaacgttc tattggacag    4500
tgctaggctg aatgctacag atcttcagag aaaggagagg ttatgaggcc tggagttgtc    4560
tagaaagtct ttttgccaaa gagggatttc aactgggtcc caataatgg gtggaatttg    4620 ataggtgtaa agaatttgcg gtggtttatg cctgtaatcc cagcactttg ggaggctgag    4680
gcaggaggat tgcttgagcc caggagtttg agaccagctt gggcaacgtg gtaaaactcc    4740 ctctcccta aaaataaaaa aaattagcca ggcctggtgg cgtggacctg tagtcccagc    4800
tactggtgag actaaggtgg gaggatcacc caagccccgg gggttaaggc tgcagtgagc    4860
cgtgatcccg ccaccgcact ccagcctggg tgacagagtg agaccctgtc tccaaaaaaa    4920
aaaaaaattc ctggtagccc ggtagactag gagggtaagt aggggagaag tgattactta    4980
caaaagacat tgaatacagg accaaggaat ttcagttctg ttcttttgta ggggaagctt    5040
ttaaaacttt cggggcgccg ggcgcggtgg ctcacgcctg taatcccagc actttgggag    5100
```

```
gcccagacgc gcggatcacg aggccaggag atcgagacca tcctggctaa cacggtgaaa    5160
ccccatctct actaaaaata caaaaaaaag tagccgggcg ttgtggcggg cgtctgtagt    5220
cccagctact cgggaggctg aggcaggaga agagcgtgaa ctcgggaggc ggagcttgca    5280
gtgagccgat atcgcaccac tgcactccag cctgggcgac agagcgagac tccgtctcaa    5340
aaaaaaaaaa aataaataaa taaataaata aataaaactt tggagccgaa gcactgatgt    5400
ttaatcatag agtgcttact atgtgttagg cacaggcctg attgcctgat gctggttaat    5460
ttgtacaaag taaatcagtg catatgccct ctgccctagg ggagttatta actggagtct    5520
gacattgtac aaaggtaggt atcctgacta gtttgatttg gtactttggg tgaaaaaagt    5580
atagtgtgct taagtgcaga agtgtttttt gaggattttt gattggatac aaaccaccac    5640
tcatatttta tgtctttggc acttaaaaat ttcaccataa cttttgagtc atttataaaa    5700
accactgaaa gagtacttga gggacatccc cgaatcctga agaacttctg gtgttctgga    5760
gcagcctcag tgagatccag gaggatggca ttgctgggct ggcccagccc ttattgatta    5820
tggtgtaaag aattaatatg gtggttatat actctttgtt agacaccttg gcttacaaga    5880
cgtaagcgta aagtgtagtg cgctttagtc agtatggcca catggtcctt tggtggtaaa    5940
ttgtttgaga tgcctccagt ttttaaaagg agtagcatat cgggccagga gcagtggctc    6000
atgcctataa tcccagcact ttggaaggcc gaggcaagag gattgcttga gcccaggagt    6060
tcaagaccag cctgggcaac atagtgagac cactttgttt ctttaaaaaa aaaaaaaagg    6120
caaaaacagg ctgggcatgg tggctgatgc ctgtaatccc agcgctttgt gaggcagagg    6180
tgagcggatc acttgaggtc aggagtttga gaccagcctg gccaacatgg taaaaccccg    6240
tctctactaa aaatacaaaa attagccagg tgtggtggca cacgcctgta gttccagcta    6300
ctctggaggc tgagccagga gaattgcttg aacctgggag gtggaggctg cagtgagcca    6360
agatcctgcc actgcactcc agactggggg acagagtgag acattctgac agtgctacac    6420
tgaatgctac atgtcttcag aggaaggaga ggttatgagg cctgggaata acatatggaa    6480
gaatgaattt ctgttatggt cagttctcat ttgtcatgtt aggattactg caactcttac    6540
ccagccgggt gtggtggctc atgcctgtaa ttccagcact ttgggaggct gtgggcggat    6600
cacgaggtca ggagatcgag accatcctgg ctaacacggt gaaactccgc tctactaaa    6660 aatacaaaaa attagcccag cgtggtggca gacgcctgta gtcccagcta ctcaggaggc    6720
tgaggcagga aatggcatg agtcctggag gcggagcttg cagtgagctg agatcgtgcc    6780
actgcactcc agcctgggca acagagtggg actccatctc aaaaaaaaaa gaaaaaaaaa    6840
aggattaccg caactctta attcagatca gcaaacatgt tgagagccag gtattgcgtc    6900
aggcaggatc caaggataat gaaatattgt ccgttttcat gaaactggag atgttgcagg    6960
gaccgaggtg tgtgctatgc cagtatggaa gtaggacagg ggagacgaca gggcagtgag    7020
tggttcaaga ctctggctct gaagtcaaac agatctggga ctgaatcctg gatctgccac    7080
ttcctagtca gaatctgagc ctctattttc ttatctgtaa aagaagatta taacagtgct    7140
tatcttgtag gtactgttga cgattcaata agataatgtg gataaaatgc ttagcatagt    7200
gcctggcaca tagtaagagc tcggtaaatc taagttctta ctaaatatcc aagaaaagag    7260
attaattctt ttcaggagtg agagaaagtc atcattattg aggggcttta tcagatggga    7320
acacctgaat agggtttat aggatgaata ggaattcttt ccacgaagtt gcgttacaaa    7380
aagttgcatt caaggctgaa ggaacatgag ggtgcagagg cttaaaacag ccttgtgtgt    7440
tcagggagct ataagtagaa gttcttaatt taggagaact aaaccaaggg gaaaggaggc    7500
```

```
caaggaacca cagttcttat ccctttctg ttaataattg ggtttaaatg tcattaaaat   7560
aagttatttt gtccttttta gaaaagtaat aacatgctat tataaaaaaa aagacttgta   7620
ggaatataaa atgtgtgttt tacatgtatc ctgttaattg acttgctttt attcagattt   7680
tttgcagccc tttctgttta ccaggttatc ttggagacat atttattcca aattcctttt   7740 ttttttttt tttgagatgg agtctcgctc tgtcgcccag gctggagtgc agtggcgcta   7800
tcttggctca ttgcaagctc cgcctccgg gttcacgcca ctctcctgcc tcagcctccc   7860
gagtagctgg gactacaggc gcccgccacc acgcccagct aatgttttt tttttatatt   7920 tttagtagcg acagggtttc accgtgttag ccaggatggt ctcaatctcc tcacattgtg   7980
atccgcctgc ctcggcctcc caaagtgctg ggattacagg cgtgagccag cacgcctggc   8040
cttccaaatt cctttaaca gcctagcaaa agaataataa ggaaggtaaa tctgcccta   8100 caagaaaata atgcttcgac gatccggctt tccttcctgc tacccccagc cataagaata   8160
aatgaccttg ctcatcactg aaattttacc tgacctttga attttaact gcgtcagcca   8220 aagaacttat attttgagta ttcctaaggt gattgctatt gtagttttga aacacttggt   8280
tggtatgttt gagggtttca tggtccaaag ttactatagc agttaaaaga gtggactatc   8340
aggtcagacc tattgggctt taatcccagt tctgccttct cttagacctt gggcctgttg   8400
ttttcacttc tctggttttc agtttctctg tccacaattg tggaaacgag gtccacttgt   8460
agagtaattg agaggatgaa gcaagatgat gcatatcaag tactttgcat agtgccgggc   8520
agacaggtaa cattcaagtg ctaataatta ctattattac tatttattt ttgagacagg   8580 ttctcactct gtcacctagg ctggagtgca gcggtgagat cacagctcat gacagccttg   8640
acctcctagg ctcaagtgat cctcctgcct cagccttcgg ggtagctggg ctacaggtg   8700 tgtgctacca ccctcagcta atttctaat ttttttgagt caggatctcg tcacgttgcc   8760
taggctgaat tactcttatt aaaaactata atatcaggcc gagtgcggtg gctcacgcct   8820
gtaatcccag cactttggga ggccaaggcg ggtggatcac ctgaggtcag gagttcaaga   8880
ccagcctgcc caacagagtg agacccccc cgtctctact aaaaatataa aaattagcca   8940
gttgtggtgg tgggcacctg taatcccagc tactcgggag gctgaggcag gataatcgct   9000
tgaaccgggg aggcggaggt tgcggtgaac cgagatcgtg ccactgcact acagcctggg   9060
tgacagagtg agactctgtc tcaaaaaaac cgaaaaacaa aaagcataat tagggtggta   9120
acgcttatac ataggggcag gtggaataaa acataattag gaggtcgggc atggtggctc   9180
acgcctgtaa ttccagcact tgggaggcc gaggcgggtc aggagttcaa gaccagcctg   9240
cccaacatag tgagaccccg tctctactaa aaatataaaa tttagcctgt gtggtggcg   9300 ggtgcctgta gtcccagcta cccgggaggc tgaggcagga gaattgcttt tgaacccagg   9360
aggtgggggt tgcagtgagc tgagatcgcg ccgctgcact ccagcctggg agacagagca   9420
agactccgtc acaaaaacaa aaaacaaaaa actgtcatat caaaaactaa actaaaatgg   9480
taatatctgt tagatattac aaagtcaggc aaattatgat tcatggcagc cactaatgac   9540
ccaaaggaga gaaagaataa ttagcagatt ctaacctaat gggaaaaaaa ctaaatgaat   9600
agggatgggg gacttacatt ctgttagagg aaattgaggc tgtcatataa aaggaatagg   9660
taaggcaaac tgtaaattcc tgtttacaca aatgcccttc tgataaatct ctgcattgcc   9720
cacagtccat gattacctct cccttattt aagtaatatt taacacatta aaaatggatt   9780
accacccaag gaattgctcc cgacccagaa agtgcaggta gtgttgaagg tttgagggga   9840
```

```
agaggaatga ttagagttgg ttgtgtctca ggaagaagcc aacaggagga accttatttt    9900
gagtcaggta aagaaggtgg gagtgaggag gcatcccggt ggccaggtat gaagctggga    9960
gctgattgct gcacattact cagctgaatt aaatgtgccc tcacatctgt gtgtgtgcgt   10020
acatgcaaat gtacatgtgt atgagttagt tggaggggta gacctttatt ttcctgtcct   10080
gtaactttcc tttgcaaact aatctgtatt cagaacagtg ttgcagttaa gaaccaccca   10140
gcttgtccat gaaacaggtt ctctcacccc atctccccag ttttagagaa ggcaggaaag   10200
aaaaggcagt gcttttcttt tttcctggcc gtatgcgggg caggaagaag ccagcagagc   10260
ttgaaagaga aagtaaacct tctgggaaat aaacggcttg gcttccctat tgtggaggag   10320
gagtgcaaat tattagggggg atgtttgggt agttttgta gaagccattt ctgaaaactg   10380
atttggatta gtgaaggtaa gcccaattta ggaaaaccct gcccagtctg gtgtcagcca   10440
cctgtttccc gctttgtttg attgatttga ttagtttgtg gtattctgac ctctcatttt   10500
tattacaaga gttggaagat ttgagtctga acttgagcac ctgcttcggt gaaagcttcc   10560
taaaatgcat gttttttcac attttttctc atgttcattt tgttttgctt tttagcaaac   10620 acttttctg acagaatcta aaagcattag acttttcttg ttttccccctt ctctccccac   10680 aatgtaatct tgaaaaccca aatgttagct gtgtaaatta cctctcccgt aaaccaaaca   10740
aagtgcaata ttgcattgag ttagcattga aatagtcggc cttttgaattt ttttctactt   10800 gtggtttaga cataataaat atttcatctc agactgactt tctcgacaaa tcagttttgc   10860
atttgggcct cttttcatca gtatgtttag ggaaagcaca tttattgaaa cattaaccaa   10920
aatgaaacat aattaggagg ccgggagcga tggctcacgc ctgtaatccc agcactttgg   10980
gagaccaagg catgtggatt gcttgaggtc aggagttcaa gaccatcctt gccgacttgg   11040
tgaaatcctg tttctactga aaatacaaaa aactagctgg gtgtggtgac gcgtgcctgt   11100
aatcccagct actctggagg ctaaagcaag agaatcgctt gaacctggga ggcagaggtt   11160
gcagtgagtc gagatcgtgc cactgcactc cagcctgggc aacagagact ccgtctcaaa   11220
caaccaaaaa aacaaaaaca agcataatta gggtggtaac gcttatacat aggggcaggt   11280
ggaataattg aagcattctg gagccagaaa taatcaactg attaagaata atctggctgg   11340
gtgcggtggc tcacgcctgt aatcccagct actcaggagg ctgaggcagg agaatcgctt   11400
gaacctggga ggtggaggtt gcagtgagcc gagatcgcgc cattgcactc cagcctgggc   11460
tatggagcaa gactccatct caaaaaaaa aaaaaaaaa atcctgtttc tgcagaaata   11520
tcccaggtgt cctgggtcag cagtgcccca tagattccac ggacgtttac cctaagtttt   11580
ccaatgggag ttcatacctc tatcccagt gagaatattt tctgagtaat gggaatgaga   11640
ttggagatgt agggtagaga agatccatac agtctttggg ttaaactttt tcctctttgc   11700
ctaggaaaga ttaatgctaa tcttaaccac agatttgtag taagaatgta tcagttttgt   11760
cattcagttc tagactccag ttttctttat tgtaatacca atattttaga gtaaattttg   11820
aaatgaatca gtacaaaaga tatgtagtaa gtggaaagtt agtccgcacc ttatccttgg   11880 gactcttttcc cagggacagc tagttaccta ctatttatct ctcctgagtt acttcatatg   11940
tatgcatgca aacatgttat tctctggggtg ttgttccttc catatatagc agcaaataca   12000
ccaaactctg tattttgctt tttgtcactt tatcttagag aatactcaat gcaaatacat   12060
gtgtatatac ctcatgttta aaaaatctac atagtaaaat tagccaggca tggtagtgtg   12120
tgcctgtaat cccagctact cgggaggctg tggtgggaga tcacttgaa ccctgagatc   12180 acaccactgg actccagcct gggccacaga gcaagattct gtctcaaaaa acaaaaacaa   12240
```

```
aaacaaaaaa actacagagt agtattctag gctatgcata tcataaattt gatttcctaa     12300
tgataggcat agatgatttg cctgggcggc aaattagcgt tggctgtgtc tcaggaagaa     12360
gccaacagga ggaaccttat tttgagtcag gttccaaaga cagaaacatt gtctgacatt     12420 tgttttggg cttatatgaa taaatctgta cacatatatt tttaatgttt taatcgtaat      12480
atgtatacta tttggaaatg tggcttttta gttaacagag tgcatgtttt accccattgc    12540
acttaaacat taacttgggg ataattaaat gagtctgtca cttggacagg caggaattgt    12600
accccccaca aacccataaa ccgccaattt ttttttttg agacagagcc tcattctgtt     12660
gcccaggctg gagtgcagtg gtgcgatctg gcccactgt aagctcagcc tcccgggttc     12720
atgccattct cctgcctcag cctcccaagt agctgggact acaggcgccc gtcacaatgc    12780
ccggctaatt ttttgtattt ttagtagagt cggggtttca ccatgttagc caggatggtc    12840
tctatctcct gaccttgtga tccgcccgct ttggcctccc aaagtgctgg aattacaggt    12900
gtgagccacc gcacctggcc ggttttttt tttttttttg agatggagtc ttgctctgtt     12960
gccaggctgg agtgcaatgg catgatctcc gctcactgca acctccacct cccgggttca    13020
agtgattctc ctgcctcagc ctcctgagta gctgggacta caggcgtgtg ccaccacgca    13080
cagctaattt ttgtaatttt agtagagatg gggtttcatt aataatcatt aatattagac    13140
aactgtcaga ctcacagtgg tggatacaaa ctttctcaaa ttctgatttt tactctaaag    13200
ctcaaatttt atcattggca acaaatattg tcagttgctt tccctgaaca dacagcttcc    13260
cttctttcat ttttgagaaa atatctgcca gtatcccagt tggtttatca atcattcttt    13320
ctcttttttt ttttgagacg gagtctcact ctgtcaccca ggctggagtg cagtggcatg    13380
atctcggctc actgcaacct ccacctccca ggttccagca attctcctgc ctcagcctcc    13440
cgagtagctg ggattacagg ggctagcagc cacacctggc taattttgc attttagta     13500 gagacagggt tttaccatgt tggccaggct gatcttgaac tcctgacctc atgatatgcc    13560
caccttggcc tcccaaagtg ctgggattac aggtgtgagc cattgcgccc ggctctatta    13620
tttcttttct ttcttctttt ttttttttt tttttgagat ggagtttcgc tcttgttgcc     13680
caggctggag tgcaatggcg cgatctcggc tcaccacaac ctccgcctcc cgaattcaag    13740
tgattctctt gcctaagcct cccgagtagc tgggattaca ggcatgtgcc accacccg     13800 tctagttttg tattttatt agagatgggg gtttctccat gttggtcagg ctggtctcga    13860
actcccaacc tcaggagatc tgcctgcctc agcctcccaa agtactggga ttacagtttt    13920
gagccacctg acccggtttg cttattattt cttttaaatt taaaaaataa taaataaagg    13980
ggccatgaga gcgaagagtt tgagaaaggt tggtctaaag gttttaacat aagaatccct    14040
gggttatttg cttaaaaaga agaaagaatc tatggatctg cctgagaggg tctgatgtag    14100
tttatctggg gtcatcctca caggcatagc agatattctg attcagatgg tccttggtcc    14160
ttagtttgag aaatgtggct ttacaaggcc catagaaat aaagtcttct ttggattagt     14220
gaagtcatgt ccacagggtt tagaaaatgt ttttgtttta gagataaagg taagtggaag    14280
agtagacatg tagtgaatga gggaaaatgt tttagagatt cttttttatt ctgtttactc    14340
ttcttggtat gcacgtacct gaatattaag gatattttat gaagtcatga cattaccaga    14400
ttaatgttgg ttttgtttta aggtactttc tgactgctgg ggttaattcc tacagacgat    14460
tctggtaaag aatagccttt aagttttaaa agtgttgact tatttcagat gtcttaataa    14520
agttaacttc cagttattac atgtaacgta tataaagctc tcattttcct ttattctcgt    14580
```

```
taattgtttg cataacaaat tcaaagggaa atttgcttgg cagagatcag atagcagaga    14640
tgagatttaa aaacaggtaa tttggctact agcctgggag tttgaagatt ccaagtttgc    14700
atccatgtgt agtcacttaa catttctgtc cttatctgta aatgggaata cacctactt    14760
gatagggttg ttacattatc ttggccacct caggttctct ttggctgagt gattgactgg    14820
aaaacgcaat gtgaattcat gcttcagact gggttctttt ttttttttt ttttgagatg    14880
gagtttcact cttattgccc aggctggagt gcaatggcac gatctcagct cactgcaacc    14940
tctgcctccc aggttcaagc gattctcctg cctcaggctc ccgagtagct gggattacag    15000
gcatgcacca ccatgcctgg ctaatttttt tgtatttta gtagagacgg ggtttcactg    15060
tgttggtcag actggtttca aactcctgac ctcaggtgat ccacctgctt cagtctccca    15120
aagtgctggg attacaggca tgagccaccg cacccagccc aggctaggtt ctatatgggt    15180
gtgcttttta gaatttagat catgggctat ccccaacaca aactggataa tgtttctttc    15240
tagattctct ctaagcgtgt attctctttc tttcctaggc acagccacca cttcacttac    15300
attgtgggat tataatttca tgagtagtgg aatttcctta accttctctt gtgtgggagc    15360
tgaaggacaa aatgagatat tctctgaaga gtggttacat catgcaaaac tatgatgtgt    15420
aatgaggtca cttagttttc taagtacatt atacattttg ataagatttt catagaaaag    15480
cttgtctcct tggggagatc actcatcttc catcttgact attatttaaa ctttatgggt    15540
cagatttatc ttttaaaaa cttaaccata aagctcaatt aatttttttt tttttttttt    15600
gagacggagt ctcgctctgt tgcccaggct ggagtgtagt ggcgcgatct cggctcactg    15660
caagctctgc ctcccaggtt catgccattc tcctgcctca gcctcctgac tagatgggac    15720
tacaggcgcc cgccacgatg cccggctaat ttttgtatt tttagtagag acggggtttc    15780
accgtgttag gatggtctcg atctcctgac ctcgtgatcc acccgcctcg gcctcccaaa    15840
gtgctgggat tacaagcgtg agccaccgcg cccggctcaa ttaatatatt ttaaaaatta    15900
atagacttta ttattttat tttattttat ttttgaggca gagtctcgct ctgtcaccca    15960
ggctgagtgc agtggtgtga tcttggctca ctgcaaactc cacctcccgg gctcaagtga    16020
ttctcctgcc tcagcctcct aagtagctag gattacaggt gcctgccacc atacccggct    16080
agttttgta attttagtag atacgtgttt tctttctttt cttttctttt ttttgagatg    16140
gagtttcact cttttgccc aggctggagt gcaatggcat gatctcggct cactgcaacc    16200
tccgcctccc aggttcaagt gattctcctg cctcagcctc ccaagtagct gagattatag    16260
ttgtctgcca ccacgcctgg ctaatttttt gtatgtttga tagagacagg gtttcactat    16320
gttagccagg atgtctcgat ctcttgacct cgtgatccgc ctgccttggc ctcccaaagt    16380
gctgggatta caggcgtgag ccactgcggc cagtctagac tttattttt aaagcagtgt    16440
tagttttaca gaaaaattat gtggaaagta cagagagttt ccatataccc cttactttct    16500
cccacaactt ctattattaa catcttgcat tagtatagta cgtcccttac aactaatgaa    16560
ccaactcgat acattattat taaccaaatt cctgagttta tttatttct attttattt    16620
tattattatt attttttaga ggtagggtct cactgtgttg tccaggccag gttgcagtgg    16680
catcatcata gcttgctata gcctgaaact cctgggctca agcaatcctc ctgcctcagt    16740
ctcccaaagt gttggaatta caggtgtgag ccactctgtc cagcctgaag tccatagttt    16800
acattacatt tcactctgtt gagcattcta tggattttga caaatgtgtg atgatgtata    16860
tttgccagta cacaattata taaaatagtt ttactgccct agaaacccc tgtgctccac    16920
ctattcattc ctctgctgaa ccactggcaa ccactgatct tttataatat ctccatagtt    16980
```

```
ttgtcttttc cagaatgtca tatagttgga catacagtgt gtagccttt cagattggct      17040
tctttcagta aatgatatgc atttcaggtt tcttcatgtt tttttgtggc ttgataggtt      17100
gtttcttttc attggtgagt aatactctat tgtatggata taccacatgt tgtttatcaa      17160
acattcacct gaaggataga catcttggtt gcttccaagt ttgagcagtt atgaataaag      17220
ctgctataaa cattccagtg caggactttt cacctcctct ggataaatat caaggagtgc      17280
aattgctaga tcatatggta agagtatgtt tagttttgta agaagctatc aaactatatt      17340
caaagtgact gtaccattat acattcccat cagcagtgag tgagagttcc tgttactcca      17400
catcttcacc agcatttagt ggtgtcagtg ttttggattt tagccatttt aatgggtgta      17460
taatggtata cctattaaaa ttggtttttt ttggagacag agtttcacag tttcactctt      17520
gttgccctgg ctggagtgca atggcgcaat ctcggctcac tgcagcctcc gcctcccagt      17580
ttcaagtgat tctcctgcct cagcctccca agtagctggg attacaggtg cacgccacca      17640
tgttctgcta atttttttgt attttagtag agatgggggtt tcactgtgtt acccaggctg      17700
gtcttgaact cctgagctca ggtaatccac ctgcctcagc ttcccaaagt gttaggatta      17760
caggcatgag ccaccgcacc tggcctcaat tttttttttt tttttttga cagagtttt      17820
tgctcctgtt gaccaggctg gagtgcagtg gcacaatctc ggctcactgc aacctccgcc      17880
tcctgagttc aagcgattct cctgccacag cctcctgagt agctgggatt ataggcgccc      17940
gccactacgc ctggctaatt tttttttttt ttttaattag acgaggtt tctccatgtt      18000
ggtcaggctg gtcttgaact ccccgttctc aggtgatccg cctgcctcag cctcccaaag      18060
tgctgagatt acaggtgtga gccaccgtgc ccgcctgtt ttggctttta ctgtgaagac      18120
gtgttagccg ctgtgatgac tagcaagtgt ggccctccac ccagtcgctc tgggctccca      18180
gctcctgcat cctgctgcaa acttgacatc ttccctcaag taacttgtag ttgtctcctg      18240
tctacttgcc caaatataa ctcttaaact tttctctctg caagtttgtg cctctctccc      18300
tgtctgactt ccccatctaa ataaatggta gaccaccatc tactccttg tgcaagccag      18360
aaatctagga atcatcctta aattcccgt tctgtcttat ctctgctttc attcaaagca      18420
tcagcaaatc ctgttggttc tacctctgaa gttttctcaa atactgttac ttgactcatc      18480
ctgacttttg tttctgcttt atgttaggct aaatgccctg aaaactcttt tgtacaaaac      18540
acctagaaat actggataaa ctgggcttaa cagggaggcc cggtgtggtg gctcacgcct      18600
gtaatcccag aactttggga ggccaaggtg ggtggatcac ctgaggtcag gagttccaga      18660
ccagcctggc caatacgtag tgaaacccca cctctactaa aaaaaaaaa aaaaattagc      18720
tgggtgttgt ggtgcacacc tgtaggtggt gcatgcttga acttgggagg cggaggttgc      18780
agcgagctga gatcgcgcca ctgcacttca gcctgggtga cagagcagga ttctgtctct      18840
taaaaaaaaa aacaaaaaaa gaaaacagg aaaatcttca gaagcaaaa ccaaacaatc      18900
tcaccaaaga aatgagaaga tggctgggcg cggtggctca cgcctgtaat cccagcactt      18960
tgggaggccg aggcgggcag atcacccgag atgggcagat caccgaggt caggaattcg      19020
agaccagcct ggccaatatg tgtgaaaccc gtctctgcta aaaatacaaa aattagccag      19080
gtgtggtggc aggcgcctgt aatcccagct actcaggagg ctgaggcagg agaatcgctt      19140
gaacctggga ggcggaggtt gcagtgagcc gagatcatgc cactgtactc tagcctggac      19200
gacagagcaa gactctgtct caaaaaaaaa aaaggctggg tgtggtggct catgcctata      19260
atcctagcac tttgggaggc caaggtgggc ggatcacttg aggccaggtg aacatggcga      19320
```

```
aaccccatct ctactaaaaa tactaaagtt agctgggcat ggtggtgggt gcctgtaatc   19380
ccagctactc gggaggcgag gcaggagaat cgcttgaacc aggaggtgga ggttacagtg   19440
aaccgagatc tcgccaccgc actctagtct gggcgacaga gcaagactcc gtctcaaaaa   19500
acaacaacaa aaaaccaaca catggccaaa gtgcagtgac ttacatctgt ataatcccaa   19560
tgttttggga ggctgaggca ggaggatcgc ttgagtccag gaatttgaga ccagcctggg   19620
caacatagac ctcatcacca aaaaaaaaat atttttaat tagctgggtt tggcagcatg    19680
tacctgtagt cctagctact caggaggctg aggtgggagg atcacttagg cccaggagtt   19740
tgatagttcg aggttatagt gagctatgat cctgccactg cactccagcc tgggccacag   19800
agtgagaccc tgtctcttag aaacaaaaca aaacaaaaaa aagaaactga attaaaaaca   19860
acaagaacaa aaatgctgct ttttgttatt gagttgtagc ccaagtttct tgagggtaaa   19920
gcattgaaaa gcaggcagta atagatttgc tgtttaaaga gatttacttg cagcactatt   19980
cacaatagca aagacatgga atcaacctaa atgcccatca gtgacaaatt ggataaagaa   20040
aatgtggtac atacactgtg gaatactatg cagccataaa aaacaacgag atcatgtttt   20100
tgtttgtttg tttgtttgtt tgttttgag atggagtctt gctctattgc ccaggctgga    20160
atgcaggtgg cacgatttca gctcactgca acctccgcct cccaggttca gcaattctc    20220 tgcctcagcc tcccgagtag ctgggattac aggtgccctc caccatgcct ggctaatttt   20280
tgtatttcta gtagagatgg ggtttcaccg tgttgggcag gctgttcttg aactcctgac   20340
ctcatgatcc tcccacctcg gcctcccaaa gtgccgggat tacgtgtgag ccaccgtgct   20400
cggctgagat catgttttg caggaacatg gatggagctg gaggctatta tccttagcaa    20460
agtaatgcag gaacagaaaa ccgaagacca cgtgttctca cttataagtg ggagctaaat   20520
gataaggact tgtgaacaca agaaggaaa ccacagatac tggggtttac ttgagggtgg    20580
agagtgggag gagggagagg aacagaaaag ataactattg ggtattgggc ttaatactta   20640
atattttatc aaaataagct gtacaacaaa cccctctgac atgagtttac ctatataaca   20700
aacttgcacg tgtaaccccca aacctaaaat aaaagttaaa aaaaaaaaaa aaggctggtt  20760
gcattgggag gctgaggcag gcagagcact tgaggccagg aattcgagac cagcttggct   20820
aacgtggaga aaccctgtct ctactaaaaa ttcaaaaatt agccaggtgt ggtggtgcat   20880
gcctgcagtc ccagctacca gggaggctga ggcaggagaa ttgcttgaac tcaggaggca   20940
gaggttgcag tgagctgaga ttgcaccact gcattccagc ctgggcgaca gggcgagacc   21000
ttgtctcaaa aaacaaaaca aaacaaaaca aaaacctgtc actttgggaa tatctcaaac   21060
ctagtcatcc aagtggttgt acgattttag tgtctgcata tcaatattta gtgtgatcta   21120
ctttcttaga ttctcaaata ctgccaatgg gcacatgtca tgaaataatg tcttttagag   21180
gacaagagag tgctaaagtc tcattattgc agtttaagaa aaacaattct gtaacagttt   21240
aactttatag gaaatgcctt ttgttttattt atttttttc ttttgaggct tagattttta   21300
tttttatgtt tttagagatg gggtcttcct atgttaccca ggctggcctt gaattcctgg   21360
gctcaagtga tcttcctgct tcagcctcct gagtagctgg gactagacgt ccactactgc   21420
tcctggctgg aagtttagat tttaatttaa actcttctat tgggaaactt tgtatgtttg   21480
ctttaccact taacatttgc atgcattatt gtacctattg tctcctactt aaggaagggc   21540
agtttatgct gttatatgaa gtgaattaac ctcctatggt acttcagttt tctctatgct   21600
aaaagtgtgt tctagatttt tgaaaaactt acttaattt cattcattta ttcaaatatt   21660
tgagcattct gtagttgctg gggaaatagc agtgaactga agaatgtctt tgttcttatg   21720
```

```
gggcttaagt tcctagttga tcatattgga aggagataca tgaaaaaaga aatatatgaa   21780
caatggaggg cgatgagtac tgtaaaggag aattcagcag gggagatgtt gctgttttag   21840 atagagggt  gtcaagagac attgtgcaga gacctgaacg aagtgaggga gcaagccatg   21900
gagatatcta gggaaagagc ctatcaggtg gagagaagag tcctagggca gaaacgggca   21960
aggtgtgttc caggagcaga gaggggacag ctgtgagcaa ggggagagtt gtagggaagg   22020
aggcaaagag agacatctgg ggcaaaatgg attgactggt gggccgtggt aggactttgg   22080
attttttcct gagtgggttt tgagcagggg aatgaaatga tctgactctg gttttttttt   22140 ttttggaga  caaaatcttg ctctgttgcc gaggctgaag tgcagtggcg caatctcggc   22200
tcattgcaac atctacttcc tgggttcaag ctatgctcct gcctcagcct cccgagtagc   22260
taggattaca ggcttgggcc accatgccgg cgaattctg  ttttattttt tattttttat   22320
ttatttttat gtttatgttt tttgagacgg agtctcgctg tgtcacccag gctggagtgc   22380
agtggcgcga tctcagctca ctgcaacctc tgcctcccg  gttcaagcaa cttctcctgc   22440
ctcagcctcc cgagtagctg agattacagg cgcctgccac tacacctggc taattttgt   22500 atttttagta gaaacgggat ttcacctgt  tggccaggct ggtctcgaac tcctgacctt   22560
aatttatctg ctcgccttgg cctcccaaag tgctgggatg acaggtttga gccaccgtgc   22620
cagccaggac tcttattttg aaaggatctg taatgtggag aatagaaggt agagggacaa   22680
ggatgaaagc atccaggcca gttagcctag tccagctatc taggtaagag atgctggtgg   22740
cctggattaa ggctgcgtca gtgggaggtt gtgagaaagg ctcaccttcc ttttttttt   22800 ttttttttt  ttttgagaca ggatcttact ctgtctccca ggctggagtg cagtggtgca   22860
atctcagctt actacaacct ccgcctcctg ggctcaagtg ataccccac  ctcagcctcc   22920 caagtagctg ggatcacagg cttgcgccac tatatccggc taatttttgt atatttcgta   22980
gagacagggt tttgccatgt tgcctaggct ggtctcaaac tcctgagctc aagtgatcca   23040
cccgcctcag cctcctaaag tgctgggatt ataggcctga gccattgtgc ccggtcactt   23100
ccagattttg aagacagagc caacaggatt tgttaatgga ttaggtgtgg caggaggagg   23160
gggaggaaga gagagagaga ctggagttga agttaaggct catttcaagg tttttagcct   23220
caacatgtgc aggaatggag ttgtcacttg ctagaatggg ggagactgga ggagaagccg   23280
gctgggagag gttttaatg  aaggggttgg ctttggatac attaagtttg acatgcattt   23340
tagacatcca ggtggagata ttgaagaggc agttggctat aagtgtctga tgttcatatt   23400
agcggatggg gctagagaca taaatttgag aattgtcagt gtataaacgt tgttttgaaa   23460
gaaagtgggg ctgaataatt tagaaaggag tgcatagaga aaataagttt actattaaaa   23520
tagctttaac aggccgggca cggtggctca tgcctgtaat cccagcactt tgggaggctg   23580
gggtgggcag atcaaaaggt caggagtttg agaccagcct ggccaatatg gtgaaaccct   23640
gtctctactg aaaatacaaa aattagccag gcgttgtacc gggcacctgt agtcccagct   23700
acttgggagg ttgaggcagg agaatcactt caacccggga ggtggaggtt gcagtgagcc   23760
aagatcacgc cactgcactc catcctgggc aacagagcaa gactccgtct caaaaaaaaa   23820
aacaaaaaaa aacaaaaaaa aaaaacttta acagcaaagc ctcttccttt aaaattatga   23880
atttttttct tatggaagtt ggactctttc attattaagt ctacattcaa tcactatgtt   23940
agtaaaaatg ttgttctagt tgccgaatgc aataaaccag ctcagactta gtggcctaaa   24000
gcagcaatca tttgactatg ttcgaagatg ccgtgggcag gaatttagat aacagcaggg   24060
```

```
atggcttgtc tttgctctgc gatgtctgag gtctcactga gaaaactcaa gcggctgggg    24120
gtaataatca tctggaattt tctttactcc tgtatctgat gtctgggctg cgatgactca    24180
aaggctgatt tcagctgaga ctgtagacca cgtgcctact tgtggcctcc ccttttgcct    24240
tgggtttctc acagaatgtg gctggttctg gagaatgaga cttccaatga aatcaggtgg    24300
aaatgacatc tcgccgcttt cagcatgctc tattggttgg aacagttatg gacttagcta    24360
gattcaaagg aagggaacaa agacccctc ctctcagaga gtggggcata atgagagaat     24420
ttagggccat gttatccaac caccacaaat gccttctgaa tttgaggttc tgcctcaaaa    24480
gttcatagtt cctttgactg aaggacttct atatatccaa gcatcgtcag ccccaggtat    24540
attgttccat gtaagtgacc aggactacct tagtatttcg tatagggaaa gtgacctgaa    24600
taaatttgag aaaagaatct tccttctctc cagtaagcac tgaggtaagc attgagccat    24660
attataggtt tatgactttg agactcagaa atttaaattc ttggccaggc gcagtggctc    24720
acgcctgtaa ccccaacact tgggaggcc aaggcaggca gatcacttga ggtcaggagt     24780
ttgagaccaa cctggccaaa atggtgaaac tccatctcta cgaaaaatac aaaaattagc    24840
caggtgtggt ggcgggcacc tgtaatccca gctactggg aggctgaggt aagagaatgg     24900
cttaagttct ctttatctgc tttatttcag ttgcctctct tagatgaata ttaatgactt    24960
acatagcatt ttagatcagt ggatgttttt gtgattcttt tatttgagct ttggccaaag    25020
ataacagtac ccacaggttt tttccagcta ctcgctcttc tcccttcagt ggccctcgag    25080
cctggaaaat ctgacatgac aatgtgcttg ctcaacctac cactgttttt cttttgaaaa    25140
gtttggcagc ctgtttctga ctcctatgaa ggtgaattcc tcagcattca cagtttatta    25200
gaaaaatact ttgcttctct ccaaactcga aattcaagat aaccaaacct atatataggc    25260
tgatctttca ggatgcagtt gtcatgttga tgccatgctt ttcagtatcg tggccatcat    25320
ctgttcagta ggggaggtgt acttctgtaa tgggaggtgg tggttatgtg tgtgtgcaag    25380
tgtttatttg gtgtcttaag ttagcctgtg ggaagttcta aatcaggatg gtacgtggtt    25440
gccagcagag agctgctcct caagtgaagg aggtagaatc aaagccaata ggaaagagcc    25500
tcagatgctt atatatgtac cgtgggggatt cagagtgaaa gcagtcattg gactaggggt    25560
ggggttaggg agagcctgtc tgacagacac aagaaaggga tggataacgc cacccagaga    25620
aaaaagcatt ttaggcaaga acaaatatga aaaaggaaca aagtctgtgg gtgggggca     25680 aggaggagat aagttgactt gaaggaagac aacacttatg aaagtcacct ggaggctggg    25740
tgccatggct catgcctata atcgcagcac tttgggaggc cgaggtagga ggacaacttg    25800
agcccaggag ttcgagacca tcctgggcaa catggtgaga ctgagtctct accaaaaaaa    25860
aaaaaaaaag aaaattatcc agacatggtg gcatgtgcct gtaatcccag ttactcagga    25920
ggctgaggtg ggagggttgc ttgagcccag gaggttgagg ctgcagtgag ctgtgatcgt    25980
attattgcac tccagcctgg gtaacagagc aagaccctgt ctcaaaaaat gaaagtcatc    26040
tgtaggctgg agagaggaac tggaagggggc taaagttggc tgagtagtta cagagcctga    26100
gataagggta aagattttgc attggacaat gagatgttag tgtgtgtttt tgagctgggg    26160
agtgctgtga ttactctctt attgaagaat cactgaagga ttattcttga atcagtgatt    26220
cttgatcatt cttgaatttt tcaaacagca aaactggaag agttggccta ttcctcagaa    26280
tattttctaa ttgggcgcag tgtcctcact tgggagaacc tggctacaca ctttagttgt    26340
aattcactcc agtcgttcat tcattcaata cctattttt cagcaccttat tatgagccag     26400 acactatgct ggatgccagg gttcagggta ggacacgcta gtgagcaaaa gccaagactc    26460
```

```
ttcttgtctt catggggctt tcagtccagc atagtggtta tgagtccaag ttaatggagt    26520
cacagtactt gggtgcaagt catggtgatg gtgatagaag gaaggcatgt gtgagggcca    26580
gtggcaggca ggagcctggt gttttttgagg acctgaagaa ggagcagagt gagtgccagg    26640
aacttagcca ccagctggta ccagccatac gagaggggca gagccagcca ggatgtcggt    26700
catgctagta atgagtacaa acacttacat gctgcacgct attgggctcc tgagtgctac    26760
gtgttcatta gctcgatgaa tttgtacagc aaccctgtga ggtaagcact gttctctccc    26820
ctttctatag atgaggaaat taaggcacaa agaggataaa taactggcac cagctacacg    26880
ctaagtgatc gaagtggtgg aaccaggatt caaatccatg ctattctgcc ttaagataac    26940
aaatcttgtt ttttagccta agaacagagc agtcatcagg agggttttaa gtaggggtgt    27000
ggcaagatca agtttgtgtc ttgaaaaggt ctctctaccc acagtgtgga aaatggcctg    27060
gaggcaagca cacagatgtt gggagacagt taacagctct tgccatggcc ccctatgcat    27120
tttggctctg atgtttctgc ctgatttttc tcttgcctct gcctcttttc ctgagggggat   27180 ggcaggtttt accattcagc tggagtacaa accctgaacc cttttttggtt aaatatctac   27240 ttgcttttcc tacagtatta ttttgagttg ctgtggctgt aatgtcttga gggaatcgag   27300
cttgacagta atttatagaa caaacagttt ttagagactg tgtggcccaa ttgccctctc    27360
aatgttggca ctcctgccat gacatttacc atgctgagca tgtgaccgcc atctgaatac    27420
caaatgccac aggaacctgg gaggttgtca cttactcctc cctttctctg agtcacctttt   27480 gcccttcagt cagtcaccaa gtcccatcac atgtagctct gtaatgtcac agaagatgga    27540
tgtctgcctc aaaacactta caatgctgct acctaaattg ggcagccacg acctcccacc    27600
aggattattg cagcctgagg gatcttttttg aaatgtaaat caaactatca cttgtctgtt   27660
taaagctttt caaagactta ccccattgcc cttggaagaa agtgcagata tcttgacagg    27720 agagcccttct ccagcctcct cttctgccgt ggtctccttg tacagtctct acagtgtact  27780
gcttcattag aaccctggag attattattt gctagttctg ggctaagaac tggcacctgg    27840
ctttgtagag ctcctcagga gattctgagg cgtattcaga gttgagccct gatctctgct    27900
ctgatttcga ggttctcgtt atatttatta atgatcacga aaaaatttat tattattctt    27960
tggcctcact ttagcatcat ctgaggaatt ttttttttttt tttgacagag ttttgctctt  28020
gttgcccagg ctggagtgca atggcgtgat ctcagctcac tgcaacctcc gcctcccggg    28080
ttcaagagat tctcctgcct cagcctccca gtagctgaa attacaggca tccaccacca    28140
tgcctgctaa tgttttttgta ttttttagta gaggtgggct ttcacagtgt tggtcaggct  28200
ggttttgaac tcctgacgtc agctgatcca cccacctagg ccccccagag tgctgggatt    28260
acaggtgtga gccaccgtgc ccagccgtag ctttcgaaat ttgaaacctg gtcccactgt    28320
cagaggttcc aatttggcac tggtttggtt cccaggcatc tttcttgctg tatatatttt    28380
ttagtgtcag ccagggtgga gacctctgta ttacttcatg gggaagaatt tgggagaaga    28440
tgttgtgagg agacaggttc tagtcctaga gtgatttatc ctttctcgta cagatttcca    28500
ggtatttgag gggccactct tctgtaattc atgttttttct ctcctaacct cactcctgtt   28560
gcctgcatct tcttgctgag caaaatattc aaggtcttca actcctcaca ccctggttgt    28620
ccctccctgg atgtgtttgg ttgttttagt gttccatttc aattttgata cacagaatta    28680
gaatagcatc cagatgtggg tctgttacag ctagactact agatccttca aaatccaagt    28740
actagtatgt ctattaaaat accataagat cacattggct agttacaatg gttggtttgt    28800
```

```
gggttactta aaaatcaact aaaattctttt ttttttttttt gagatggagt tttgctcttg    28860
ttgcctaggc tggaatgcaa tgacacaatc ttggctcact gccacctctg cctcccaggt    28920
tcaagcaatt cccctgcctt agcctcctga gtagctggga ttacaggcat gtgccaccat    28980
ggccagctaa ttctgtattt ttagtagaga tgaggttttt ccatgttggt caggctggtc    29040
tcgaactccc gacctcaggt gatccacctg cctcagcctc ccaaagtgct gggattacag    29100
gcgtgagcca ctgagcctgg ccaaaattcc cactttctaa tactcctgta gtagctgggt    29160
acggtgggtc acatctgtaa tcccagcact tttggaggct gaggctggag gatcgcttga    29220
gcctaggagt tcgagaccag cctgggcaag atggccagac gccatctcta atttaaaaaa    29280
aagaaaaaac aagactccta tagtggtgaa gaacagacat tccgaaaaca gactgtgcgt    29340
tatgattcca gctccatgcc tttactacct gtgttgtgac tttggataaa tcacttaaaa    29400
atcttttttt ttttttttttt tttttgagac ggagtcttgc tctgccgccc aggctggagt    29460
gcagtggcgc gatctcggct cactgcaagc tctgcctccc aggttcacac cattctcctg    29520
cctcagcctc ccaagtagct gggactgcag gtgcccgcca ctacacctgg ctaatttttt    29580
gtatttttag tagagacggg gtttcaccgt gttagccagg atggtctcga tctcctgtcc    29640
tcgtgatcca cccgcctcag cctctcaaag tgttgggatt acaggcgtga gccaccgcac    29700
ccggccaaat cacttaaaat tctgtgcctc agtttctcct ctgtaaagtg ggataaaaat    29760
agtacctatc tgatagggtt gttacaatta tgaaatgagc aaataagtat gtcaagtgtt    29820
taaaacagcg cctggcttct tgtaaaaagt gctatataaa tcatagctat aatcattact    29880
tatttcgact gctctttaac caaggttctt atttttcatc ttttttcttt gttttgaata    29940
tcacttagtg ttttcacctt ttactctttt taggacctag agccatccta ggtgaaatac    30000
gtatggagat atttgatcag gtcaccaccc agctctcctg acctcccttc tctccttaaa    30060
ttaacatgcc aaatcacagc atcactgact ccttccctcc cgatatgata agagtgtgca    30120
ttgaaatgca tgtatttac ttagcaggga aagctgatta gtgattatca cacttaaccc    30180
ctagtgaatc tgatggatta acctgctttc caggacacta aggaaatggg tttaagataa    30240
gaaatatctg gctgggtgcg gtggcttac gcctgtaatc ccagcacttt gggaggccga    30300
ggtgggcaga tcacgaggtc aggtgattga gatcatcctg gctaacacga tgaaaccccc    30360
tctttactaa aaatacaaaa aattagccgg gtgtggtggc gggcgcctgg agtcccagct    30420
actcgggagg ctgaggcaag agaatggtgt gaacccagga ggcagagctt gcagtgagct    30480
gagattgtgc ccaccgcatt ccagcctggg caacagagtg agactacatc tcaaaaaaaa    30540
aaaaaaaaaa agtaagaaat gtccatgaaa gggagaccct gggggaaagg aacaataact    30600
gcagctctga ggatctggca ccagcagcac cagcacagag gatgctgta caaccattat    30660 tgattttaac tttacaacag ttcttcaaag gagagagagt tccctgtttt actgaagaga    30720
aagcccattt ggtagtgaaa taccattccc aaagacaaat agctaataaa tgtcaggcag    30780
ggttttgcac ccaggcccat ccagctcccg tctctactgt cctttccccc acaccacact    30840
gatacagagg aatgtgtctg gttggggaag tggaagtgtt cccaagtggg gaggtcatct    30900
gatgcacaaa tttggtctgt tttgtgggtt ttcttgtttt agttttagtt tttgtagagc    30960
tcagacctgt tcttaggcag ctttaacaat caactgtgca ctcagtaatt gacaaatcat    31020
gtttgttact tttaatttag agggaattag gtttgttaag ctcttgctcc ttctttagag    31080
atggggtcta gctctgtcac ccaggctgga gcgcagtggt atgatcacag ctcactgcag    31140
tctcaatctg ctcaagtgat cctcctgcct cagcctccat gggactacaa gcatgggcca    31200
```

```
ccatgctagg ctaattttaa aaaaatttt tgtagaggc aaggtctcac ggtgttgccc    31260
aggctggtct tgaactcctg agctcaagca atccctcttc caccttggcc tctcaaagtg    31320
ctagaattat aggcatgagc caccatgcct ggcctttact tctttcatat attcaaattt    31380
tgtcatatta gtagggaact ataactcaag ttttcttata gattgatgtt catttttaca    31440
agcttgatcg tcattggttt ttaattttaa agcaaatcct gttatatgta attgaacatt    31500
acagtaatta tagtaatttg tttcagattg ggcactcaag tgttaatatt ttgtctcttt    31560
aggaaatcaa aactagattt atatatagac ttcttattgc aagtatctag tcttaaatct    31620
tacaaaggta ctatttggac ttaaaactat gaaattgtgt gcttactata taagtgtact    31680
tattttgagt tatgttttaa acttgaaatt ccattcttaa tgtctagagt aattatgaat    31740
ggttaaatta tgaatgactc taatagttta aagctacagt atttatttat ttatttattt    31800 aatttattt ttgagatgga gtttcgctct tgtcgcccag gctggagtgt agtggcacca    31860
tcttggttca ctgcaacctc tgcctcgcgg gttcaagtga ttctcctgcc tcagcctccc    31920
aagtggctgg gattacaggt gtatttcacc atgcctggct aattttttgta ttttttagtag    31980 agacaggctt ttgccatgtt agcctggctg gtctcgaact cctgacctca ggtgacctac    32040
cctcctcagc ctcccaagga ttacaagcat gagccaccac acctggccta cagtatttta    32100
atgtggactc tctgtcatcc attatgctgt ttatcctgtg gtgaaaattt tatgaagatt    32160
gaatgttttt ctctagcgtg aattgctttc tcttactttt ctcattttt tccttcctaa    32220 tctacttgca gatacttcag attattttta gaacgtggta tggtgagaac aaataaattg    32280
gggtttccaa atcttaataa attatgtggc cctcagtggg attagcaggg ttgtattgaa    32340
aacaccaata gaaacaaaat agttcttta tgcgctttaa ataaaaattt cttttcaggc    32400
caggcgcagt ggctcacacc tgtaatccca gcaccctggg aggctgaggc aggcagatca    32460
cctcaggtca ggagtttaag acaagcctgg ccaacatggt gaagcgccgt ctctactaaa    32520
aatacaaaaa ttagccgggt atgatggcgc atgcctgtaa tcccagctac tccagaggct    32580
gaggcatgag aatcacttga actcaggaga tggaggttgc agtgagctga tggtgcca    32640 ctgcactcta gcctgggcaa cagagtgaga ttctgtctca acaacaaca acaacaataa    32700 caaaacatct cttttcaggc caggtactgt ggctcacgcc tgtaatccca gcactttggg    32760
aggccaaaac aggagggtcg cttgagacca ggagtttgag accagcttgg gcagctggtc    32820
tctatttgaa caaacaaaca aacaaacaca atactcttt catagaaaaa tgtttactac    32880
acaataaact ttaaaagaat atgcagctgt attaatgcta tgactccaat gtaaaaaaaa    32940
aaaaatatat atatatatat acacacacac aaacacattc tgaaatagat ttaaaggaat    33000
tacatcaaca tgtcaatttt tatttttcg gagacagggt ctcgctgtgt cacccaagct    33060
ggagtacagt ggtgcaatca cagctcactg cagccttgac ttcctggcct caagtgatcc    33120
tcccccctca gcctcccaaa gtgctggggt cacagaccac cacacctggc aacatgtcag    33180
tttttgttct gcatagtggg atggtgggat atggatgttt ttatcttta ttttcttttt    33240 tatattttc taaattttcc acattgaaca ttattttata atctttcaaa catatctctt    33300
aaaaggactg gttcctatag aattcagtgc aagaaatctt ctgtgtttct ttatactttg    33360
gttgccttga tcactgggcc tttcctgaca gcaaagaaga ggttagtgta ggcagcagat    33420
aaaacacagg tatgctctat ttaaaatgca tgtatttata ataaagtat aggtggtacc    33480 caaaggaaaa tgtcatgaca cattgcaaag tggaacagaa gttatcttta gatcactttc    33540
```

```
tgttctggat tattgtatga gcctgatttt cgtctctctt tccgccttcc ctcaccctcg    33600
ttgtaaatcc actagtgcat ggatgtgaag tacaagtctt aactttaaaa agttttatga    33660
agctgtgtag taaatccctt tgtaagtggg tcttgactgc gtttctcaat atatcttttg    33720
gtttcattag attcaagtat ataaatgaga actgtaactt tggacagact ttttcagtca    33780
tctttacggt aataagttcc caattagaca atagttattt gttttatgac ttgctgttgg    33840
taggttatcc ccaagggact gagaaattcc tgttttgaaa agtccaaaaa gtctttgatg    33900
acttgctgtt tcattttttt cttttctctt cagttataga aaacaggatt acacccacct    33960
tgcctttgta cagtgcatct actatctgct gacttaacct gagtaaatgc tttgaattga    34020
gccccatata atgtcctaag gcagcctata tggagtaatg aattgtcttc tctcttatgc    34080
acccagagtg gtagttggca ctcaagttgt tcctcagata actttgtgtg ttctggggct    34140
caatgaagta gttattaagt cacaggcttg gggagaacat tcatcctatg gcattgaatg    34200
aagtgttgcc caattctaga atgtctaata aaattttttt aaaaacccac aggcttagaa    34260
ttattccgta gatatgaagt aatgtagtta gaacttagtg gagttcttta gattaacttg    34320
taatttgaaa aaccaaaatt gaaattgtga ataacatgg gctctttgag gtcttttcca    34380
gtaaaacagt tacagtaaag ctgcttggca gtgattttcc tagacacttt ggctagtcat    34440
ctcctgtgac tgctgttaat taaatatggt ttgtagctaa gcagcctgta aggagaagac    34500 tatgaagta tttgcatatt ctctccttga aaatactacc tggtctttgg ctttaagtta    34560
tacttttatt ttccctgta gaataactat taaagtatta cctatggtga ttagactaag    34620
aagtaaaaca tgaaatcagt cattgttggt gccctggtgc cttcttttt ttttttttga    34680 gacagagtct cactctgttg cccaggctgg agtgcaatgg cacgatcttg gctcactgca    34740
acctctgcct cccaggttca gcgattctc ctgcctcagc ctcccaagta gctgagacta    34800
caggcgccca ccaccacgcc tggctaattt ttgaattttt agtagagaca gggtttcact    34860
atattggcta ggctggtctc aaactcctga ccttgtgatc cgcccacctc agcctcccaa    34920
agtgctggga ttataggtgt tagccactgt gcccagcctg gtgctttaat tttatggaaa    34980
aaactactag ctggtttctg ttttaagaaa taacacaggc cgggtgccat gacttgcgct    35040
tgtactccca gcagtttggg aggccgaggc gggcggatca cgaggtcagg agtttgagac    35100
cagcctggcc aacatagtga aaccccgtct ctactaaaaa tacaaaaatt agccgggcgt    35160
ggtggggcat gcctgtagtc ccagctactc gggaggctga ggcaggagaa tcgcttgaac    35220
ctgggaggtg gaggctgcag tgagccaaga tcgccccact gcacaccagc ccgggtgaca    35280
gtatttcatc tcaaaaaaaa aaaaaaaaa aagaacacaa ttattgtact acttactagc    35340
cctcctctgt cccagctaa aaataagaac agcaacaacc aaaaaatcct tagttatgta    35400
ctggaaatga attagataat tttcaataac ttacacgtttt ttaggatatg ttagtttgaa    35460
aatgcaaata ttcatgcatg accccagtgt taatctatga tggagcaggt atagtgggat    35520
gctgtttcat gatttaattt ggaccttcag ggagtagact gtgatgcctc tgcatttgta    35580
tccaagacaa ataattaaat agtctatttt tggctgggca tgatgcctca tgcctgcagt    35640
cccagcactt tgggaggctg aggtgggagg atcgcttgag gccaggagtt caagatcagt    35700
ctgggcaaca aaatgagacc ttgtctctac aaaaactaca aaaaattagc tgaacattgt    35760
ggcttgtgcc cctagtccca gctactcagg tccctgagtt aggaggattg cttgagccca    35820
ggagttggag gttacagtga tctatatttg ccactgcact ccagcctggg tgacagagag    35880
agaccctgtc tcaaaaaata aagtctgttt ttaaaattaa ttttaaacac tggagtttat    35940
```

```
tacaaaaagc agttggttct ttttttaaat cattttttt taggagaacc accgctttt    36000 ggctacattg tctagagtag cagtgttcaa taaaaataag atccaagtca catatgtaat  36060
gttaagtttt cttttagttt cttttttctt tcttttcttt tctcttcttt ctttctttct  36120
ttcttttttt ttttttgat atgcagtctc actctgttgc ccaggctgga gtgcagtggc   36180
acgatctcgg cccactgcaa cctccgcctc ccgggttcaa gcaattctcc tgcctcagcc  36240
tcccgagtag ctgggactac aggcatgtgc caccatacccc agctaatttt tgtatttta  36300 gtagagatgg agctttgcca tgttggccag tctggtctca aactcctgac ctcgggtgat  36360
ccacatgctt tggcctccct aagtgctggg attacaggca tgagccacca tgccctacca  36420
atgttaagtt ttctagtagc catattaaaa aagtaaaaa gaaatgggtg aagttaattt    36480
taataatata ttttatttaa cccaatatat ctaaaatatt atcatttcaa catgaacaag  36540
atactttaca ttcttttgtt tttcactaag tcctcaaaat ccagtgtgta ttttatattg   36600
acagcatagt tcagtttgaa gcagccacat ttcaagtgct cagtagccac atgtggctag  36660
tgactccata ctggactgtg taggtttaga gtttcagtaa atttgtatgc aatagaatct  36720
acataaattg gcatattatg cagatttctt tgtatgcaca tcagttcttg catagcataa   36780
gtcaggtcat gatgctttta gtctatgagg cagatttttt tttttttt tttgagacag    36840 agtctcactt ggtcacccag gctggagtgt agatgcacaa tcttggctca ctgcaacctc  36900
catgtgaggc agattttaac ttggccctaa tgcaaatatt gtaagagaga tctaatggcc  36960
tttgatttct tacagagggc aatcaataca tgccatggtt acaatgcttc agcatatagt  37020
atgcacgtca gccactgctt ttactctggc tagtgcttag tgtacctgta ccactgccca   37080
ggcagcattt gtcctgtggc aggtgaatct tagggtggaa ggtggcaagt aacattgctt  37140
ttttttgaga gggagtcttg ctgtattgcc caggctggag tgcagtggtg cgatctcggc   37200
tcactacaac ctccacctcc cgggttcaag tgattctcct gcctcagcct cctgagtagc  37260
tgggattaca gacggccacc accatgctcg gctaattttt gtattttag tagagacggg    37320 gtttcactat gttggccagg ctggtctcga actcctgacc tcgtgatcca cccgcctcgg   37380
cctcccaaag ttctgggatt acaggtgtga gccaccgtgc ccagcctaca ttttaaatt   37440 aattaattat aagcaggatc tcactgtgtt ggccagactg gtcttgaact gataagagtt  37500
caagaccagc ctaggcaaca tggtaaaacc ctgtctacta aaaatacaa aaaaaaaaat   37560 tagctgggca tggtggtgcg tgcctataat cccagctact tgggaggctg aggcaggaaa  37620
atcgcttgaa cccgggagac tgaagttgca gtgaggtgag attgcaccac tgcactccag  37680
cctaggcgat tccatctcaa aaacaataac aacaaaataa cattgttgga atatttagtt  37740
aatttataga agcgtattgg cctaattggg gcaaatacct tattctgaca ttctctctat  37800
ttgctttact gagcttttc accagtggaa tttaagccct tgatacatga ggagggaaaa  37860
taccttggag ctgtgctgca catgtaaagt acacaggaga tttagaaaac ttcgtagcaa  37920
aaaaaagagt gtaaagtatc tcattaatag ttttttgtggg ctggacacgg tggctcaagc  37980
ctatactctt ggcacattgg gaggctgaga tgcatgagtc taggagtttg agaccagcct  38040
gggcaacaca gtaggaccccc gtctctacaa aaataatcag ccagatgtgg tgcgcatctg  38100
tagtcccagt tacttgagag gctgaggtgg gaggatcgtt tgagctggga agttgaggct   38160
acagtgagct gtgattgaac cactgcactc cagcctgggt gacagagtgc ctgtctccaa  38220
aaaataaata aataaataat aatatgtttt gtatgttcat atgttgcaat aacattttgg  38280
```

| | |
|---|---|
| atatattaaa tgaaataaaa tacattaaaa ttaatttcac ctgtttcttt tcttttcttt | 38340 |
| tttttttttt tttttgagat ggagtctcgc tatgtcatca ggctggagtg cagtggcacg | 38400 |
| atctcggctc actgcaacct cctcctcctg ggttcaagcg attcttctgc ctcagcctcc | 38460 |
| ctagtagctg ggattaaagg catgtgccac cacacccagc taattttgt atttttagta | 38520 |
| gagacggggt ttcaccatat tggccaggat ggtctcgatc tcctgacctc atgatccgcc | 38580 |
| tgccttggcc tcccaaagtt ctgggattac aggcgtgagc cactgcaccc agcctcttt | 38640 |
| aacttttta gtatggctac cagaaaattt aaaatgcatg tgtggcctgt attctatttc | 38700 |
| tgttggatgc tgctgcctta gattattaat tattcaatgt aaagactgct gggaggtact | 38760 |
| acctgcactt ccctgaatat atgcttgaga gctccaccag ccgtcttcac agtagcaaga | 38820 |
| ggggtattct gagtctgtcc cccaaagagg gagggagaag tgcagccctc tcaggttctg | 38880 |
| tcagaaaacc tgatcccagg ccaggcgtgg tagcttacgc ctgtaatccc agcactttgg | 38940 |
| gaggttgagg caggaggatt gcttaagccc aggagttcga gaccagcctg gcaacacag | 39000 |
| tgaagaccct atctctacaa aatttttt aaaaaaatta gccaggtgca gcaatgctgc | 39060 |
| ctgtactccc agctgcttgg gaggctgagg taggaggatt gcctgagccc aggagttaga | 39120 |
| ggttgcagga gttagaggtt ccacgatcgc acctttcatt ccgttacatt tgctgccttg | 39180 |
| agaacagaag acctgctggt tttgttgcca gtttgctcag tcattttat gaaaaagcca | 39240 |
| gtgctaacta ggtgcttctt cgtgccttct ctgagaatca agaactctag tatgtttgcg | 39300 |
| tgtgttcagt ctctcattaa atgttctcac tatcccagag aaccatctca ttggaccttg | 39360 |
| gtctgtacat accttcatct ttggctctga cttgtaatta tttttagaac ttctcttttt | 39420 |
| ttttttttgg agacagagtt ttgctctagt tgccagactg gaatgcagtg gcacgatctc | 39480 |
| agctcacctc aacctctgcc ttccaggttc aagcaattct cctgcctcaa cctcttgagt | 39540 |
| agctgtaatt acaggcatgt gccaccacgc ctggctaatt ttgtgttttt agtagagaca | 39600 |
| gggtttctcc aagttggtca ggctggtctc aaactcccga cctcaggtga tctgcccgcc | 39660 |
| ttggcctccc aaagtgctgg gattacaggc gtaagccact gcgcctggcc taattttaga | 39720 |
| acttgttaaa acaacttggc ctctattgat atttccatga cccatgctat tcagaaagag | 39780 |
| gattacaggt aattagctgg ctgggtttct cataccagag catttcactg ggatgttcct | 39840 |
| gaacctggga caacttttat gcctggcatt tttctttcct tctctgttgt cccagactaa | 39900 |
| gcaattttta aaatagttat tatttgttga gtaggagaat ctcaggcaga tcttcctgga | 39960 |
| tcctcattta tactttaaa cctgtagtct tggaattagt gctctgtccc caacccaa | 40020 |
| acatccaatt tctacatttt ggctacagta caggtttact gtgtataact aaaagggctg | 40080 |
| tggaggagaa agaaaggaac cgacatttgt tgggcatctg ttatgtgcca tgcactgagc | 40140 |
| tggatgctgt aggaatatct caatacctct gaggagtggg aattattatc tctattttat | 40200 |
| agacaaggga atagaaatct gggagttaag taatttttta atttcacaca cttctggtag | 40260 |
| ataatggatt ctagaacctg gcataatagc cacttgtcat cccagtgtaa aagagatgtg | 40320 |
| tggccagatg gggtggctca catatgtaat cccagcactt gggaagccg aggcaggagg | 40380 |
| atgacttgag cccaggagtt caagaccagc ctggcatgt tttgtttgtc tcacgaaaca | 40440 |
| ttttttaaaa aatgagtgtg catggtgtt gtgtgcctat agtcccagct cctcgggagg | 40500 |
| ctgaggtggg aggatctctt gagcccatga tcatgccatt gcactctagc ctgggccaca | 40560 |
| gagcaagact ctgtcttcaa aaaataataa aaaggagctg tgattatccc aaggtgggga | 40620 |
| ttgtgaatgt gtttgtattg ttctaaactg ggagaaacag gctgggtgtg ttggcttatg | 40680 |

```
cctgtaatct cagcactttg ggaggccaag gtgggaggat cacttgagtc caggagttca   40740
aggccaccct gggcaacagg caaaaaatag agacccatc  tctattttt  aaaaataaaa   40800 taaactggga gaaagaagca gggtcctccc cagagcatct ttatccctag tcacagacct   40860
gacacctgtg ttgggcaatg ctacttcta  gattgtttac ccctactggg acttgtggtg   40920
aacatatgca cactttggtt tacagttggg accctgatt  ttagcaggat ggcccaatgg   40980
aatcagctac agcagcttga cacacggtac ctggagcagc tccatcagct ctacagtgac   41040
agcttcccaa tggagctgcg gcagtttctg gccccttgga ttgagagtca agattggtaa   41100
gtccttctta agtgactctc caaattgtta ggtttcagtt tgagtcaaga gacatgaact   41160
cttaatgtca tgccttgctg ttccattaaa aaatgtatgg gtacaggtga tggggaaaat   41220
gagatcagga gataaagggg caccctttgg tcttgtaaag ccttttttat cttagaaggg   41280
catgtgggca actgtctttg acacattgaa accgcctgta tggtggtgga tgtcttgaag   41340
gttgatttgg acctcattta cttgggcaga tcctctatat attctgataa tccagtgatg   41400
tggtagacat attttttctc tgaatgtgaa ttctgtcata gctagaactt tgggttgata   41460
cttgtaattc ccctttagtt aaaggaagga gccacagggg tgtattagtc tgttctcaat   41520
ttgctataaa gaaatacctg agactgggta atttataaga aaagaggttt aatcggctca   41580
tagttctgca ggctatatag gaagcatagc agcatctgct gctggggagg cctcagcaag   41640
cttccaatca tggcggaagg cagagaggga gcaggcaggt cacatggcca cagcaagagc   41700
aagagagcaa gggggaggtg ccacacactt ttaaactatc agatctcaca agaactcact   41760
gtctcgagga cagtatcaac agggatggta ttaaaccatt catgagaaac ccaccccat   41820 gatccagtca ccttccacca ggccccacct caaacagtgg gggttacatt tcagtatgag   41880
atttgggcag ggatgtagat ccaaactaga tcacaggata agggaagtag attccattca   41940
tagagcagat aatggcacag atgtccagca actattttct tcactttaat atgctcaggc   42000
tcactactga ttttggttta attcaggcca gtgttaatat gacctggttt ttccagaatg   42060
catactctga tttggtgaag ggccaggagg tgattcacag atgttggaga taggccatcc   42120
cagcctggga ttacttattt gtactaataa atctgaccag agttaattga gggtttaaag   42180
caaaacagca tatctgtcta ctttgctcaa atattttaca aatacaacag attatgagag   42240
tgggtaataa tatctggaat aattgttttt ttgttttgtg gttttttttt ttttttttt   42300 gagatggagt ctggctgtag cccaggctgg agtgcagtgg tacagtctcg gctcactgca   42360
cctctgcctc ttggattcaa gcgattctcc cgcctcagcc tcccgagtag ctgggattac   42420
aggtgcccac caccacacct ggctaatttt ttattttag  tagagacagc gtttcaccat   42480
gttggccagg ttggtctgga actcctgacc tcaggtgatc cgcctgcctc agcctcccaa   42540
agtgctggga ttacaggcat gagccaccat gcctggcctg gaataattgt taataattat   42600
tacattgatg gcattttatt gctgagcaag aagaatctaa catgatgaat gggttatagc   42660
atcaggtttg cttgttttt  ttgttttttt cctctttctt gatggtgatt tctgtgtttg   42720
tgtgtatgcg tcggcttcag agccattctt tatcattctt ccttttccta gggcatatgc   42780
ggccagcaaa gaatcacatg ccactttggt gtttcataat ctcctgggag agattgacca   42840
gcagtatagc cgcttcctgc aagagtcgaa tgttctctat cagcacaatc tacgaagaat   42900
caagcagttt cttcaggtat gatgagaaac tgaggacaag gagaaacagg acccgcgag   42960 tcgggtgtta gtgttctttc ctggaagcat ctcttttctc atttggctaa gtaacgagaa   43020
```

-continued

```
tctatcttgt attttcaatc acaggagaag taattagccc tttctcaaag ctctgtatac   43080
ttacccgtga gcatcattac ctgagaatca cttctcttgt cacagttgaa gtaataaagt   43140
gattgttatg ttaatcatac atgttagcat gttaacgcgg tccactgata ggaagatgac   43200
tctcactgtt acatgttaaa tgtttgacca taatgggata cttcttgact aagtcagtag   43260
cttccctgca agaccaggat agtatactgt gtaaagactc agacaaggcc aggcatggtg   43320
gctcacgcct gtaatcccaa caccttagga ggttgaggtg ggaggattgc ttgagcctgg   43380
gagttttgag accagcttgg gcaacataac aagacaccat ctctacagaa attttttta   43440 aaaactagct gattgtggtg gcatgcacct gtagtcccag ctactcagaa ggctgaggtg   43500
agaaaattgt ttgagcctgg gaggtcgaag ctgcaataag ccgtgattgc gccactgcac   43560
tccagcctgg cggacagagt gagagccagt ctcaaaaaaa aaaaaaaaag actcaggcta   43620
atgtgccttc tgttacagaa atagtaacga cctccccttc gcccccgcc gacagagagc   43680 cttcacccag gctctgaagc cttttgttccg ttgtttccta gaataaatgc tttccttgat   43740
gaatacatta gttttaaggt gccacagttc agtccacatc tccatggtct gctgctgatt   43800
tttattctct ttctctccta cttatagagc aggtatcttg agaagccaat ggagattgcc   43860
cggattgtgg cccggtgcct gtgggaagaa tcacgccttc tacagactgc agccactgcg   43920
gcccaggtga gacctgagac aaaacaaatc cctggtctgg gaggaatgga aaatcaaaca   43980
actttataat gagataaatt attagatcta ctaaaaaga aggaaagaa attaaataga   44040 tcaataatca taaaaataca ttgaaaaact ctaaaaaaaa agaaagttcc accccccaaa   44100
atacattgaa aaactctaaa aaaagaaag ttccaccaaa agaatccaac agacccaatg   44160
gtttaaaagt tttgttttgt tctgacaaat tttcttttgtt tttctttttt ttttttctg   44220 agacagagtt ttgctcttgt tacccaggct agagtgcaat ggcgcgatct tggctcactg   44280
caacctccac ctccagggtt caagtgattc tcctgcctca gcctcaagag tagctgggat   44340
tataggcgtg tgccaccaca cccagctaat tttgtatttt tagtagagac ggggtttctt   44400
catgttggtc aggctggtct cgaactcctg acctcaggtg atccgcccgc ctcagcctcc   44460
cacagtgctg ggattacagg cgtgagccac tgtgcccggc ctgttctgac aaactttcat   44520
agtacagatt attccaatat cattcaaact tttccaaagt ataggaaaac aagggatgtt   44580
ttcagcttat tttatgaggc tggaaaaatc ctcatatcaa aacctaaaaa acagccaggt   44640
gtagtagctc acgcctgtaa tcccagcact ttgggaggct gagacgggca gattgcctga   44700
gcctcaggag ttcgagacca gctggggcaa tgtagcgaga cctcatctct cttttttttt   44760
ttttttgaga cagagtctct ctctgtcgtc caggctggag tgcagtggtg ccatcttagc   44820
tcactgcaac ctccgcctcc caggttcaag cgattctctt gcctcagcct cccgactagc   44880
tgggactaca ggtgtgtgcc accaagcctg gctaattttt tgtatttttt ttagtagaga   44940
tggggtttca ccttgttagg caggatggtc ttgatctcct gacttcatga tccaccggcc   45000
acagcctccc aaagtgctgg gattataggc atgagccacc gcccagcc tttttttttt   45060 ttttgagaca gagtcttgct ctgttgccag gctgagtgc agtggcgtga tctcagctca   45120
ctgcaacttc tgcctcccag gttcaagcta ttccctgcc tcagcctccc aagtagctgg   45180
gactacaggc gcgcgccacc acacccagct aatttttgt gttttagta gagatggggt   45240 ttcactgtgt tagccaggat ggtctcgatc tcttgacctc gtgatccgcc cgcctcggcc   45300
tcccaaagtg ctgggattac aggcgtgagc aaccgcacct ggcttaatta aggatctttc   45360
taaacacaag aaagaatatt tatcagaaac caaagggagc atgatgcaca gtggtgaaac   45420
```

```
actattctca gtaaaaacag caaaagataa ggatgtcttt taccattgat acttttctga   45480
gggatccagc ctatgcaaaa agaaaaagaa atgagggtac aaatattgga aagcaaggga   45540
cagaactctt attatttaca gatagatagg tcttcctcga agatccaaga gaaacaaaac   45600
taacaataac aattggaact agcaaggttt agaaaggcca ttgtatacaa gataaatatt   45660
tttagaatct gcagttcccc taatcagtag cagcagtaac ctgttagaag atgtaatgaa   45720
agtaaagatc tgggccaggc acgatgtctc acgcctgtaa tccaagcact ttgggaggcc   45780
aaggtgggca gatcatgagg tcaagagatt gagaccatcc tggccaacat gatgaaaccc   45840
catctctact aaaaatacaa aaattagctg ggtgtggtgg tacgcgcctg tagtcccagc   45900
tactcgggaa gctggggcag gagaatcgct tgaacctggg aggcggaggt tgtagtgaac   45960
caagattgcg ccactgcact cctgggcgac agagcgagac tccgactgaa aaaaaaaaaa   46020 aaaaaaaag aaagatctga ttcatagtag taaaactaaa tgtatgcaat ttgcatatac   46080
tattggtatg tatgggaaaa tatctggaaa cacatatact aaatcattaa agtagtcggt   46140
cataggagac tttttactt tctgtgaggg gttttaccgt ctttaatatc ctataatcag   46200
ggacattttt tcttttctc cgtgaccccc tgcttttaa aaaattgtgg tgaaatacac   46260
ataacattac atttcaaatt tacctttgta acctttgttt tttttttttt ttttgagac   46320 agtctcactc tgtcacccag gctggagtgc agtggtgtga tcacagctca ctgcagcctc   46380
aaccacctgg gcctagcga tcctcctgcc tcagccttat gagtagctgg gactacaggc   46440
acatgccacc atgcccagct aattttttt ttttttttt ttggtagaga tgggctcttg   46500
ccatgtttcc caggctggtg ttgaactcct gggctcatca actgatgaga aagagctctc   46560
caggcagaaa aagatcatg ttcaaagaca gaaacagaaa tgtgtattct tgggagaagt   46620
gtagaaagtt cagcatctga ttgggtcggg gaagacaagc tagtcaaggc cacatgatgt   46680
tttaattagt catgcctaac agtggggccc tggaagagca gtttaccaca aggggccaac   46740
tgcttcggtt tgaacccgca gccctgccac ttgctctgta accttaagta aacaattttt   46800
actctctctg ttcctccaat gggagtgata acaatacctt cttcatgaaa ttaattcata   46860
catgtaaaat gcttagaaca gtatctgaca cataaatgca aaataattta actgctttct   46920
gctgctgctg acatcactat catcaccctc accattactg taggaaatgg ggacccagtg   46980
aagaattttt tttttttctt ttgagacaga gtctcactct gtcacccagg ccggagtgca   47040
gtgacgcgat ttcggcccac tgcaacctct gcctctcagg ttcaagcgat tctcatgtct   47100
cagcttccca agtagctggg attacaggca tgagccacca cactgggcta atttttttgta   47160 tttttagtga gatagggttt caccatattg gccaggctgg tctcaaactc ctgacctcag   47220
gtgatccatc cacctcggcc tcccaaagtg ctgggattac aggcataagc cactgtgtcc   47280
ggccctagtg aggaatttta agcagaaaac tgatatgctc aggtgtgagc gaggtggtag   47340
gtaacactta ctgtgcagtg ccctgtagcc caagaggtta gcacacaggc atttgctcag   47400
gcagcactag gattttctgc tgtggaaaac ctttgtattt tatcctgctc cacaagataa   47460
aaataagtgg tttaagtcaa tttggataga ggctccaact taccatggga ggtaggaaag   47520
ccaaagttat cccaaggatg ttttcaatcg tacggattag gggtctgcaa actgtgagcg   47580
tggcccaaat ccagcctgct gcttgttttt gtaaatgagg ttttttcgga acccagccac   47640 actcattat ttatgcatta tctgtggctg ctttggtgct gcagtggcag ggctatttgt   47700
ggcagggact gtatgaccca ggaaaccaaa aatatttacc ctctgtccct tagagaaaaa   47760
```

-continued

```
gtttgcaacc cctgatataa agctataagt tggttatttg tggcctcaac ccaggcctca   47820
ctgctatttt ttctgtttac aatacctggc atgctcttaa gtgtctagaa ttggttaaag   47880
atagaagagt ggatgtaatc cctgctacca agggctgtca ggctagttgg gattataagt   47940
acacaaacac tcaaagtgag aaaaacacag aaaaggatgt gtgtcatttt gtctaaggaa   48000
gttgaataag atttctcagg aaaagaaaca tttgaactga atttgaaggt gagtgagttc   48060
aggtgtgttt gggctgaagc ccaggccatg ctgagtggat agcgggtggg aagagagtgt   48120
ggaaacacac tgcatgcagg gaagagttgg gagtctgggg tgaccaaggc acagggaggg   48180
aaagttgaag ttatcaattg tgtgaaacag ctttctgtgt tggcctgaga tgtttatagc   48240
tggaagcagt ggggagccaa tacagttttt tacgaaggta ttagaggtgg gtttctgtgg   48300
gtgatcgtta atcatgtttt ctcccttttaa gtgtagtcct gcttgagaaa tagacatgag   48360
aaaggaatga aggttaaaac atcagctgta ttgttggtaa aactagaatg gaaagtgtgg   48420
cttgagctgg taaccatagg gcttttccaa tgcctgtgcc ctgagttaga tcttggggta   48480
gagagactgg atgtgcagag cagcaccccc acccccaccc cagccatccat atggagcttc   48540
agctgccata gaccaacaag gcagagggat aggcctctag acctgcttct agaaaccagg   48600
ctgctgctct tgcttatggt gggccctagg aaggcaagag tgagaggagg gaggcaccag   48660
cttaggtgct gggttctttg aagatctgtg tgtacacaga gtctttctct ccatcttacc   48720
aatcagatga gtcactgtca ctgtgggaag aagtaggggc atgggtcacc ttcccaaaac   48780
ttctaagaag tttgtattct gtgggcttgg atagggacca tgggaaagga agagaatggt   48840
tgcccataaa actggctgta gtgtggcctc aaacttctgg acttaaatga tcctcccacc   48900
tcagcctccc aagtagctag aactacaggt atatgccacc atgcccagct agttaaaaaa   48960
aaatttttt ttttttttgg ttgagatgag gtctctttct atgttccctg gccggtctc   49020
aaactcccag cctcaagtga tcctcctgcc ttggtttccc aaagtgctag gattataggt   49080
gggagctacc atgcctagcc caagcctgta atttttttt ttttttttg agatggagtt   49140
tcactttgt tgctcaggct ggagtgcatg gcgcagtctt ggctcaccac aacctccacc   49200
tcccgggttc aggcgattct ccttcctcag cctcccgagt agctgggatt acaggcatgc   49260
accaccaagc tcagctaact ttgtattttt agtagagatg ggtttctccg tgtcggtcag   49320
gctggtctca aactcctgac ctcaggtaat ctgcccacct tggcctccca aagtgctggg   49380
attacaggca tcagccaccg cacctggcac gaacctgtaa ttttaagtt tcatatgcta   49440
tttattttt gttatttctt taattcattc attcatttat tcattcgaga tggggcctca   49500
ctatgttgac taggctagtt ttgaactcct ggcctcaagc agtcctccca cttcagcctt   49560
cccaagtgct gatattatag gtgtgagctg ctacatccag ccttctttct tctttttctt   49620
tttccatgtg ctatttgaca ttttccaagg taccagcctc cccttctccc caagataata   49680
tcttttaata tggaatttca tccctagggc aggactttt ttttattatc cctcagaaat   49740
atactggaca ccacgtttaa gtagacatcc aacatctgct gtcataaatt gttttgaatt   49800
ttttgacata cttgcccatg aggttttga aggcatagac catgtcttag ctgaacatgt   49860
ggtctcttag tgccataaag ggggtttatg gtatgacctg tgtagtgtca cctgtgtagt   49920
gacagcacca ctgcctctgt ttcccttcct cttgtgatgg cagcagcgtc tcaagccaaa   49980
caagaagggt agttagggtg ggatggaagc tgggtagagg tattcctctc cccatagttc   50040
tgtgttcaca tgtgcattga cctccttttt ggcagcaagg gggccaggcc aaccacccca   50100
cagcagccgt ggtgacggag aagcagcaga tgctggagca gcaccttcag gatgtccgga   50160
```

```
agagagtgca ggtgatgcaa gttacaagcc tcgggcaggg agctttcatt aattttttt    50220
ttttttttg  acacagggtc ttgctctgcc actcaggctg ggctgcagtg gcatgatcac    50280
agctcactgc agcctcgacc tctcaggccc aagcgatcct cctacctcat cctcccaagt    50340
agccgggacc acaggcatgc accaccacgc ccagctaatt aaaaaaaaaa aatttgtaga    50400
gatggggtc  tccctgtgtt gtccaggctg atcatgaact cctgggctca agtgatcctc    50460
ccaactcagc ctctcaaagt gctggcatta caggcgtgag ccactgcacc tggccaacag    50520
ggagccttct cttggggata ctgcctgcag gtcctgcatg tatcttttt  gaggttttgg    50580
cttcatttga attctcctca gaaactttat attttctgtt cccaaggaaa tctttctta     50640
cttctgtttt tttgtttgct tattttaaac aggatctaga acagaaaatg aaagtggtag    50700
agaatctcca ggatgacttt gatttcaact ataaaaccct caagagtcaa ggaggcaagt    50760
gaatattaga gatgttaaaa tctctagaaa gtgagtttgt gttgttgagt tgaaagactc    50820
atttgtctta actctgttta gatcttaagg cgggcgggc  gcaagggagg tacgggtcct    50880
caaaggagcc tggtcattaa ggacaggagt attccctcag gtccaggagt attccctcag    50940
gtccaggagt attccctcag gtcaaggagt attccctcag gtcaaggagt attccctcag    51000
gtccaggagt attccctcag gtccaggagt attccctcag gtccaggagt attccctcag    51060
gtccaggagt attccctcag gtccaggagt attccctcag gtcaaggagt attccctcag    51120
gtccaggagt attccctcag gtccaggagt attccctcag gtccaggagt attccctcag    51180
gtccaggagt attccctcag gtccaggagt attccctcag gtcaaggagt attccctcag    51240
gtccaggagt attccctcag gtccaggagt attccctcag gtccaggagt attccctcag    51300
gtcaaggagt attccctcag gtccaggagt attccctcag gtccaggagt attccctcag    51360
gtccaggagt attccctcag gtccaggagt attccctcag gtccaggagt attccctcag    51420
gtccaggagt attccctcag gtccaggagt attccctcag gtccaggagt attccctcag    51480
gtcaaggagt attccctcag gtccaggagt attccctcag gtccaggagt attccctcag    51540
gtccaggagt attccctcag gtcaaggagt attccctcag gtcaaggagt attccctcag    51600
gtcaaggagt ttttcttcc  ttcgcagaca tgcaagatct gaatggaaac aaccagtcag    51660
tgaccaggca gaagatgcag cagctggaac agatgctcac tgcgctggac cagatgcgga    51720
gagtaagggc ataggtcgga ccacttcccc catgtgtctc gctcacttgc gggatttcag    51780
cgtcttgtgg cagaacttgc ttggtttcta agaagttcct gctctggagt tgactaaaga    51840
atgtggttag agacagtctg aggaaatgtt ttctgacttt gttttggttt ccaaccagag    51900
catcgtgagt gagctggcgg ggcttttgtc agcgatggag tacgtgcaga aaactctcac    51960
ggacgaggag ctggctgact ggaagaggcg gcaacagatt gcctgcattg gaggcccgcc    52020
caacatctgc ctagatcggc tagaaaactg gtaaaggatg aaagaagctt tccttttctt    52080
tctcgaaagc tagattgaat tctgatctta actgcaggcc cacagaattg gtactatatc    52140
tccaacgtgg ggacttttcc atattcaaat ttagcccaag aattaaagtt tttactttat    52200
ttcggccagg cgctgtggct cacacctgta atcccagcac tttgggagac caagatgggc    52260
ggatcacttg aggtcaggag tttgagacca gcctggccaa catggtgaaa acacatctct    52320
actaaaaaca taaaaaaatt agccgggcgt ggtggtgcgc acctgtagtc ccagctactc    52380
tgggcggctg aggcaggaga atcacttgaa cctgggatat ggaagttgca gtgagcgag    52440
atcttactac cgcacaccaa ccagcctggg agacagagtg agactccatc tcaaaaaaat    52500
```

```
aaaaataaaa taaagttttt actttatttg gagaaacttt gttttaaaaa atgtatttat    52560
attattatat tttaagtata ttttacttaa taattcaatt aaggcttttg gtttaactgt    52620
atttaacaga tagacaaacc ttttaatttt agttatttta gtaatctaaa atgacacatg    52680
ccctttttaa gggaaaaaat tcaaatacag aaaattaatc aagagaagaa aaaattttta    52740
aatgaaatca tcagcagtac tagtagttaa aatttagttg atgctcaatc tagacatctg    52800
tcattatgta tatacacatt atgtatatac acataaagat agaaatttat acagtttata    52860
ttaggatcat tttttttttct tttttttggag tcagggtctc actgtgttac ccagtctaga    52920
gtacagttat gcagtcatgg ctcactggag ccttgacctc ctgggctcag gcagtcttcc    52980
caccttagcc ttctcagtag ctgggactac aggcatgcac caccacacct ggctaatttt    53040 taaattttt atagacacag ggtcttactt tgttgcctgg gctggtctca aattcctggg    53100
ctcaagggat catcccactt cggcctctca aaagctctgg aattatagat gtgagctgcc    53160
gtgcccagcc caggatcttc ctttatatgc ttttctgtaa tttgcacttt taccttcatc    53220
cagcatatct tactgcaacc cttcctgtgc aaggccctat agtgagcatg ttgcaccagc    53280
ttgccttagg agaaacttga gatacagagc ctgcactgga aatttagcgc aactctacat    53340
gagaatgcct gtctattcat atcctcacta accctgagtg ttgttaattt actgaaagca    53400
gttttaaatg cttcctgacc agggaacgaa gaagcttaag ttctgggaat ggaggatag    53460 aagtgccaga aaagagctca ggagttcaga aatccctgca gcggtccccc tccctctcct    53520
ttcactttct gtctttctgg tcttttggtc tttgttacac tagtgataaa ccatcaaaga    53580
atgatggaat gatgctaact tctctcttt tttaattttt ttgagacaga gtctcactct    53640
gtcacccagg ttagagtgca gtggcatgat cttggcttac tgcaacctcc tcctcccagg    53700
ttcaagcgat tcttagtcac aaccttccaa gtagctggga ttacaggccc atgccaccat    53760
gcctggctat ttttttgtat tttagtagat cgacctgcct cggcctctca aattttttggg    53820 attacaggtg tcagccactg cacctggcct aatatctcta ttcttggaga tagatttaat    53880 gagcttttc tccctctcta ttcacttatt ccttgtgcat gttatcaata ttttgaaaca    53940
taatgtcatg tccttttgatc agttgaaggc tgacattgaa aaggcttatg gggattgggt    54000
gttgtggctc acgcctgtaa atcccaatgc tttgggaggc agagtcggga ggatcacttg    54060
aacccaggag tttgagacca gcctgggcaa caaagtgaga tcccatccct acaaaaattt    54120
aaaaaactag acatgtgcca ttacacttca gcctgggtga cagagtgaga ctccatctca    54180
aaaaactaaa ctaaactaaa caggcatggt ggcacacacc tatagttcta gctactcagg    54240
aagctgaggt aggaggatca ctcatgtcca ggagttggag gaggcagtga gctatgatca    54300
tgccattgca ctgcactagg ccacagagtg ggaccctgtc tcaaaaaaa aaaagaaag    54360 aaagaaaaga aagggctcat gtagttcaag cccttctctt catgcaaggg gatgctaagg    54420
cccatgatgg tgaagggcct ggcaaagctt gcacagatag tgtgtgacag agctggctca    54480
aacccatctt tgggagctgt ctaatctctt tttctgagtc tttatgttca tagacaagtt    54540
aggatgagta aagtaagtgc taaattccat atttcgtgtt ctgcatatct gggctcagat    54600
gcttgtcatt ttccagtgat aactccatca atgcctccta gtggtataaa ttttaatact    54660
tcttgtgtgc ccagccccct cttagaaatt tgagatttta ggaagggact agtaataaaa    54720
ggtaaaataa attattttct ggccaggcat ggtggctcac acctgtaatg ccagtacttc    54780
gggaggtcga ggcagatgga tcacctgagg tcaggagttc aagaccagcc tggccaacaa    54840
ggcaaaatcc catctctact aaaaatgcaa aaattatccg ggagtggtgg tgggtgcctg    54900
```

```
taatcccagc tacttgggag gctgaggcag gagaatcact tgaacttggg aggcggaggt    54960
tgcagtgagc tgagactgtg ccactgcact ccagcctggg caacagagta agactctatc    55020
tcaaaaaaaa aaaaaaaaaa aaaaaggcca ggcgcagtgg cttacacctg taatctctca    55080
ggaggctcag gcaggagaat cacttgaacc cgggaaatgg aggttgcagt gagccgagat    55140
tgcaccactg cactccagct caaaaaataa ataaataaat aaattatttt ctttttttat    55200 ttatttttc agcatccacc caacatggtg aaaaattcct cttttcttaa tgtcactgaa     55260
ctgtaaactt aagatgaaaa attgtaaatt tcatgctata tatatttcac cacaataaaa    55320
aaattccttg ttcttattgt agtggtctcc atgtcttcag tatttccttc cccttctcca    55380
tctcacctgt atacattcac tttggtaatt agcatctttc ttaatttatt ggcaggataa    55440
cgtcattagc agaatctcaa cttcagaccc gtcaacaaat taagaaactg gaggagttgc    55500
agcaaaaagt ttcctacaaa ggggaccccca ttgtacagca ccggccgatg ctggaggaga   55560
gaatcgtgga gctgtttaga aacttaatga aaaggtaatt tagcatcctt gtccctttcc    55620
ctcatctaaa aaatacctaa agactcacgt ggtagagtga gaggcgggct gacttctggt    55680
catggccgtg gcgcgtgagc ccatcttctc tttcctcagt gcctttgtgg tggagcggca    55740
gccctgcatg cccatgcatc ctgaccggcc cctcgtcatc aagaccggcg tccagttcac    55800
tactaaagtc aggtaggcca tgccacttcc atttccagta gagattttac tgagggacac    55860
tgttagggtg agggtagagt tggtggccag ggtcattctt tccaggtgtg gtgtcacagg    55920
cagtacactg ttgcggggtt gaaatttgtt gccatactat ctgcttgctc tctgattctg    55980
atgtcaaaag caaagagca gtcatctttt tgaaggtacc tgggcatatt cctatgattg     56040
tagacctgga gtctcaggcc acagcttctc cttctgccca agggacaaaa taatgtcatc    56100
tattttctgt tctttgaggc tactcttccc tgtggatttt aagggaaaga gtaaggctta    56160
gtgatgggga agctgagagg ccccagggca ggtgggtggt gggcctgtag ggtgaggtgt    56220
tactttcaca ctcaagtcag aacaggtgtg ctggggttt gaccttctgc agcaaaattt     56280
ccctcctcag aaacttagta tggtgttcgg tttcaggatt aatagaacaa atgccagct    56340 gcacagcatg tgttcctgta atattttca ttatatggct ttgattatcc ttttgtgaat     56400
ctctcacaac tttaagttgt tagttcttag atgttttctc agtacctttg cttgaagga    56460 gtgatactca tcttttgttt ttgtttgaga cagggtctca ctctcaccca ggctggtgtg    56520
cagtggcatg atctcagctc actgcaacct ccatctccca ggttcaagtg attcttgtgc    56580
ctcagcctcc tgagtaactg ggaatagagg tgcgtgccac cacacccggc taattttttt    56640 tttttgaga cagagtctcg ctctttcggc caggccagag tgcgtgttgc aatctcaact    56700
cactgcaacc tccacctccc aggttcaagc gattctcctg ccttagcctc cctgagtagc    56760
tggaccggca cactccacca tgcccggcta atttttgtat ttttagtaga cagggttt     56820 ctccatgttg gccaggctgg tctcaaaact cctgacctca gtaatccacc caccccggcc    56880
tccaaaagtg ctgggattac agatgtgagc caccacgctc ggcctttttt tttttttttt    56940
tttttttgag atggagtctt tctctatcac ccaggctaga gtgctgaggt gtgatctcgg    57000
atcactgcag cctctgcctc ctgggttcaa gtgattctcc tgcctcagcc tcccaagtag    57060
ctgggattac aggtacctgc caccatgccc ggctgatttt tgtatttta gtagagacgg    57120 ggtttcacca tcttggccag gctggtctcg aactcctgac cttgtgatcc acctgccttg    57180
gcctcccaaa gtgctgggat tacaggtgtg agtcaccgca cccagcccta ttttaatttt    57240
```

```
tttaaagaga gagatagggg ccaggcacgg tggctctcgc ctgtaatccc agcactttgg    57300
gaggccaagg tggtggatc acctgaggtc gggagttcga gaccatcctg accaacatgg    57360
agaaactctg tctctactaa aaatacaaaa ttagctgagc gtggtggcgc gcgcctgtaa    57420
tcccagctac ttgagaggct gaggcaggag aatcacttga acccaggagg cggaggttgc    57480
ggtgaacgga gattgcgcca ttgcactcca gcctgggtaa cgagagaaac tgtctcaaaa    57540
aaaaaaaaag agaaagagag ataggatctc gctctgtcat ctaggctaga gtgcagtggc    57600
atgatcatag atcactgtag ccttgaactc ctgggcacaa gtgatcctct tgcctcagcc    57660
tcccgagtaa ctgcgactac aggtacatgc taccacaccc cgctaatttt taaattttt    57720 atagatgtgg gctctcactt tgttgcccag actgttatgg aactcctggg ctcaagggat    57780
cctcccagct tggcctccca cagtgctgag attatagatg tgagcctgta attatagaca    57840
gcttggccta tttacctgtt ggaaatgaag aattatgaat tttacatttc ttcaagaaaa    57900
ggttatggga gagttactga ctttttttcc ttggattttt tctttttaaa taggttgctg    57960
gtcaaattcc ctgagttgaa ttatcagctt aaaattaaag tgtgcattga caagtaagta    58020
ctcctatctt agctctgttt ttcaaatgag aatagaaaa atgagaactt tgacagacat    58080
catttgaact agagactctg tctttattca gagatcttca ttttgtggac aaaagttttc    58140
aaaagccttg gggtgcattg tcatttacgt gtctgaacaa agccacaaag ctgggggtac    58200
agatttgatt tgtggttgct attgtgacaa ccagtccctc ttttccttgt ttagtttttt    58260
acttgtacat gtcattcatg catattatat ataagactga gatcatgtgt taattaacga    58320
ctgggatacg ttctgcaaaa tgtatcatta ggcaattttg ttgtgcaaat gttgtagagt    58380
atatagtcct tacacaaacc tgggtggcag aacctactgc acacctacgc tatgtggcag    58440
agcctactgg tcgtaggctg taaacctgta cagtatgtta ctgtgctgaa taccgtaggc    58500
aattgtaaca catctcaatg aagtaggaat ttttcagctc catgataatc ttatgggacc    58560
accatcatat atgcatttg ttgttgaccg aaacgtcgtt atatattctt tccatacata    58620
gcatgtggaa agaatagatc tcttttttt aattgttcca cactttacca tataatggaa    58680
tacgcaaaat ttcacaatac ctttcaggat gtaaaataca tataccctt gacgacatta    58740 gaaagagaa aatgtgggcc gggcgcggtg gctcatgcct gtaatcccag cactttggga    58800
ggccgaggcg ggcggatcac gaggtcagga gatcgagacc atcctgggta acacggtgaa    58860 acccgtctc tactaaaaat acaaaaaaac tagctgggcg tggtggcggg cacctgtagt    58920
cccagctact caggaggctg aggcaggaga atggcatgaa cctgggaggt ggagtttgca    58980
gtgagccaag atcacaccac tgcactccag cctgggcgac agagactcca tctcaaaaaa    59040 aaaaaaaag aaaagaaaag agaaatgtg gctgggcgcg gtggctcacg cctgtaatct    59100
cagcactttg ggaggctgag gtgggcagat cacctgaggt cgagagttcg aaaccagccc    59160
gaccaacatg gagaaaccttt gtctctacta aaatacaaaa attagccagg tgtgttggcg    59220
catgcccgta atcccagcta cacgggaggc tgaggcagga gaatcacttg aactcaggag    59280
gtggaggttg tggtgagccg agatcacacc attgcactcc agcctgggca caagagcga    59340 aactatctca aaaaaaaaaa aagaaaaaag aaaagataaa atgcattctt attttagtt    59400 gatgtaatta tgtggaaatt tcatgaggat gcactggaaa ataatgaaat aagggagttg    59460
acgaaggtgg taggtttaat aagtacatat gcaatatgaa acataggttc cccttcctat    59520
ggggaggcaa ccaactgtgc ctgctacgca gaggtgttat gttgcgctga tcaactgtaa    59580
ctgaatagtt taaagaaatg cccaggagca cagaggtttt ttcatgacag taaataacag    59640
```

```
gtggtcaaag taggcttttt gaagaaacac agagcctatt ttattaacaa cagtctgtgt   59700
tcttacagag actctgggga cgttgcagct ctcagagggt aagttcagcc tagaggcttc   59760
cttttgttcc gtttaaccta acttcatcct ccggctactt ggtcacctac atagttgatt   59820 gttccctgt gattcagatc ccggaaattt aacattctgg gcacaaacac aaaagtgatg    59880
aacatggaag aatccaacaa cggcagcctc tctgcagaat tcaaacactt ggtatgtggg   59940
aggagctccc cttcacaaag ggcctctggc tgccggagag ggctagggag agcctcacag   60000
gacacctgcc tttttctttt cttacagacc ctgagggagc agagatgtgg gaatgggggc   60060
cgagccaatt gtgatgtaag ttttgttggg gatgaaagac aactgggtg ttttccttga    60120 gggagagagg ggtaaagatc cttcttaatc cccagaatta gaaacatcaa cctgttcttt   60180
cagctgtagt tattccaaaa agtcacttca ggccaaagtg acatgaacag aagttccatg   60240
tgccatggag ctctctggct tggaacattt ccgtgaatat ctgggagttg ctcctcctt    60300 aaggagaagt ggaaagtccc ttgctgagtt gttctccaca cccatgtggt ataaagcagc   60360
tttccacctt gcctggggct ttccaaattc cccatccagc tcctgcggct gaccctgctt   60420
ggctccattt ttagtgccct gtttttctct cccactgagg tgggatagag ggtgtaaaag   60480
caacagattt gagttaaact ttaaaataaa tgaccacctt gcattagctt gcttaggaaa   60540
agagtacata aaataaaatg aacaaacaaa aacccatctt gttctttatc ccccttattt   60600
tctgcttttc attgattcag attattggat tcttattgtc aagaataaac tttaaacaaa   60660
caaacaaaaa aaggtaaatg tgacggaagg ctagttttca gtcatttta aaaattgtga    60720 tgccccgttc ttttttcttac atttgtcccc tgaacaattc ttcctcttta aatgtagca   60780 gtcctagctg ggcgtgctgg ctcacacccc gtactttggg atgccaaggc aggctggtca   60840
cttgaggtca ggagttcaag accagcctgg ccaacatggt gaaagcccgt ctctactaaa   60900
gatacaaaaa ttagctgggt gtggtggtgc acgcctgtag tcccagttac tggggaggct   60960
gaggcatgag aatcgcttga acctgagagg tggagcttgc agtgagccaa gattttgcca   61020
ctgcactcta gcctgggcaa cagagtgaaa ctctgtctca aaaaaataaa taaaataaaa   61080
tgtagcagtc ctttttaaaa atgtggaatt ttacttgaca gtagagtgaa gtagcctgta   61140
tgcaatgata tgggaaaatg tacatgacat attaagaaaa agcaaaatgt aaaataattt   61200
gaatagtatt attagtatat gtgttttaaa aatacactat actcttatgt gtattcatat   61260
gtatattaag aaattctgga ggaatatacc agcagtgcta tgtgtattag tgctgctgtt   61320
ggtatccatg gctattctag actgtctctg tgatatttgc attttaaact gaatatatta   61380
cttttataat cagaaaaata gtattaaaaa tgaattataa tttaatttct ttttctttt    61440 ttttttttga gtcggagtct cgttctatcg gattgcagtg gtgcgatctc agctcactgc   61500
aacctctgcc tcctaggttc aagcgattct cctgtctcag cctcccaagt agctgggacg   61560
ataggtgcat gccaccacgc ctggctaatt tttgcatttt tagtagagac agggtttcac   61620
catattggtc aggctggtct tgaactcctg acctcgtgat ccacccatct cggcctccga   61680
aagtgctggg attacaggca tgagccgctg tgcccagact agaattcaat ttttgagaat   61740
tcattgacaa ctcttactta aaataaggtt gctgtactga tgtgagacat tgttgtagtc   61800
agtttggaaa acaatttggc agtataaaaa tgaacatacc tgtaaaccaa cggtgccatt   61860
cccaggattt aatagcagag aaatctttgc atatatgtcc caggagacat atataaagtg   61920
gacatcagcc tgattataag ctctaaatgc aacccaaata aatacccatc aacattagaa   61980
```

```
tgaatacatt atttgtggta tagacacaat ggaatactcc gcagctgtga aaaggaatac    62040
actgcagata cacataacca tgtggattca tttcacatca agtgaaaagt gaatcccaaa    62100
agaattcatt ggagtccata agtgtaaggt tcacaaatgt cccaaactaa acaatacctg    62160
cattgcttag ataaacaaat atggtaaaac tgtaaaaaaa caaaacaaaa caagacaaaa    62220
agggctagga aatgataaac ccaaaagaca aaatagcagt tatttctgag ggaggaggga    62280
aggggatggg gttggggaag ggcacccaga gaattttagg agtgatggac ttttccttaa    62340
attgaatggt gggttcatat tgttttgtta ttctttgtgc cttacgtatt ttacaaataa    62400
ccaattggat ctatgtaata ttataataca aactgagtaa aggattaggt tgaggatcac    62460
agcattggaa gttcttggtg ttgaagagag taagtgccga gcaagttgtg tccctggcag    62520
tttgtttgtg accacctggt ggcttaccct tcttggtgtg gtgaggcttg gcatgtcact    62580
ttccttggct gtggctgtta gtactgaatg ccattctctc tgaggaaaag tgtccttctc    62640
tttttttattg attgactgat tgattgagac agagtctcac tctgtcaccc aggctggagt    62700
gcagtggcgt gatctcggct cactgcatcc tctgcctcct gggttcaagc gattctcctg    62760
cctcagcctc ctgagtagct gggactacag gcgcccacta ccacacccag ctaattttttg    62820
tattcttagt agaaacgggg tttcaccaaa ttattggcca ggctggtctc gaactcctga    62880
ccatgtgatc cacctgcctc ggcctcccaa aatgctggga ttgtaggtgt gagccatcac    62940
gctcagcctt tttttttatt taatttaatt ttttttttaag acagggtctc actctgtcac    63000
cccagctaga gtgcagtggc acaatcatag ctcgctgcag cctccatctc ctaggctcaa    63060
gccatcctcc cacctcagcc tctcgagtag ctggggctat aggtgtgcac caccacccc    63120
agctaatttt tgtattttttt gcagagatgg agttttgctg tgctgcttag actggtctcg    63180
aactcctggg ctcaggcaat cctcctgcct tggcctccca aagtgctggg attacaggca    63240
tgagccacca cacctggcct aagagtgtcc ttctcgttac tgtaggcttc cctgattgtg    63300
actgaggagc tgcacctgat caccttttgag accgaggtgt atcaccaagg cctcaagatt    63360
gacctagagg taagttctgc agcagaatcg gtgagaggct acgtacaggg gtgactcagg    63420
acaaaaactt ccactgggat ttttacaaga gaaggtggaa tgattactgt ttgcttaaca    63480
ctgtgtttat ttttgcttac ttttctccaa aaaaatcctt ggcatcccat ctggcaataa    63540
agtcttgctt gaatgcttag aagatgtgtg tatattcagc tttcagcaaa cttgatatga    63600
aaatctctat ttagaaattg attggccggg cgcggtggct cacgcctgta atcccagcac    63660
tttgggaggc tgaggcgggt ggatcacgag gtcaggagtt cgagaccagc ctggccaaca    63720
tgacgaaacc ccgtctctac taaaatacaa aaattagctg gtatggtgg cggacgccta    63780
taatcccagc tactcgggag gctgaggcag gagaatcact tgaacctggg aggcagaggt    63840
tgcagtgagc tgagattgtg ccattgcact ccagcctggg tgacagagtg agactccgtc    63900
tcaaaaaaaa aaaaaagaaa ttagaactga ctttataaag tttgggcata agagtcttag    63960
cagccagtgt gtttagtata cagaaaattg tggcaatgac attctccttt cccaactttc    64020
ttgattttta aattaagata tacctagaaa agcaggaatc ctggtctttg attcctgaga    64080
cctcccctgtt tcatgtgaag atacagcttc aagtcttgga gaatgcctcc aaggtcttaa    64140
aaatggggaa tctgtggatt gtgagtcaag ctttgagcaa gtcaggtttt acaagggacc    64200
ggtatattcc gactgcagcc tgagttgtgt ggccacgctg ggcattcttt ccactatgag    64260
tgctcactga gctgactcac tcacactcct cgcctagagt tggcagcagg tgtggtttat    64320
ggcatgtcct ttcattctga gccccgtgag atgcgggtga agagatttcc aaggctgtga    64380
```

```
gagcccctct gcctcccag ctcagtcccc actccctccg cagacccact ccttgccagt    64440
tgtggtgatc tccaacatct gtcagatgcc aaatgcctgg gcgtccatcc tgtggtacaa    64500
catgctgacc aacaatccca aggttagtgc cccctccttt tagttggtgc cccgggatct    64560
cttgcgactt aggggtacct agtatagaca atgagcacca tccctcatct aaacaagcaa    64620
atgtgttctt tccaatagaa tgtaaacttt tttaccaagc ccccaattgg aacctgggat    64680
caagtggccg aggtcctgag ctggcagttc cctccacca ccaagcgagg actgagcatc     64740
gagcagctga ctacactggc agagaaactc ttgggtccgc atttcacccc ttctccctcc    64800
cgcccacccg cccagaaaag ggatccggcc catagggctg ttcatttggg ccatgtctac    64860
tgagcattag gccatgtttc tttcctgagc aaggcgctgt gctggtgcca ggaaacaggg    64920
gagttgggga gttggggtgc agagacagtt tgcagttttc agtcgaggtg atcattttg    64980
aggtgggagg tagatttctt ttctcctggt tgctgtctca ttcacccact ctatctaact    65040
ttagaagatc ttttaagtgt gtgttggaag gtggcactaa aggcttgaca ttccctgtcc    65100
attttttttaa taaactatag gctagttggt ttttttttgtc ttatttttatt tatttattta    65160
tttttttgag acgagtcttg ctctgttgcc caggctggag tgcagtagtg tgatctcggc    65220
tcactgcaac ctccgccttc tgggttcaag cgattcttct gcctcggcct cccgagtagc    65280
tgagactaca ggtgctcacc accacgccca gctaattttt gtattttag tagagacggg     65340
gttttaccat gttggccagg atagtctccg tctcttcacc tcgtgatccg cccacctcgg    65400
cctcctaaag tgctgggatt acaggcttga gccactgtgc ccagcgtagg ctagtttta    65460
aaaaagaatt agtggaatat tttatgtgcc acctgggcta gaagtagctt tgttctaata    65520
aagctgttgc caccaaatac acctgtctga cacccgatgt cagcttgtta gtgagtgctg    65580
ctgttggttc ccagcctacc acccgaggtt gggaagagca gggggacttg ttatatcacc    65640
ctccatccct gctgggctac ccagcaacac aagtgagtca aatgatggga tagtgtttgt    65700
cctcatgtgc acacacacaa cagtgcctac cttcaaagat gtgaaagctg attattttgt    65760
ggcccattgt gggatgaatg tgtgtgtgtt ctgttttaag aaataaccte ttgaccccaa    65820
gctgaaaatg tactacttga ctctttttct tccttcagg acctggtgtg aattattcag     65880
ggtgtcagat cacatgggct aaattttgca aagtaagcaa tcttgttaaa ttctcgtggg    65940
aatgggaatg ctcacctgca cggctgtcgt tgagggctct ggcttgaagg ccctgaactc    66000
ttggtccagc ggccagtagg acctgcctga aggtagacgg gcctgaggat ttgggtgatg    66060
cactgcaccc ctaggaaggg aagggctggg atggcagtag acttggcttt cccattactc    66120
ttttctccag gaaaacatgg ctggcaaggg cttctccttc tgggtctggc tggacaatat    66180
cattgacctt gtgaaaaagt acatcctggc cctttggaac gaagggtagg ttggacagag    66240
tgtgcacaga tgtaaccaag tcccctgctc tcagcaagcc agtggcaggg gatggatgcc    66300
ctgttagcaa taacaacatt gttcctcctc cttggctcca ggtacatcat gggctttatc    66360
agtaaggagc gggagcgggc catcttgagc actaagcctc caggcacctt cctgctaaga    66420
ttcagtgaaa gcagcaaaga aggaggcgtc actttcactt gggtggagaa ggacatcagc    66480
ggtaagggag gctcccaccc accccacctg ctggtggctc ctgaggcctc atcactgctt    66540
ctagttgcaa gcacctactg ccccctggtg ggtggagatg gccttgactc cctgtttcac    66600
tcagactcgc aaaacacatt tgcgtgactt ctaaatcctt ccagctgaag gattggtttg    66660
ctttgttttg cttgctccag tgactatttg ttgagaattt tgcaatttaa attgtattct    66720
```

| | |
|---|---|
| tcatctcttt ttctacttaa ccctgttaat atatcttacg caagtagtta tattcaagtt | 66780 |
| tattttctat gacccaacta gtagcctctt cttaattaga agccagcctg aatatttcca | 66840 |
| cagtgccagg ccactgaaca gggtgttcag ggtctcaaca ctagggtggc ttaagtcttt | 66900 |
| tccccttcga ggaaagaaaa aatgggcagt tttctctgag atgacctagc tgtaggttcc | 66960 |
| atgatctttc cttcccatgt cctgtgacag gtaagaccca gatccagtcc gtggaaccat | 67020 |
| acacaaagca gcagctgaac aacatgtcat ttgctgaaat catcatgggc tataagatca | 67080 |
| tggatgctac caatatcctg gtgtctccac tggtctatct ctatcctgac attcccaagg | 67140 |
| aggaggcatt cggaaagtat tgtcggccag agagccagga gcatcctgaa gctgacccag | 67200 |
| gtagttgttg attttccatg ttcctggcat ttaattttg ggaaaagttg gaaattttgg | 67260 |
| gatccttgga ggatagatag gcaaatgcct gaataacctg ggggataatt atttctcctt | 67320 |
| atgggaaaga attgtagtga gtgcttttgt tggggtgacc gatgggattt gagaggagaa | 67380 |
| tcagaatcac ttagagtagt gtagttcctg ctccacagag agtgcatgag tctaaagagg | 67440 |
| ggatacagcc tgggcaatat ggtgaaacct cgtctctaca aaaaatccaa aaaaattacc | 67500 |
| cggtgtggtg gcacgcattt gtagtcgtag ctacttggga ggctgaggtg ggaggatcac | 67560 |
| ctgagccaag gagttcaagg ctgtagtgag cggtgatcat gccaccgcac tccagcctgg | 67620 |
| ctgatagagt gagatactgt gtcaaaaaat aaaataaag aggggatcaa tacacatacg | 67680 |
| tcccccaaaa catgcctgaa acacgagaag ggaaagtgag ggcagttaac aggatgccct | 67740 |
| gctggcacag tgcttcttag tagatgctag aaggtttgag gcccagatttt cagcccagca | 67800 |
| tatgccttt tgcctgtaac tgaaccatgt cagtgtgcca gatggtctga agaaagggtt | 67860 |
| tctggaggaa attattatta gctgcatggg agtatggttt acactagagt agaagagctg | 67920 |
| ggagcatcac gtttgaaggg gaagacagtg actgggtgga ggggcaaggg attagtattt | 67980 |
| agagtgtgca actattgaaa ataaggtata ttttaatgtg taagaggaca tgtacttata | 68040 |
| tgttatatat aaattatttt agctgggtga agtggctcat gcctatagtc ctagcacttt | 68100 |
| gggaggccca ggcgggagga tcacttgagc ctgggagttt gagaacagcc tagacaacat | 68160 |
| agtgagaccc tatctataca aaaataattt ttttaaatt agccacgtgt ggtggtttgt | 68220 |
| gcctgtagtc ctagctactc gggaggctga ggtgggagga ttgcttaagc ccaggaggtt | 68280 |
| gaggctgcag tgagccatga tcgcaccact gcactccagc ctgggtgaca gagcaagacc | 68340 |
| ttgactcacc aaaaaaaaaa aaaaaaaaa gagagagaaa ttaaaaatac tgtaatctca | 68400 |
| gctgggcatg ggggttcaca cctgcagtcc tagcactttg ggaggctgaa gcaggaggat | 68460 |
| cacttgaggc caggaactca agaccagcct ggcaacatag caagacccca ctacacacac | 68520 |
| acacacacac acacaaaag aagagaaaga aaaaacgaa acaaaactgt aatctctgca | 68580 |
| gctgtcctca gtgtggaggg ggtagccctg tctgttcccc ttcagcactt gctgttttga | 68640 |
| ctctctgggt tctttgtgca ggtcttgatg gggagtctct ggtttgccat tctttgtttg | 68700 |
| atttaacttt ctgtaatcat aaagccaatg atgggctttt ttttttttt ttttttaga | 68760 |
| ctaagtcttg ctctatcacc caagctggag tgcagtggca ccatctcggc tcactgcaac | 68820 |
| ctccacctcc cggttcaagc aattctcctg cctcagcctc ccgagtagct gggattatgg | 68880 |
| gcttgtgcca ccatgcccag ctgattttg tattttttgt agagaaaggg tttcgccatg | 68940 |
| ttggccaggc tggcctcgaa ctcctgacct caggtgatct gcccacttca gcctcccaaa | 69000 |
| gtgctgggat tacaggcgtg agccactgtg cctggcctaa tgatgggctc tttaatgtga | 69060 |
| tcctttaggg ttggcgcctt gccctagttg ctgttgaaaa aactattttt gtccaaatag | 69120 |

```
cacacacaca gaaacctacc aacttccctc ccacttttc ctaggaattc cttctgaggg    69180
atttcttgag atggggcaga atggggcttg gaagagggag ttggagctaa ttgaccgttg    69240
cctttctcct ttgttggggt cctgagtctt gttcctgctg taagagttac tcacttcctg    69300
tctgccacct atctccctt gcatgtgtgc ttcagttggg agatctgttt atcagcccct    69360
gccacacggc tctttgttcc ttctgcagag gacgttgggg tcccacggct ggtccttttg    69420
actcattttg ctttcaaggt cccacctccc agtctgaggc tgcatcctcc attaccatcg    69480
cccttcctgt gggctgggag gccaggtcct ttcctgccca gcgatgtcag cgtttcctca    69540
ggggccaggc actcatcagg agaaaggaac taattacttg agtaatttgc cttgccttgc    69600
tgagaggagt gtgccctgag ggactccatg tgagtgtggt gacgggtgtg ggggtgtccc    69660
tgtgttattt taaaatgggt gccttcagga cgatgagcat gtgaccattt cctctctatt    69720
tccatcacaa gagtattatg gtatgagggt ctcaggttag attatcctcc caagactctt    69780
ctctcttcct tctctactgg aagcccacat agcatttcct tatggcttga gggagaggtt    69840
cggagccact tacaaattag ataaagtaca tttacaatct tgtacaaagc cacacaatga    69900
agtcattttt ctcagctttt ttttttttt tttttttt tttgagcctg agtctcgctc    69960
tatcgtccag actggagtgc agtggcgcga tcttgcttca ctgaaacctc tgcctcccag    70020
gttcaagaga ttctcatacc tcagcctcct gagtagctgg gattacagac atgcaccact    70080
atgcctggct aatttttgga tttttagtag agaccggggt tcaccctgtt ggccaggctg    70140
gtctcgaacc cctgacctca agtgatcttc ccgcctgggc ctcccaaagt gctgggatta    70200
taggtgtgag ccacagtgcc cagccttgtt tttgtttttg ttttgttttg acagtctgtc    70260
actctgtcac ccaggctgga gtgcagtggt gcgatctcac ctcacttcag cctctgcctc    70320
ccaggttcaa gtgattctcc tgtctcagcc tcctgagtag ctgggattac aggcgtgcca    70380
ccacgcccag ctattttgt aatttcatta aagacagggt ttccccatgt tggtgaggct    70440
ggtcttgaac tcctggcctc aagtgatcca cctgcttcag cctcccaaag tgcagggatt    70500
acaggcatga gccactgtgc ctggcctcag ctatcttgaa tgctggagaa ttaaatcctt    70560
ttctgtctag ggtgtcagct ccctaagggc tgggccaaaa cagttggatt tataagacac    70620
tagagtcttg cctcagtagc tccttgaat tctgcactga attgatcagt ttcttggccc    70680
aaagtaaact cagatggcag cccaagagcc actctgcagt gccttctttc acatggtcat    70740
catgctctct gatccctcag gttctgtcta agcctcatgt tttatgaccg tgctgttctc    70800
agcccacctc accctgcccc atgccttctc aatggtttgt tcacctgaat tccccagatt    70860
tcatgccagt atccccaagg ttccttgacc tcttggtgta agcattcagc atctaaaatt    70920 catttattc ccgtcaacgc atttctaact gtagaacaag aattataaat gacaaagctc    70980
atagaaaatt ggcaccttgt cttcccctc cctcttattt tatacataaa agagaatatg    71040
ggctgggcat tgtggccaag gctgggcatg atagctcata cttgtaatcc agcactttgg    71100
gagggtgagg cagatggatc acctgaggtc aggagttcaa gaccagcctg ccaacatgg    71160 tgaaacctca tctctactaa aattacaaaa aaaaattag ctaggcatgg tggcagatgc    71220
ctgtaatcca gctactcagg aggctgatga aggagaatca cttgaaccct ggaggcagag    71280
gttgtagaga gccaagatgg cgctactgca ctccaacctg ggcgaaagag agcaagactc    71340
cgtctcaaaa aaaaaaaga caaaattag ccaggcatgg tggtgccacc tgtagtccca    71400
gctgcttggg agcctaaggc aggagaatcg ttttgacctg ggagtaggag gttgcggtaa    71460
```

```
ccgagattgt gccactgcac ttgagcctgg gcaacagagt gagactctgt ctcaaaacaa    71520
taagaacaac agcaacaaaa gagagagacc atgccttgct ccaggtctct tagctattga    71580
agatgtacct ggacccaggt ctccggtctt ctagttgaag caattgtact gccttacaaa    71640
gtcacattct ctttggtgct ttttgattga cgtatttatc caactagaaa gttactcatg    71700
ccctcatcca aaaatgtggt agaggccaga ttagtgctgg taggaataag agatataacc    71760
tttggctttg gaaccacaag cattagcagt ctccatgttc tttaaagact tggtgatatt    71820
ggtatttagg ctggacacca tgcaaagact acacaggctc ggttcctgca tgcagagaag    71880
ttatctaaga gatatgacca ggccggaata gaatgctcag accacgtgga ggctgttaaa    71940
cttttacata atctagggaa agaagggaca caaggtggca ttagtctagg gtcaggtggg    72000
aaaaggttat gctgaaaagt ctctgcagct caggacagct ttgtgcaaag aactgaagtt    72060
cacagctgct agtgcctggg agatcaaata gtataaatga gggcagacaa ccctgagggg    72120
cagatggagc tttccagaca atcttggcat gaggatgagt gagtttcaaa tcagtcctgc    72180
cgaggcagat ggcttcctcc agctctgctt actgaatgcg aagtcacagt cagtaagaaa    72240
actggttttc ttcttcccag gcgctgcccc atacctgaag accaagttta tctgtgtgac    72300
accgtaagtg gcttcctttc cccgttttgc cttcatttct aatatcctca gttatccctg    72360
ggaatgggac actgggtgag agttaatctg ccaaaggttg gaagcccctg ggctatgttt    72420
agtactcaaa gtgaccttgt gtgtttaaaa agcttgagct tttatttttc tgttggagac    72480
cagagtttga tggcttgtgt gtgtgtgttt tgttctttt ttttttttcca ttgtgtcttg    72540 tcaacccccc gtttcccctc ctgctgcccc ccatttccta cagaacgacc tgcagcaata    72600
ccattgacct gccgatgtcc ccccgcactt tagattcatt gatgcagttt ggaaataatg    72660
gtgaaggtgc tgaaccctca gcaggagggc agtttggtga gtatttggtt gacagacttt    72720
gtccctataa gggaagttgg tccccttgt gtgatgctct cacatgtaca caccgagagc    72780
tggtcactcg gaatggtagg agattctaga gctttgcttt ccaaaagaga tggtatgaat    72840
gccacatgtg tgagtataaa tcttctagca gccacactgg aaatagacga acttaatttt    72900
tacaatatat tttatttaac ccactaaatc caacatactc tcaatttaac atttcagaaa    72960
aagttgaggc tgggtgagtg gctcatgcct gtaatcccag cactttggga ggccgaggtg    73020
ggtggatcac ttgaggtcag gagttcgaga ccagtctgac caaaatctct aaaatataaa    73080
aattagctgg gcatggtggc gcatacctgt aatcccagct actcaagaag ctgaggtggg    73140
aggatcgctt gagcctggga ggtggaggtt gcagtgagca gagatcgtgc cactgcactc    73200
cagcctgggc gacagagtga gactccatct caaataaaca aaactaaact aaaaagaaaa    73260
agttgagacc ttttttttatt ctttttttc atactaagcc tttaaaatcc agtgggcttt    73320
tgacagccac agcacagctc agtttggaca aaccaaatct caaatgcttg gtggccacgt    73380
gtgtctcggg gctcctgaat taaacagtag atcaagggca gaagatctca ggacagcctt    73440
agagcttctg taaacatgga gctctgggaa tcagttaagg tgggaatgag aaaggaccct    73500
tcccgaggca gggtcctcca gggaggaggg taaatctggc ttttctgacc atccctgggc    73560
cttaaggggc aggagattgg atagcagtgg tagcctgggc cctgtcctct gaagggctgg    73620
gggcgtggcc tgccagttgc agagggtgga caactgaact agttttccct gtctgtccct    73680
ccagagtccc tcacctttga catggagttg acctcggagt gcgctacctc ccccatgtga    73740
ggagctgaga acggaagctg cagaaagata cgactgaggc gcctacctgc attctgccac    73800
ccctcacaca gccaaacccc agatcatctg aaactactaa cttttgtggtt ccagattttt    73860
```

```
tttaatctcc tacttctgct atctttgagc aatctgggca cttttaaaaa tagagaaatg   73920
agtgaatgtg ggtgatctgc ttttatctaa atgcaaataa ggatgtgttc tctgagaccc   73980
atgatcaggg gatgtggcgg ggggtggcta gagggagaaa aaggaaatgt cttgtgttgt   74040
tttgttcccc tgccctcctt tctcagcagc ttttgttat tgttgttgtt gttcttagac     74100
aagtgcctcc tggtgcctgc ggcatccttc tgcctgtttc tgtaagcaaa tgccacaggc   74160
cacctatagc tacatactcc tggcattgca cttttaacc ttgctgacat ccaaatagaa      74220
gataggacta tctaagccct aggtttcttt ttaaattaag aaataataac aattaaaggg   74280
caaaaaacac tgtatcagca tagcctttct gtatttaaga aacttaagca gccgggcatg   74340
gtggctcacg cctgtaatcc cagcactttg ggaggccgag gcggatcata aggtcaggag   74400
atcaagacca tcctggctaa cacggtgaaa ccccgtctct actaaaagta caaaaaatta   74460
gctgggtgtg gtggtgggcg cctgtagtcc cagctactcg ggaggctgag gcaggagaat   74520
cgcttgaacc tgagaggcgg aggttgcagt gagccaaaat tgcaccactg cacactgcac   74580
tccatcctgg gcgacagtct gagactctgt ctcaaaaaaa aaaaaaaaa aaagaaactt    74640 cagtaacag cctccttggt gctttaagca ttcagcttcc ttcaggctgg taatttatat     74700
aatccctgaa acgggcttca ggtcaaaccc ttaagacatc tgaagctgca acctggcctt   74760
tggtgttgaa ataggaaggt ttaaggagaa tctaagcatt ttagactttt ttttataaat   74820
agacttattt tcctttgtaa tgtattggcc ttttagtgag taaggctggg cagagggtgc   74880
ttacaacctt gactcccttt ctccctggac ttgatctgct gtttcagagg ctaggttgtt   74940
tctgtgggtg ccttatcagg gctgggatac ttctgattct ggcttccttc ctgccccacc   75000
ctcccgaccc cagtcccct gatcctgcta gaggcatgtc tccttgcgtg tctaaaggtc     75060
cctcatcctg tttgttttag gaatcctggt ctcaggacct catggaagaa gaggggggaga   75120 gagttacagg ttggacatga tgcacactat ggggccccag cgacgtgtct ggttgagctc   75180
agggaatatg gttcttagcc agtttcttgg tgatatccag tggcacttgt aatggcgtct   75240
tcattcagtt catgcagggc aaaggcttac tgataaactt gagtctgccc tcgtatgagg   75300
gtgtatacct ggcctccctc tgaggctggt gactcctccc tgctggggcc ccacaggtga   75360
ggcagaacag ctagagggcc tccccgcctg cccgccttgg ctggctagct cgcctctcct   75420
gtgcgtatgg gaacacctag cacgtgctgg atgggctgcc tctgactcag aggcatggcc   75480
ggatttggca actcaaaacc accttgcctc agctgatcag agtttctgtg gaattctgtt    75540
tgttaaatca aattagctgg tctctgaatt aaggggggaga cgaccttctc taagatgaac   75600
agggttcgcc ccagtcctcc tgcctggaga cagttgatgt gtcatgcaga gctcttactt   75660
ctccagcaac actcttcagt acataataag cttaactgat aaacagaata tttagaaagg   75720
tgagacttgg gcttaccatt gggtttaaat catagggacc tagggcgagg gttcagggct   75780
tctctggagc agatattgtc aagttcatgg ccttaggtag catgtatctg gtcttaactc    75840
tgattgtagc aaaagttctg agaggagctg agccctgttg tgcccatta aagaacaggg    75900 tcctcaggcc ctgcccgctt cctgtccact gccccctccc catccccagc ccagccgagg   75960
gaatcccgtg ggttgcttac ctacctataa ggtggtttat aagctgctgt cctgccact    76020 gcattcaaat tccaatgtgt acttcatagt gtaaaaattt atattattgt gaggttttt     76080 gtcttttttt ttttttttt ttttggtat attgctgtat ctactttaac ttccagaaat      76140
aaacgttata taggaaccgt ctgatagcat ggcagctctg tttggctggt ggaggcttcc   76200
```

```
tttcccctg cataagttct gaggggggcct cacacacagg tggggcctgg gataagggcc    76260
ggaaagggtc ttgagaggag gtggttgcct taatccccc cgccaacccc cttatgttag     76320
ccaccagccc ggaggtaagg ggtgcctgga ggagcaggag gtcaatagtc caacggcaga    76380
aaggtgtcag agtggaggcc tccctcccg gcccctcct acccccaga gcggcctcgt       76440 cctgtctggg gtcagataag ccacctaagc ggggtggggg gtagatactc ccaccgcacc   76500
aaggcctccc cttccacagt tggctccttt atcactttcc cttcagttca cccagcgggg   76560
acaacacgca gacacccggt ggtggctgca gggcccccgg cagccagcgg tgataatgca   76620
gggaaaggcg ccccaacctc agctacgcgg gcgcccacag ggcttctccc cacccctaca   76680
cgtgccccag cgccctggag accgcgcctg ggagctacga gcgagcacct tccctcgcag   76740
agatggatca gattagcccc ctggggcggt ggcacctgcc cgtcccctcc cctcctctct   76800
tctcccaccc ccgccttccc cctgctctgg gcccctgca cctccctctt ggggcccacg    76860
cgccgcccct ctccctcgct tgagctctga gctcagaagg aacctgcccg caaacctggc   76920
tcccagcccc gcccagggag cgcgcgtccc tgagcccaag ggcccagcg acagcaggga    76980 ctggctgcag ccggcagtgc gggggtccag ccggggcgag ccggtcccgc ttgctgcacc   77040
tccgcctcgc acagtcgccg gcagccagct gaaaacagcg cagccgcgtg gtgccacctg   77100
ctggtctctg ggaaggagga ggatgggacg gttgttgcgg ctctgggact gcccctggcc   77160
ccgagggttg agaagcatct tggcgccggg ccctcagccg ccagcttcga ggctgctggg   77220
agcagcagct gctaaggaga agcctgggtc agagttctgc ccaccgcgc ccatctccat    77280 catttcccca aacctcgagt ccctgctttt taaggaatc tgtgcccct aaactggctc     77340 cttaccttc tgagaagcat tgacagtatt ccaggggtgg ccagcaccct gaaaaccaca    77400
gcaaagcggg cagagttaaa atttaagact aaaaatgaca gcatcaggca tgcacgcggg   77460
aaggaacaga acaaccagct ccaggggttc ccatcaccca gggaggccac caacgcccca   77520
accaggagcc atagcagcaa atttatgaaa aaaatatttt attccaaaac actgtttaca   77580
caaatgtgtg gtctttgtac aaagtacaaa aaaaccctc ttctcatccc cacctccctt    77640
cagagaagtt taaaccttgg gctctcaatc ttccatggtc agctgcccct gactgcgagt   77700
cctacagcct cagagggagg agcgtgtggg gttgggagca aggcctcacc agaacacagc   77760
cagttacgca acagcgcaag gcctgctcca ggccccacct ccagcggagt caaaccagat   77820
cagcttttac ccctcactcc agattccaca ggcacgcagc acatggctga tttgcagctt   77880
gtctttcact gcagttttt gttttgttt tttccaggag gcaagaggac caaccctcca    77940
agtcccgggg ccctgtcca cccaccatat cctagaccca atctttcta cctctttgtc    78000 gacaaggtta caaacagaga ggcaagcaaa gaaggctggg gccaacgga ggggagagaa    78060 tatatatccc gggaaacgtg gcaacagca tcatagactt gaatgaagcc caaggccaag    78120
cagccaagca aggactaatt cagagcagct cagaaaccct cactcaaacc ggcggccccc   78180
ctgtgctaag gacatggccg ggcccagacg cgctctcata gggttcacag agagtctgga   78240
gtccacgttc actaaagtat aaaatactac tcgaaaatga accccagcct cccttctgag   78300
agatgaatcg gttacatcaa cacatgagga cagatgcatt tacatagacc cacacactct   78360
ctctttctct ctctctgtct ctctgtctct ctctcttagg agggcaaagc ttctcactcc   78420
ggagtgaaac ttcagcttac agacgttacc tgtctcccct cccttctga atcatctcat    78480 tcaaatagct gctgagcaga tgaggggccc aggaggaata ggtctggctg cattgagtgc   78540
ctgcagtgac agaggctcgg tctctaccat gacagagaca gactcggcgc actcttggat   78600
```

```
gccatgatct gaaaagaggc caccgctgct gcagccacat cccaggactg cacaggggag    78660
gcaggcgtag ctcatgcaca aggacacaca cacacacaca cacacaagca catgcatgcc    78720
tgcaaaggtg tcagtgtaca cagccttact aaactcacaa cacgaccgct tcacattgca    78780
tattgtttcc aaagagaagc gtgggattca aacattcatg agaggagcc tctggcagag     78840 gtgaaaagac cggcagggggg cgagaggcgg gagtcaagac tgtccattgg tcggcgtaag   78900
agttcctcca cgtgcctggc cacatccatg gtctcatcca ggtcgaattc tccatcctga    78960
tcgagtacat ggtcagggct ggtaaagaca gggggatgtc a                        79001
```

<210> SEQ ID NO 3
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 3
actgccgcag ctccat                                                    16

<210> SEQ ID NO 4
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 4
gagattctct acca                                                      14

<210> SEQ ID NO 5
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 5
agatcttgca tgtctc                                                    16

<210> SEQ ID NO 6
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 6
ataattcaac tcaggg                                                    16

<210> SEQ ID NO 7
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 7
actttttcac aaggtc                                                    16

<210> SEQ ID NO 8
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 8
ccatgatctt atagcc                                                   16

<210> SEQ ID NO 9
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 9
gatagcagaa gtagga                                                   16

<210> SEQ ID NO 10
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 10
caaggttaaa aagtgc                                                   16

<210> SEQ ID NO 11
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 11
aaggttaaaa agtg                                                     14

<210> SEQ ID NO 12
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 12
ctatttggat gtcagc                                                   16

<210> SEQ ID NO 13
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 13
tatttggatg tcag                                                     14

<210> SEQ ID NO 14
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 14
tagatagtcc tatctt                                                   16
```

<210> SEQ ID NO 15
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 15
agatagtcct atct                                                        14

<210> SEQ ID NO 16
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 16
aagaaaccta gggctt                                                      16

<210> SEQ ID NO 17
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 17
agaaacctag ggct                                                        14

<210> SEQ ID NO 18
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 18
gctgatacag tgtttt                                                      16

<210> SEQ ID NO 19
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 19
ctgatacagt gttt                                                        14

<210> SEQ ID NO 20
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 20
atacagaaag gctatg                                                      16

<210> SEQ ID NO 21
<211> LENGTH: 14
<212> TYPE: DNA
<213> ORGANISM: Artificial sequence
<220> FEATURE:

<223> OTHER INFORMATION: Synthetic oligonucleotide

<400> SEQUENCE: 21
tacagaaagg ctat                                                        14

<210> SEQ ID NO 22
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 22
gcttaagttt cttaaa                                                      16

<210> SEQ ID NO 23
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 23
cttaagtttc ttaa                                                        14

<210> SEQ ID NO 24
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 24
agcaccaagg aggctg                                                      16

<210> SEQ ID NO 25
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 25
gcaccaagga ggct                                                        14

<210> SEQ ID NO 26
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 26
aagctgaatg cttaaa                                                      16

<210> SEQ ID NO 27
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 27
agctgaatgc ttaa                                                        14

```
<210> SEQ ID NO 28
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 28
ttaccagcct gaagga                                                      16

<210> SEQ ID NO 29
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 29
taccagcctg aagg                                                        14

<210> SEQ ID NO 30
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 30
cagggattat ataaat                                                      16

<210> SEQ ID NO 31
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 31
agggattata taaa                                                        14

<210> SEQ ID NO 32
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 32
acctgaagcc cgtttc                                                      16

<210> SEQ ID NO 33
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 33
cctgaagccc gttt                                                        14

<210> SEQ ID NO 34
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 34
tgtcttaagg gtttga                                                    16

<210> SEQ ID NO 35
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 35
gtcttaaggg tttg                                                      14

<210> SEQ ID NO 36
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 36
ggttgcagct tcagat                                                    16

<210> SEQ ID NO 37
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 37
gttgcagctt caga                                                      14

<210> SEQ ID NO 38
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 38
tcaacaccaa aggcca                                                    16

<210> SEQ ID NO 39
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 39
caacaccaaa ggcc                                                      14

<210> SEQ ID NO 40
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 40
tccttaaacc ttccta                                                    16

<210> SEQ ID NO 41
<211> LENGTH: 14

```
<212> TYPE: DNA
<213> ORGANISM: Artificial sequence
<220> FEATURE:
<223> OTHER INFORMATION: Synthetic oligonucleotide

<400> SEQUENCE: 41
ccttaaacct tcct                                                        14

<210> SEQ ID NO 42
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 42
aaaatgctta gattct                                                      16

<210> SEQ ID NO 43
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 43
aaatgcttag attc                                                        14

<210> SEQ ID NO 44
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 44
aaataagtct atttat                                                      16

<210> SEQ ID NO 45
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 45
aataagtcta ttta                                                        14

<210> SEQ ID NO 46
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 46
ggccaataca ttacaa                                                      16

<210> SEQ ID NO 47
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 47
```

```
gccaatacat taca                                              14

<210> SEQ ID NO 48
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 48
tgcccagcct tactca                                            16

<210> SEQ ID NO 49
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 49
gcccagcctt actc                                              14

<210> SEQ ID NO 50
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 50
gttgtaagca ccctct                                            16

<210> SEQ ID NO 51
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 51
ttgtaagcac cctc                                              14

<210> SEQ ID NO 52
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 52
agaaagggag tcaagg                                            16

<210> SEQ ID NO 53
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 53
gaaagggagt caag                                              14

<210> SEQ ID NO 54
<211> LENGTH: 16
<212> TYPE: DNA
<213> ORGANISM: Artificial sequence
```

```
<220> FEATURE:
<223> OTHER INFORMATION: Synthetic oligonucleotide

<400> SEQUENCE: 54
gcagatcaag tccagg                                                     16

<210> SEQ ID NO 55
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 55
cagatcaagt ccag                                                       14

<210> SEQ ID NO 56
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 56
agcctctgaa acagca                                                     16

<210> SEQ ID NO 57
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 57
gcctctgaaa cagc                                                       14

<210> SEQ ID NO 58
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 58
cccacagaaa caacct                                                     16

<210> SEQ ID NO 59
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 59
ccacagaaac aacc                                                       14

<210> SEQ ID NO 60
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 60
agccctgata aggcac                                                     16
```

```
<210> SEQ ID NO 61
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 61
gccctgataa ggca                                                       14

<210> SEQ ID NO 62
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 62
aatcagaagt atccca                                                     16

<210> SEQ ID NO 63
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 63
atcagaagta tccc                                                       14

<210> SEQ ID NO 64
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 64
gcctctagca ggatca                                                     16

<210> SEQ ID NO 65
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 65
cctctagcag gatc                                                       14

<210> SEQ ID NO 66
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 66
cacgcaagga gacatg                                                     16

<210> SEQ ID NO 67
<211> LENGTH: 14
<212> TYPE: DNA
<213> ORGANISM: Artificial sequence
<220> FEATURE:
<223> OTHER INFORMATION: Synthetic oligonucleotide
```

```
<400> SEQUENCE: 67
acgcaaggag acat                                                        14

<210> SEQ ID NO 68
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 68
tgagggacct ttagac                                                      16

<210> SEQ ID NO 69
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 69
gagggacctt taga                                                        14

<210> SEQ ID NO 70
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 70
caggattcct aaaaca                                                      16

<210> SEQ ID NO 71
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 71
aggattccta aaac                                                        14

<210> SEQ ID NO 72
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 72
atgaggtcct gagacc                                                      16

<210> SEQ ID NO 73
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 73
tgaggtcctg agac                                                        14

<210> SEQ ID NO 74
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 74
catcatgtcc aacctg                                                    16

<210> SEQ ID NO 75
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 75
atcatgtcca acct                                                      14

<210> SEQ ID NO 76
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 76 gggcccata gtgtgc                                                     16

<210> SEQ ID NO 77
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 77
ggccccatag tgtg                                                      14

<210> SEQ ID NO 78
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 78
agctcaacca gacacg                                                    16

<210> SEQ ID NO 79
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 79
gctcaaccag acac                                                      14

<210> SEQ ID NO 80
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 80
```
gaaccatatt ccctga                                              16

<210> SEQ ID NO 81
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 81
aaccatattc cctg                                                14

<210> SEQ ID NO 82
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 82
caagaaactg gctaag                                              16

<210> SEQ ID NO 83
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 83
aagaaactgg ctaa                                                14

<210> SEQ ID NO 84
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 84
gccactggat atcacc                                              16

<210> SEQ ID NO 85
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 85
aactgaatga agacgc                                              16

<210> SEQ ID NO 86
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 86
gcttattatg tactga                                              16

<210> SEQ ID NO 87
<211> LENGTH: 14
<212> TYPE: DNA

```
<213> ORGANISM: Artificial sequence
<220> FEATURE:
<223> OTHER INFORMATION: Synthetic oligonucleotide

<400> SEQUENCE: 87
cttattatgt actg                                                         14

<210> SEQ ID NO 88
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 88
gcccaagtct cacctt                                                       16

<210> SEQ ID NO 89
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 89
cccaagtctc acct                                                         14

<210> SEQ ID NO 90
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 90
cccaatggta agccca                                                       16

<210> SEQ ID NO 91
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 91
ccaatggtaa gccc                                                         14

<210> SEQ ID NO 92
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 92
aacccaatgg taagcc                                                       16

<210> SEQ ID NO 93
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 93
acccaatggt aagc                                                         14
```

-continued

```
<210> SEQ ID NO 94
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 94
taggtcccta tgattt                                                   16

<210> SEQ ID NO 95
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 95
aggtccctat gatt                                                     14

<210> SEQ ID NO 96
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 96
aagccctgaa ccctcg                                                   16

<210> SEQ ID NO 97
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 97
agccctgaac cctc                                                     14

<210> SEQ ID NO 98
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 98
cctaaggcca tgaact                                                   16

<210> SEQ ID NO 99
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 99
ctaaggccat gaac                                                     14

<210> SEQ ID NO 100
<211> LENGTH: 16
<212> TYPE: DNA
<213> ORGANISM: Artificial sequence
<220> FEATURE:
```

<223> OTHER INFORMATION: Synthetic oligonucleotide

<400> SEQUENCE: 100
accagataca tgctac     16

<210> SEQ ID NO 101
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 101
ccagatacat gcta     14

<210> SEQ ID NO 102
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 102
tacaatcaga gttaag     16

<210> SEQ ID NO 103
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 103
acaatcagag ttaa     14

<210> SEQ ID NO 104
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 104
tcctctcaga actttt     16

<210> SEQ ID NO 105
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 105
cctctcagaa cttt     14

<210> SEQ ID NO 106
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 106
gctcctctca gaactt     16

```
<210> SEQ ID NO 107
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 107
ctcctctcag aact                                                    14

<210> SEQ ID NO 108
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 108
ttctttaatg ggccac                                                  16

<210> SEQ ID NO 109
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 109
tctttaatgg gcca                                                    14

<210> SEQ ID NO 110
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 110
acgggattcc ctcggc                                                  16

<210> SEQ ID NO 111
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 111
cgggattccc tcgg                                                    14

<210> SEQ ID NO 112
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 112
gtaggtaagc aaccca                                                  16

<210> SEQ ID NO 113
<211> LENGTH: 14
<212> TYPE: DNA
<213> ORGANISM: Artificial sequence
<220> FEATURE:
<223> OTHER INFORMATION: Synthetic oligonucleotide
```

```
<400> SEQUENCE: 113
taggtaagca accc                                                  14

<210> SEQ ID NO 114
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 114
gaatttgaat gcagtg                                                16

<210> SEQ ID NO 115
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 115
aatttgaatg cagt                                                  14

<210> SEQ ID NO 116
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 116
tgaagtacac attgga                                                16

<210> SEQ ID NO 117
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 117
gaagtacaca ttgg                                                  14

<210> SEQ ID NO 118
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 118
ataaattttt acacta                                                16

<210> SEQ ID NO 119
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 119
taaattttta cact                                                  14

<210> SEQ ID NO 120
<211> LENGTH: 14
```

```
<212> TYPE: DNA
<213> ORGANISM: Artificial sequence
<220> FEATURE:
<223> OTHER INFORMATION: Synthetic oligonucleotide

<400> SEQUENCE: 120
caataatata aatt                                                        14

<210> SEQ ID NO 121
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 121
ctggaagtta aagtag                                                      16

<210> SEQ ID NO 122
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 122
tggaagttaa agta                                                        14

<210> SEQ ID NO 123
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 123
gtactctttc agtggt                                                      16

<210> SEQ ID NO 124
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 124
atgcttagat tctcct                                                      16

<210> SEQ ID NO 125
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 125
agcagatcaa gtccag                                                      16

<210> SEQ ID NO 126
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 126
```

```
aggtgttccc atacgc                                                      16

<210> SEQ ID NO 127
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 127
taggtgttcc catacg                                                      16

<210> SEQ ID NO 128
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 128
ggttcctcct gttggc                                                      16

<210> SEQ ID NO 129
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 129
atgcttagat tctcctt                                                     17
```

CANCER TREATMENT

This application is a Continuation of U.S. application Ser. No. 15/356,947 filed on Nov. 21, 2016, said U.S. application Ser. No. 15/356,947 is a Continuation of U.S. application Ser. No. 14/439,363, filed Apr. 29, 2015, now U.S. Pat. No. 9,540,641, said U.S. application Ser. No. 14/439,363 is a U.S. National Stage application under 35 U.S.C. § 371 of International Application No. PCT/US2013/067469, filed on Oct. 30, 2013, which claims benefit under 35 U.S.C. § 119(e) of the following U.S. Provisional Application Nos. 61/720,939, filed Oct. 31, 2012 and 61/777,875, filed Mar. 12, 2013. Each of the above listed applications is incorporated by reference herein in its entirety for all purposes.

SEQUENCE LISTING

The present application is being filed along with a Sequence Listing in electronic format. The Sequence Listing is provided as a file entitled BIOL0216USL2SEQ.txt created Mar. 12, 2013, which is 124 kb in size. The information in the electronic format of the sequence listing is incorporated herein by reference in its entirety.

FIELD

In certain embodiments, methods, compounds, and compositions for treating B-cell lymphoma by inhibiting expression of STAT3 mRNA or protein in an animal are provided herein. Such methods, compounds, and compositions are useful to treat, prevent, or ameliorate B-cell lymphoma or hepatocellular carcinoma.

BACKGROUND

The STAT (signal transducers and activators of transcription) family of proteins are DNA-binding proteins that play a dual role in signal transduction and activation of transcription. Presently, there are six distinct members of the STAT family (STAT1, STAT2, STAT3, STAT4, STAT5, and STAT6) and several isoforms (STAT1α, STAT1β, STAT3α and STAT3β). The activities of the STATs are modulated by various cytokines and mitogenic stimuli. Binding of a cytokine to its receptor results in the activation of Janus protein tyrosine kinases (JAKs) associated with these receptors. This phosphorylates STAT, resulting in translocation to the nucleus and transcriptional activation of STAT responsive genes. Phosphorylation on a specific tyrosine residue on the STATs results in their activation, resulting in the formation of homodimers and/or heterodimers of STAT which bind to specific gene promoter sequences. Events mediated by cytokines through STAT activation include cell proliferation and differentiation and prevention of apoptosis.

The specificity of STAT activation is due to specific cytokines, i.e., each STAT is responsive to a small number of specific cytokines. Other non-cytokine signaling molecules, such as growth factors, have also been found to activate STATs. Binding of these factors to a cell surface receptor associated with protein tyrosine kinase also results in phosphorylation of STAT.

STAT3 (also acute phase response factor (APRF)), in particular, has been found to be responsive to interleukin-6 (IL-6) as well as epidermal growth factor (EGF) (Darnell, Jr., J. E., et al., Science, 1994, 264, 1415-1421). In addition, STAT3 has been found to have an important role in signal transduction by interferons (Yang, C.-H., et al., Proc. Natl. Acad. Sci. USA, 1998, 95, 5568-5572). Evidence exists suggesting that STAT3 may be regulated by the MAPK pathway. ERK2 induces serine phosphorylation and also associates with STAT3 (Jain, N., et al., Oncogene, 1998, 17, 3157-3167).

STAT3 is expressed in most cell types (Zhong, Z., et al., Proc. Natl. Acad. Sci. USA, 1994, 91, 4806-4810). It induces the expression of genes involved in response to tissue injury and inflammation. STAT3 has also been shown to prevent apoptosis through the expression of bcl-2 (Fukada, T., et al., Immunity, 1996, 5, 449-460).

Recently, STAT3 was detected in the mitochondria of transformed cells, and was shown to facilitate glycolytic and oxidative phosphorylation activities similar to that of cancer cells (Gough, D. J., et al., Science, 2009, 324, 1713-1716). The inhibition of STAT3 in the mitochondria impaired malignant transformation by activated Ras. The data confirms a Ras-mediated transformation function for STAT3 in the mitochondria in addition to its nuclear roles.

Aberrant expression of or constitutive expression of STAT3 is associated with a number of disease processes.

SUMMARY

B-cell lymphoma is a B-lymphocyte blood cell cancer that is clinically classified as either Hodgkin's lymphoma or non-Hodgkin's lymphoma. There are several types of non-Hodgkin's lymphoma, of which diffuse large B-cell lymphoma (DLBCL) is the most common type, accounting for approximately 30 percent of all lymphomas. In the United States, DLBCL affects about 7 out of 100,000 people each year.

Several embodiments provided herein relate to the discovery that inhibiting the JAK-STAT signaling pathway can be useful for treating B-cell lymphoma. In certain embodiments, antisense compounds targeting STAT3 are useful for treating B-cell lymphoma, such as DLBCL, at unexpectedly low doses for an antisense compound as a cancer therapeutic. In several embodiments, antisense compounds targeting STAT3 provided herein are administered to a subject having B-cell lymphoma at a fixed total weekly dose in the range of about 15-750 mg. In certain embodiments, antisense compounds targeting STAT3 provided herein are administered to a subject having B-cell lymphoma in the range of about 0.2 to 3.5 milligrams of the antisense compound per kilogram of the subject's body weight per week (0.2-3.5 mg/kg/wk). Such dose ranges are unexpectedly low for treating cancer. By comparison, a Phase 1 study of LY2275796, an antisense oligonucleotide targeted to cap-binding protein eukaryotic initiation factor 4E (eIF-4E), concluded that the maximum tolerable dose (MTD) and biologically effective dose (BED) of LY2275796 is 1,000 mg under a loading and maintenance dose regimen, but even at a 1,000 mg dose, no tumor response was observed. (Hong D. S. et al., Clin Cancer Res. 2011 17(20):6582-91).

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of the term "or" means "and/or", unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-deoxynucleoside" means a nucleoside comprising 2'-H furanosyl sugar moiety, as found naturally occurring in deoxyribonucleosides (DNA). In certain embodiments, a 2'-deoxynucleoside may comprise a modified nucleobase or may comprise an RNA nucleobase (e.g., uracil).

"2'-O-methoxyethyl" (also 2'-MOE and 2'-O(CH$_2$)$_2$—OCH$_3$) refers to an O-methoxy-ethyl modification of the 2' position of a furosyl ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" means a nucleoside comprising a substituent at the 2'-position other than H or OH. Unless otherwise indicated, a 2'-substituted nucleoside is not a bicyclic nucleoside.

"5'-methylcytosine" means a cytosine modified with a methyl group attached to the 5' position. A 5-methylcytosine is a modified nucleobase.

"About" as applied to dosing amounts means within ±12% of a value. For example, if it is stated, "the dose is an amount in the range of about 15-750 mg," it is implied that the dose is an amount in the range of 13-840 mg. In another example, if it is stated that the dose is an amount of "about 50 mg," it is implied that the dose can be from 44 mg to 56 mg. "About" as applied to activity levels means within ±10% of a value. For example, if it is stated, "the compounds affected at least about 70% inhibition of STAT3", it is implied that the STAT3 levels are inhibited within a range of 63% and 77%.

"Active pharmaceutical agent" means the substance or substances in a pharmaceutical composition that provide a therapeutic benefit when administered to an individual. For example, in certain embodiments an antisense oligonucleotide targeted to STAT3 is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to administering by a medical professional and self-administering.

"Amelioration" refers to a lessening of at least one indicator, sign, or symptom of an associated disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, and shRNAs.

"Antisense inhibition" means reduction of target nucleic acid levels or target protein levels in the presence of an antisense compound complementary to a target nucleic acid as compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furosyl ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-CH(CH$_3$)—O-2'.

"Constrained ethyl nucleoside" (also cEt nucleoside) means a nucleoside comprising a bicyclic sugar moiety comprising a 4'-CH(CH$_3$)—O-2' bridge.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Contiguous nucleobases" means nucleobases immediately adjacent to each other.

"Diluent" means an ingredient in a composition that lacks pharmacological activity, but is pharmaceutically necessary or desirable. For example, the diluent in an injected composition may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month. In certain embodiments, single dose means administration of one dose, and only one dose, to a subject.

"Dosage unit" means a form in which a pharmaceutical agent is provided. In certain embodiments, a dosage unit is a vial containing lyophilized ISIS 481464. In certain embodiments, a dosage unit is a vial containing reconstituted ISIS 481464.

"Dosing regimen" is a combination of doses designed to achieve one or more desired effects. In certain embodiments, a dose regimen is designed to provide a therapeutic effect quickly.

"Duration" means the period of time during which an activity or event continues. For example, the duration of a loading phase is the period of time during which loading doses are administered. For example, the duration of the maintenance phase is the period of time during which maintenance doses are administered.

"Effective amount" means the amount of active pharmaceutical agent sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

"First phase" means a dosing phase during which administration is initiated and steady state concentrations of pharmaceutical agents can be, but is not necessarily, achieved in a target tissue. "Second phase" means a dosing phase after the "first phase." In certain embodiments, the dose or total weekly dose of the first phase and the second phase are different.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Gap-widened" means a chimeric antisense compound having a gap segment of 12 or more contiguous 2'-deoxyribonucleosides positioned between and immediately adjacent to 5' and 3' wing segments having from one to six nucleosides.

"HCC" means hepatocellular carcinoma. It is the most common form of liver cancer and also referred to as malignant hepatoma.

"Hybridization" means the annealing of complementary nucleic acid molecules. In certain embodiments, complementary nucleic acid molecules include an antisense compound and a target nucleic acid.

"Hyperproliferative disease" means a disease characterized by rapid or excessive growth and reproduction of cells. Examples of hyperproliferative diseases include cancer, e.g., carcinomas, sarcomas, lymphomas, and leukemias as well as associated malignancies and metastases.

"Identifying an animal at risk for hyperproliferative disease" means identifying an animal having been diagnosed with a hyperproliferative disease or identifying an animal predisposed to develop a hyperproliferative disease. Individuals predisposed to develop a hyperproliferative disease include those having one or more risk factors for hyperproliferative disease including older age; history of other hyperproliferative diseases; history of tobacco use; history of exposure to sunlight and/or ionizing radiation; prior contact with certain chemicals, especially continuous contact; past or current infection with certain viruses and bacteria; prior or current use of certain hormone therapies; genetic predisposition; alcohol use; and certain lifestyle choices including poor diet, lack of physical activity, and/or being overweight. Such identification may be accomplished by any method including evaluating an individual's medical history and standard clinical tests or assessments.

"Immediately adjacent" means there are no intervening elements between the immediately adjacent elements.

"Inhibiting STAT3" means reducing expression of STAT3 mRNA and/or protein levels in the presence of a STAT3 antisense compound, including a STAT3 antisense oligonucleotide, as compared to expression of STAT3 mRNA and/or protein levels in the absence of a STAT3 antisense compound, such as an antisense oligonucleotide.

"Individual" means a human or non-human animal selected for treatment or therapy.

"Internucleoside linkage" refers to the chemical bond between nucleosides.

"ISIS 481464" means a STAT3 antisense oligonucleotide having the nucleobase sequence "CTATTTGGATGTCAGC", incorporated herein as SEQ ID NO: 12, where each internucleoside linkage is a phosphorothioate internucleoside linkage, each cytosine is a 5-methylcytosine, and each of nucleosides 1-3 and 14-16 comprise a cEt moeity. ISIS 481464 is complementary to nucleobases 3016-3031 of the sequence of GENBANK Accession No. NM_139276.2, incorporated herein as SEQ ID NO:1.

"Linked nucleosides" means adjacent nucleosides which are bonded together.

"Loading phase" means a dosing phase during which administration is initiated and steady state concentrations of pharmaceutical agents are achieved in a target tissue. For example, a loading phase is a dosing phase during which steady state concentrations of antisense oligonucleotide are achieved in liver.

"Maintenance phase" means a dosing phase after target tissue steady state concentrations of pharmaceutical agents have been achieved. For example, a maintenance phase is a dosing phase after which steady state concentrations of antisense oligonucleotide are achieved in liver.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising a modified internucleoside linkage, a modified sugar, and/or a modified nucleobase.

"Modified sugar" refers to a substitution or change from a natural sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system.

"Nucleotide" means a nucleoside having a phosphate group covalently linked to the sugar portion of the nucleoside.

"Off-target effect" refers to an unwanted or deleterious biological effect associated with modulation of RNA or protein expression of a gene other than the intended target nucleic acid.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection (e.g., bolus injection) or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Peptide refers to polypeptides and proteins.

"Pharmaceutical composition" means a mixture of substances suitable for administering to an individual. For example, a pharmaceutical composition may comprise one or more active pharmaceutical agents and a sterile aqueous solution. In certain embodiments, a pharmaceutical composition shows activity in free uptake assay in certain cell lines.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage (P=S) is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Signal Transducer and Activator of Transcription 3 nucleic acid" or "STAT3 nucleic acid" means any nucleic acid encoding STAT3. For example, in certain embodiments, a STAT3 nucleic acid includes a DNA sequence encoding STAT3, an RNA sequence transcribed from DNA encoding STAT3 (including genomic DNA comprising introns and exons), and an mRNA sequence encoding STAT3. "STAT3 mRNA" means an mRNA encoding a STAT3 protein.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Subject" means a human selected for treatment or therapy.

"Targeting" or "targeted" means the process of design and selection of an antisense compound that will specifically hybridize to a target nucleic acid and induce a desired effect.

"Target nucleic acid," "target RNA," "target mRNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'—most nucleotide of a target segment. "3' target site" refers to the 3'—most nucleotide of a target segment.

"Therapeutically effective amount" means an amount of a pharmaceutical agent that provides a therapeutic benefit to an individual.

"Treat" refers to administering a pharmaceutical composition to effect an alteration or improvement of a disease, disorder, or condition.

"Unmodified nucleotide" means a nucleotide composed of naturally occuring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

In certain aspects, there is provided a method of treating cancer in a subject which comprises administering to the subject an inhibitor of the JAK-STAT pathway. In certain embodiments the cancer is B-cell lymphoma or hepatocellular carcinoma (HCC).

In certain aspects, there is provided a method of treating B-cell lymphoma in a subject which comprises administering to the subject an inhibitor of the JAK-STAT pathway.

In certain aspects, there is provided a method of treating cancer, such as B-cell lymphoma or HCC, in a subject which comprises administering to the subject a weekly dose of an antisense compound complementary to a nucleic acid encoding human STAT3, wherein the dose comprises about 0.2 to 3.5 milligrams of the antisense compound per kilogram of the subject's body weight per week (0.2-3.5 mg/kg/wk). In certain embodiments, the dose is about 0.2 mg, about 0.3 mg, about 0.4 mg, about 0.5 mg, about 0.6 mg, about 0.7 mg, about 0.8 mg, about 0.9 mg, about 1.0 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, about 2.1 mg, about 2.2 mg, about 2.3 mg, about 2.4 mg, about 2.5 mg, about 2.6 mg, about 2.7 mg, about 2.8 mg, about 2.9 mg, about 3.0 mg, about 3.1 mg, about 3.2 mg, about 3.3 mg, about 3.4 mg, or about 3.5 mg of the antisense compound per kilogram of the subject's body weight. In certain embodiments, the dose comprises about 1.5 to 3.5 milligrams of the antisense compound per kilogram of the subject's body weight (1.5-3.5 mg/kg/wk). In certain embodiments, the dose is 2.0 milligrams of the antisense compound per kilogram of the subject's body weight per week (2.0 mg/kg/wk). In certain embodiments, the dose is effective to treat cancer and acceptably tolerable. The dose can be administered for at least 1-52 weeks, at least 1-10 weeks, at least 1-7 weeks, at least 1-5 weeks, at least 5 weeks, at least 6 weeks, or at least 7 weeks. In certain embodiments, the dose can be administered to the subject 1, 2, 3, 4, 5, 6, or 7 times per week. In certain embodiments, the dose is administered to the subject 1-6 times per week. In several embodiments, the dose can be administered 6 times during the first week and 1 time each subsequent week. In certain embodiments, the subject's body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet.

In certain embodiments, a method comprises administering to a subject having cancer, such as B-cell lymphoma or HCC, a single dose of a pharmaceutical composition comprising an antisense compound complementary to a nucleic acid encoding human STAT3, wherein the single dose comprises an amount of the compound in the range of about 15-250 mg. In certain embodiments, the single dose comprises an amount of the compound in the range of about 100-250 mg. In certain embodiments, the single dose is an amount of any of about 15 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, or about 250 mg. In certain embodiments, the dose is effective to treat cancer and acceptably tolerable.

In certain embodiments, a method comprises administering to a subject having cancer, such as B-cell lymphoma or HCC, a total weekly dose of a pharmaceutical composition comprising an antisense compound complementary to a nucleic acid encoding human STAT3, wherein the total weekly dose comprises an amount of the compound in the range of about 15-750 mg weekly. In certain embodiments, the total weekly dose comprises an amount of the compound in the range of about 100-750 mg weekly. In certain embodiments, the total weekly dose is an amount of any of about 15 mg, about 20 mg, about 30 mg, about 40 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, or about 750 mg. In certain embodiments, the dose is effective to treat cancer and acceptably tolerable. The total weekly dose can be administered in 2, 3, 4, 5, 6, or 7 equal doses within a week, such that the total weekly dose does not exceed about 750 mg. In certain embodiments, the total weekly dose is administered in 3 equal doses within a week. It will be understood that the aforementioned total weekly dose ranges can be readily represented as milligrams of the antisense compound per kilogram of the subject's body weight per week (mg/kg/wk) by simply dividing the total weekly dose by the subject's body weight, such as the subject's ideal body weight. For example, dividing the aforementioned total weekly dose by an average adult body weight of 70 kg, in certain embodiments the total weekly dose can be represented as an amount of about 15 mg/70 kg (0.2 mg/kg/wk) to 750 mg/70 kg (10.7 mg/kg/wk). In certain embodiments, the total weekly dose can be represented as any of about 15 mg/70 kg (0.2 mg/kg/wk), about 20 mg/70 kg (0.3 mg/kg/wk), about 30 mg/70 kg (0.4 mg/kg/wk), about 40 mg/70 kg (0.6 mg/kg/wk), about 50 mg/70 kg (0.7 mg/kg/wk), about 75 mg/70 kg (1.1 mg/kg/wk), about 100 mg/70 kg (1.4 mg/kg/wk), about 125 mg/70 kg (1.8 mg/kg/wk), about 150 mg/70 kg (2.1 mg/kg/wk), about 175 mg/70 kg (2.5 mg/kg/wk), about 200 mg/70 kg (2.9 mg/kg/wk), about 225 mg/70 kg (3.2 mg/kg/wk), about 250 mg/70 kg (3.6 mg/kg/wk), about 275 mg/70 kg (3.9 mg/kg/wk), about 300 mg/70 kg (4.3 mg/kg/wk), about 325 mg/70 kg (4.6 mg/kg/wk), about 350 mg/70 kg (5.0 mg/kg/wk), about 375 mg/70 kg (5.4 mg/kg/wk), about 400 mg/70 kg (5.7 mg/kg/wk), about 425 mg/70 kg (6.1 mg/kg/wk), about 450 mg/70 kg (6.4 mg/kg/wk), about 475 mg/70 kg (6.8 mg/kg/wk), about 500 mg/70 kg (7.1 mg/kg/wk), about 525 mg/70 kg (7.5 mg/kg/wk), about 550 mg/70 kg (7.9 mg/kg/wk), about 575 mg/70 kg (8.2 mg/kg/wk), about 600 mg/70 kg (8.6 mg/kg/wk), about 625 mg/70 kg (8.9 mg/kg/wk), about 650 mg/70 kg (9.3 mg/kg/wk), about 675 mg/70 kg (9.6 mg/kg/wk), about 700 mg/70 kg (10.0 mg/kg/wk), about 725 mg/70 kg (10.4 mg/kg/wk), or about 750 mg/70 kg (10.7 mg/kg/wk). In certain embodiments, body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet.

In certain aspects, a method comprises administering to a subject having cancer, such as B-cell lymphoma or HCC, a pharmaceutical composition comprising an antisense compound complementary to a nucleic acid encoding human STAT3, wherein administering the antisense compound comprises:

a loading phase comprising a total weekly dose in the range of about 15-750 mg for the first 1-10 weeks, and a maintenance phase comprising a total weekly dose in the range of 15-250 mg for at least 1 week after the loading phase.

In certain embodiments, the loading phase is 1 week, 2 weeks, 3 weeks, 4 weeks, or 5 weeks. In certain embodiments, the loading phase comprises administering the compound in 2, 3, 4, 5, 6, or 7 equal doses within a week. In certain embodiments, the loading phase comprises administering the compound in 3 equal doses within a week. In several embodiments, the total weekly dose of the antisense compound in the loading phase is an amount of any of about 15 mg, about 20 mg, about 30 mg, about 40 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, or about 750 mg. It will be understood that the aforementioned total weekly dose ranges in the loading phase can be readily represented as milligrams of the antisense compound per kilogram of the subject's body weight per week (mg/kg/wk) by simply dividing the total weekly dose by the subject's body weight, such as the subject's ideal body weight. For example, dividing the aforementioned total weekly dose in the loading phase by an average adult body weight of 70 kg, in certain embodiments the total weekly dose can be represented as an amount of about 15 mg/70 kg (0.2 mg/kg/wk) to 750 mg/70 kg (10.7 mg/kg/wk). In certain embodiments, the total weekly dose in the loading phase can be represented as any of about 15 mg/70 kg (0.2 mg/kg/wk), about 20 mg/70 kg (0.3 mg/kg/wk), about 30 mg/70 kg (0.4 mg/kg/wk), about 40 mg/70 kg (0.6 mg/kg/wk), about 50 mg/70 kg (0.7 mg/kg/wk), about 75 mg/70 kg (1.1 mg/kg/wk), about 100 mg/70 kg (1.4 mg/kg/wk), about 125 mg/70 kg (1.8 mg/kg/wk), about 150 mg/70 kg (2.1 mg/kg/wk), about 175 mg/70 kg (2.5 mg/kg/wk), about 200 mg/70 kg (2.9 mg/kg/wk), about 225 mg/70 kg (3.2 mg/kg/wk), about 250 mg/70 kg (3.6 mg/kg/wk), about 275 mg/70 kg (3.9 mg/kg/wk), about 300 mg/70 kg (4.3 mg/kg/wk), about 325 mg/70 kg (4.6 mg/kg/wk), about 350 mg/70 kg (5.0 mg/kg/wk), about 375 mg/70 kg (5.4 mg/kg/wk), about 400 mg/70 kg (5.7 mg/kg/wk), about 425 mg/70 kg (6.1 mg/kg/wk), about 450 mg/70 kg (6.4 mg/kg/wk), about 475 mg/70 kg (6.8 mg/kg/wk), about 500 mg/70 kg (7.1 mg/kg/wk), about 525 mg/70 kg (7.5 mg/kg/wk), about 550 mg/70 kg (7.9 mg/kg/wk), about 575 mg/70 kg (8.2 mg/kg/wk), about 600 mg/70 kg (8.6 mg/kg/wk), about 625 mg/70 kg (8.9 mg/kg/wk), about 650 mg/70 kg (9.3 mg/kg/wk), about 675 mg/70 kg (9.6 mg/kg/wk), about 700 mg/70 kg (10.0 mg/kg/wk), about 725 mg/70 kg (10.4 mg/kg/wk), or about 750 mg/70 kg (10.7 mg/kg/wk). In certain embodiments, body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet.

In certain embodiments, the maintenance phase comprises administering the compound in 2, 3, 4, 5, 6, or 7 equal doses within a week. In several embodiments, the total weekly dose of the antisense compound in the maintenance phase is an amount of any of about 15 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, or about 250 mg. In certain embodiments, the total weekly dose in the maintenance phase is administered as a single dose per week. It will be understood that the aforementioned total weekly dose ranges in the maintenance phase can be readily represented as milligrams of the antisense compound per kilogram of the subject's body weight per week (mg/kg/wk) by simply dividing the total weekly dose by the subject's body weight, such as the subject's ideal body weight. For example, dividing the aforementioned total weekly dose by an average adult body weight of 70 kg, in certain embodiments the total weekly dose in the maintenance phase can be represented as an amount of about 15 mg/70 kg (0.2 mg/kg/wk) to 250 mg/70 kg (3.6 mg/kg/wk). In certain embodiments, the total weekly dose can be represented as any of about 15 mg/70 kg (0.2 mg/kg/wk), about 20 mg/70 kg (0.3 mg/kg/wk), about 30 mg/70 kg (0.4 mg/kg/wk), about 40 mg/70 kg (0.6 mg/kg/wk), about 50 mg/70 kg (0.7 mg/kg/wk), about 75 mg/70 kg (1.1 mg/kg/wk), about 100 mg/70 kg (1.4 mg/kg/wk), about 125 mg/70 kg (1.8 mg/kg/wk), about 150 mg/70 kg (2.1 mg/kg/wk), about 175 mg/70 kg (2.5 mg/kg/wk), about 200 mg/70 kg (2.9 mg/kg/wk), about 225 mg/70 kg (3.2 mg/kg/wk), or about 250 mg/70 kg (3.6 mg/kg/wk). In certain embodiments, body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+ 2.3 kg/inch over 5 feet.

In certain embodiments, a method comprises administering to a subject having cancer, such as B-cell lymphoma or HCC, a pharmaceutical composition comprising an antisense compound complementary to a nucleic acid encoding human STAT3, wherein administering the antisense compound comprises:

a loading phase about 6, 7, 8, 9, or 10 weeks, and a maintenance phase comprising a dose of about 2 mg/kg/wk for at least 1 week after the loading phase. In certain embodiments, body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+ 2.3 kg/inch over 5 feet.

In certain embodiments, a method comprises administering to a subject having cancer, such as B-cell lymphoma, a pharmaceutical composition comprising an antisense compound complementary to a nucleic acid encoding human STAT3, wherein administering the antisense compound comprises:

a loading phase comprising a dose in the range of about 3 to 4 mg/kg/wk for about 6, 7, 8, 9, or 10 weeks, and a maintenance phase comprising a dose of about 2 mg/kg/wk for at least 1 week after the loading phase. In certain embodiments, body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+ 2.3 kg/inch over 5 feet.

In certain embodiments, a method comprises administering to a subject having cancer, such as B-cell lymphoma or HCC, a pharmaceutical composition comprising an antisense compound complementary to a nucleic acid encoding human STAT3, wherein administering the antisense compound comprises:

a loading phase comprising a dose of about 3 mg/kg/wk for about 8 weeks, and a maintenance phase comprising a dose of about 2 mg/kg/wk for at least 1 week after the loading phase. In certain embodiments, body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+ 2.3 kg/inch over 5 feet.

In certain embodiments, a method comprises administering to a subject having cancer, such as B-cell lymphoma or HCC, a pharmaceutical composition comprising an antisense compound complementary to a nucleic acid encoding human STAT3, wherein administering the antisense compound comprises:

a first phase comprising a total weekly dose in the range of about 15-750 mg for the first 1-10 weeks, and a second phase comprising a total weekly dose in the range of 15-250 mg for at least 1 week after the loading phase.

In certain embodiments, the first phase is 1 week, 2 weeks, 3 weeks, 4 weeks, or 5 weeks. In certain embodiments, the first phase comprises administering the compound in 2, 3, 4, 5, 6, or 7 equal doses within a week. In certain embodiments, the first phase comprises administering the compound in 3 equal doses within a week. In several embodiments, the total weekly dose of the antisense compound in the first phase is an amount of any of about 15 mg, about 20 mg, about 30 mg, about 40 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, or about 750 mg. It will be understood that the aforementioned total weekly dose ranges in the first phase can be readily represented as milligrams of the antisense compound per kilogram of the subject's body weight per week (mg/kg/wk) by simply dividing the total weekly dose by the subject's body weight, such as the subject's ideal body weight. For example, dividing the aforementioned total weekly dose in the first phase by an average adult body weight of 70 kg, in certain embodiments the total weekly dose can be represented as an amount of about 15 mg/70 kg (0.2 mg/kg/wk) to 750 mg/70 kg (10.7 mg/kg/wk). In certain embodiments, the total weekly dose in the first phase can be represented as any of about 15 mg/70 kg (0.2 mg/kg/wk), about 20 mg/70 kg (0.3 mg/kg/wk), about 30 mg/70 kg (0.4 mg/kg/wk), about 40 mg/70 kg (0.6 mg/kg/wk), about 50 mg/70 kg (0.7 mg/kg/wk), about 75 mg/70 kg (1.1 mg/kg/wk), about 100 mg/70 kg (1.4 mg/kg/wk), about 125 mg/70 kg (1.8 mg/kg/wk), about 150 mg/70 kg (2.1 mg/kg/wk), about 175 mg/70 kg (2.5 mg/kg/wk), about 200 mg/70 kg (2.9 mg/kg/wk), about 225 mg/70 kg (3.2 mg/kg/wk), about 250 mg/70 kg (3.6 mg/kg/wk), about 275 mg/70 kg (3.9 mg/kg/wk), about 300 mg/70 kg (4.3 mg/kg/wk), about 325 mg/70 kg (4.6 mg/kg/wk), about 350 mg/70 kg (5.0 mg/kg/wk), about 375 mg/70 kg (5.4 mg/kg/wk), about 400 mg/70 kg (5.7 mg/kg/wk), about 425 mg/70 kg (6.1 mg/kg/wk), about 450 mg/70 kg (6.4 mg/kg/wk), about 475 mg/70 kg (6.8 mg/kg/wk), about 500 mg/70 kg (7.1 mg/kg/wk), about 525 mg/70 kg (7.5 mg/kg/wk), about 550 mg/70 kg (7.9 mg/kg/wk), about 575 mg/70 kg (8.2 mg/kg/wk), about 600 mg/70 kg (8.6 mg/kg/wk), about 625 mg/70 kg (8.9 mg/kg/wk), about 650 mg/70 kg (9.3 mg/kg/wk), about 675 mg/70 kg (9.6 mg/kg/wk), about 700 mg/70 kg (10.0 mg/kg/wk), about 725 mg/70 kg (10.4 mg/kg/wk), or about 750 mg/70 kg (10.7 mg/kg/wk). In certain embodiments, body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet.

In certain embodiments, the second phase comprises administering the compound in 2, 3, 4, 5, 6, or 7 equal doses within a week. In several embodiments, the total weekly dose of the antisense compound in the second phase is an amount of any of about 15 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, or about 250 mg. In certain embodiments, the total weekly dose in the second phase is administered as a single dose per week. It will be understood that the aforementioned total weekly dose ranges in the second phase can be readily represented as milligrams of the antisense compound per kilogram of the subject's body weight per week (mg/kg/wk) by simply dividing the total weekly dose by the subject's body weight, such as the subject's ideal body weight. For example, dividing the aforementioned total weekly dose by an average adult body weight of 70 kg, in certain embodiments the total weekly dose in the second phase can be represented as an amount of about 15 mg/70 kg (0.2 mg/kg/wk) to 250 mg/70 kg (3.6 mg/kg/wk). In certain embodiments, the total weekly dose can be represented as any of about 15 mg/70 kg (0.2 mg/kg/wk), about 20 mg/70 kg (0.3 mg/kg/wk), about 30 mg/70 kg (0.4 mg/kg/wk), about 40 mg/70 kg (0.6 mg/kg/wk), about 50 mg/70 kg (0.7 mg/kg/wk), about 75 mg/70 kg (1.1 mg/kg/wk), about 100 mg/70 kg (1.4 mg/kg/wk), about 125 mg/70 kg (1.8 mg/kg/wk), about 150 mg/70 kg (2.1 mg/kg/wk), about 175 mg/70 kg (2.5 mg/kg/wk), about 200 mg/70 kg (2.9 mg/kg/wk), about 225 mg/70 kg (3.2 mg/kg/wk), or about 250 mg/70 kg (3.6 mg/kg/wk). In certain embodiments, body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet.

In certain embodiments, a method comprises administering to a subject having cancer, such as B-cell lymphoma or HCC, a pharmaceutical composition comprising an antisense compound complementary to a nucleic acid encoding human STAT3, wherein administering the antisense compound comprises:

a first phase for about 6, 7, 8, 9, or 10 weeks, and a second phase comprising a dose of about 2 mg/kg/wk for at least 1 week after the loading phase. In certain embodiments, body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet.

In certain embodiments, a method comprises administering to a subject having cancer, such as B-cell lymphoma or HCC, a pharmaceutical composition comprising an antisense compound complementary to a nucleic acid encoding human STAT3, wherein administering the antisense compound comprises:

a first phase comprising a dose in the range of about 3 to 4 mg/kg/wk for about 6, 7, 8, 9, or 10 weeks, and a second phase comprising a dose of about 2 mg/kg/wk for at least 1 week after the loading phase. In certain embodiments, body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet.

In certain embodiments, a method comprises administering to a subject having cancer, such as B-cell lymphoma or HCC, a pharmaceutical composition comprising an antisense compound complementary to a nucleic acid encoding human STAT3, wherein administering the antisense compound comprises:

a first phase comprising a dose of about 3 mg/kg/wk for about 8 weeks, and a second phase comprising a dose of about 2 mg/kg/wk for at least 1 week after the loading phase. In certain embodiments, body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet.

In any of the above embodiments, the B-cell lymphoma is a non-Hodgkin's B-cell lymphoma. Examples of non-Hodgkin's B-cell lymphoma of certain aspects include, but are not limited to, diffuse large B cell lymphoma (DLBCL), follicular lymphoma, mucosa-associated lymphatic tissue lymphoma (MALT), small cell lymphocytic lymphoma, chronic lymphocytic leukemia, mantle cell lymphoma (MCL), Burkitt lymphoma, mediastinal large B cell lymphoma, Waldenstrim macroglobulinemia, nodal marginal zone B cell lymphoma (NMZL), splenic marginal zone lymphoma (SMZL), intravascular large B-cell lymphoma, primary effusion lymphoma, and lymphomatoid granulomatosis. In certain embodiments, the non-Hodgkin's B-cell lymphoma is diffuse large B cell lymphoma (DLBCL).

In any of the above embodiments, the B-cell lymphoma is Hodgkin's B-cell lymphoma.

In any of the foregoing embodiments, administering the dose of the antisense compound reduces tumor size or tumor volume in the subject. In certain embodiments, administering the dose of the antisense compound prolongs survival of the subject. In certain embodiments, administering the dose of the antisense compound treats cancer, such as B-cell lymphoma, in the subject. In any of the above embodiments, the method is effective to treat cancer and acceptably tolerable in a subject.

In certain of the foregoing embodiments, the subject is identified as having cancer, such as B-cell lymphoma, prior to administering the antisense compound to the subject. In certain embodiments, the subject identified as having cancer, such as B-cell lymphoma, received or is currently receiving anti-cancer treatment, such as a first-line treatment regimen. For example, in certain embodiments the first-line treatment regimen is a combination of cyclophosphamide, hydroxydanuorubicin, oncovin (vincristine), prednisone or prednisolone (CHOP). In certain embodiments, the first-line treatment regimen is a combination of rituximab and CHOP (R-CHOP). In certain embodiments, the subject is refractory to a first-line treatment regimen such as CHOP and/or R-CHOP.

In any of the foregoing embodiments, the antisense compound comprises a modified oligonucleotide consisting of 12 to 30 linked nucleosides having a nucleobase sequence comprising a portion of at least 12 contiguous nucleobases complementary to an equal length portion of nucleobases 3008 to 3033 of SEQ ID NO: 1, wherein the nucleobase sequence is complementary to SEQ ID NO: 1.

In any of the foregoing embodiment, the antisense compound comprises a modified oligonucleotide consisting of 12 to 30 linked nucleosides having a nucleobase sequence comprising a portion of at least 12 contiguous nucleobases complementary to an equal length portion of nucleobases 3016 to 3031 of SEQ ID NO: 1, wherein the nucleobase sequence is complementary to SEQ ID NO: 1.

In any of the foregoing embodiments, the antisense compound comprises a modified oligonucleotide consisting of 12 to 30 linked nucleosides having a nucleobase sequence comprising a portion of at least 12 contiguous nucleobases complementary to an equal length portion of nucleobases 6476 to 6491 of SEQ ID NO: 2, wherein the nucleobase sequence is complementary to SEQ ID NO: 2.

In any of the foregoing embodiments, the antisense compound comprises a modified oligonucleotide consisting of 12 to 30 linked nucleosides having a nucleobase sequence comprising a portion of at least 12 contiguous nucleobases complementary to an equal length portion of nucleobases 250-286; 250-285; 264-285; 264-282; 728-745; 729-745; 729-744; 787-803; 867-883; 955-978; 1146-1170; 1896-1920; 1899-1920; 1899-1919; 1899-1918; 1899-1916; 1901-1916; 1946-1963; 1947-1963; 2155-2205; 2155-2187; 2156-2179; 2204-2221; 2681-2696; 2699-2716; 3001-3033; 3008-3033, 3010-3033, 3010-3032, 3015-3033, 3015-3032, 3015-3031, 3016-3033, 3016-3032, 3016-3033; 3452-3499; 3460-3476; 3583-3608; 3591-3616; 3595-3615; 3595-3614; 3595-3612; 3675-3706; 3713-3790; 3715-3735; 3833-3878;

3889-3932; 3977-4012; 4067-4100; 4225-4256; 4234-4252; 4235-4252; 4235-4251; 4236-4252; 4306-4341; 4431-4456; 4439-4454; 4471-4510; 4488-4505; 4530-4558; 4539-4572; 4541-4558; 4636-4801; 4782-4796; 4800-4823; 4811-4847; 4813-4859; 4813-4815; 4813-4831; 4827-4859; 4827-4844; or 4842-4859 of SEQ ID NO: 1, wherein the nucleobase sequence of the modified oligonucleotide is complementary to SEQ ID NO: 1.

In any of the foregoing embodiments, the antisense compound comprises a modified oligonucleotide consisting of 12 to 30 linked nucleosides having a nucleobase sequence comprising a portion of at least 12 contiguous nucleobases complementary to an equal length portion of nucleobases 2668-2688; 2703-2720; 5000-5021; 5001-5017; 5697-5722; 5699-5716; 6475-6490; 6475-6491; 6476-6491; 7682-7705; 8078-8097; 8079-8095; 9862-9811; 9870-9897; 9875-9893; 9875-9891; 9877-9893; 11699-11719; 12342-12366; 12345-12364; 12346-12364; 12347-12364; 12353-12380; 12357-12376; 12358-12376; 12358-12373; 12360-12376; 14128-14148; 16863-16883; 46091-46111; 50692-50709; 50693-50709; 50693-50708; 61325-61349; 66133-66157; 66136-66157; 66136-66155; 66136-66153; 66138-66153; 66184-66200; 67067-67083; 4171-74220; 74199-74220; 74202-74220; 74171-74219; 74199-74219; 74202-74219; 74171-74218; 74199-74218; 74202-74218; 74723-74768; 74764-74803; 74782-74802; 74782-74801; 74782-74800; 74782-74799; 74783-74802; 74783-74801; 74783-74800; 74783-74799; 74862-74893; 74900-74977; 74902-74922; 74902-74920; 75070-75119; 75164-75199; 75254-75287; 75412-75443; 75421-75439; 75422-75439; 75422-75438; 75423-75439; 75423-75438; 75493-75528; 75616-75643; 75626-75641; 75658-75699; 75676-75692; 75717-75745; 75726-75759; 75726-75745; 75727-75745; 75728-75745; 75831-75988; 75852-75969; 75969-75984; 75987-76056; 76000-76046; 76000-76032; 76000-76018; 76014-76046; 76014-76032; 76029-76046; or 76031-76046 of SEQ ID NO: 2, wherein the nucleobase sequence of the modified oligonucleotide is complementary to SEQ ID NO: 2.

In certain embodiments, the nucleobase sequence of the modified oligonucleotide comprises the sequence of SEQ ID NO: 12 or consists of the sequence of SEQ ID NO: 12. In certain embodiments, the modified oligonucleotide is 100% complementary to SEQ ID NO: 1 or 2.

In certain embodiments, the nucleobase sequence of the modified oligonucleotide comprises the sequence of any of the STAT3 antisense oligonucleotides described in WO 2012/135736, which is incorporated by reference in its entirety herein.

In certain embodiments, the modified oligonucleotide is a single-stranded modified oligonucleotide. In certain embodiments, the modified oligonucleotide comprises at least one modified internucleoside linkage. In several embodiments, each internucleoside linkage is a phosphorothioate internucleoside linkage. In certain embodiments, at least one nucleoside comprises a modified sugar, such as a bicyclic sugar including, but not limited to, a 4'-CH$_2$—O-2' bridge or a 4'-CH(CH$_3$)—O-2' bridge. In certain embodiments, the modified sugar comprises a 2'-O(CH$_2$)$_2$—OCH$_3$ group. In certain embodiments, at least one nucleoside comprises a modified nucleobase, such as a 5-methylcytosine.

In certain embodiments, the modified oligonucleotide comprises:
  a 5'-wing consisting of 1 to 5 linked nucleosides;
  a 3'-wing consisting of 1 to 5 linked nucleosides; and
  a gap between the 5'-wing and the 3'-wing consisting of 8 to 12 linked 2'-deoxynucleosides;

wherein at least one of the 5'-wing and the 3'-wing comprises at least one bicyclic nucleoside or one 2'-substituted nucleoside. In certain embodiments, the 2'-substituted nucleoside comprises a 2'-O(CH$_2$)$_2$—OCH$_3$ group or a 2'-O—CH$_3$ group. In certain embodiments, the bicyclic nucleoside comprises a 4'-CH$_2$—O-2' bridge or a 4'-CH (CH$_3$)—O-2' bridge.

In certain embodiments, pharmaceutical compositions described herein are administered in the form of a dosage unit (e.g., injection, infusion, etc.). In certain embodiments, such pharmaceutical compositions comprise an antisense oligonucleotide in an amount of any of about 15 mg, about 20 mg, about 30 mg, about 40 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, or about 750 mg. It will be understood that the aforementioned amounts of antisense oligonucleotide can be readily represented as milligrams of the antisense compound per kilogram of the subject's body weight per week (mg/kg/wk) by simply dividing the amount by the subject's body weight per week. For example, dividing the aforementioned amounts by an average adult body weight of 70 kg, in certain embodiments the dosage unit can be represented as any of about 15 mg/70 kg (0.2 mg/kg/wk), about 20 mg/70 kg (0.3 mg/kg/wk), about 30 mg/70 kg (0.4 mg/kg/wk), about 40 mg/70 kg (0.6 mg/kg/wk), about 50 mg/70 kg (0.7 mg/kg/wk), about 75 mg/70 kg (1.1 mg/kg/wk), about 100 mg/70 kg (1.4 mg/kg/wk), about 125 mg/70 kg (1.8 mg/kg/wk), about 150 mg/70 kg (2.1 mg/kg/wk), about 175 mg/70 kg (2.5 mg/kg/wk), about 200 mg/70 kg (2.9 mg/kg/wk), about 225 mg/70 kg (3.2 mg/kg/wk), about 250 mg/70 kg (3.6 mg/kg/wk), about 275 mg/70 kg (3.9 mg/kg/wk), about 300 mg/70 kg (4.3 mg/kg/wk), about 325 mg/70 kg (4.6 mg/kg/wk), about 350 mg/70 kg (5.0 mg/kg/wk), about 375 mg/70 kg (5.4 mg/kg/wk), about 400 mg/70 kg (5.7 mg/kg/wk), about 425 mg/70 kg (6.1 mg/kg/wk), about 450 mg/70 kg (6.4 mg/kg/wk), about 475 mg/70 kg (6.8 mg/kg/wk), about 500 mg/70 kg (7.1 mg/kg/wk), about 525 mg/70 kg (7.5 mg/kg/wk), about 550 mg/70 kg (7.9 mg/kg/wk), about 575 mg/70 kg (8.2 mg/kg/wk), about 600 mg/70 kg (8.6 mg/kg/wk), about 625 mg/70 kg (8.9 mg/kg/wk), about 650 mg/70 kg (9.3 mg/kg/wk), about 675 mg/70 kg (9.6 mg/kg/wk), about 700 mg/70 kg (10.0 mg/kg/wk), about 725 mg/70 kg (10.4 mg/kg/wk), or about 750 mg/70 kg (10.7 mg/kg/wk). In certain embodiments, body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet.

In certain embodiments, the antisense oligonucleotide has the nucleobase sequence of SEQ ID NO: 12. In certain embodiments, the antisense oligonucleotide is ISIS 481464.

In certain embodiments, pharmaceutical compositions described herein comprise a dose of antisense oligonucleotide in an amount in the range of about 15 mg, about 20 mg, about 30 mg, about 40 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, or about 750 mg. It will be understood that the aforementioned amounts of antisense oligonucleotide can be readily represented as milligrams of the antisense compound per kilogram of the subject's body weight per week (mg/kg/wk) by simply dividing the amount by the subject's body weight per week. For example, dividing the aforementioned amounts by an average adult body weight of 70 kg, in certain embodiments the dose of antisense oligonucleotide can be represented as any of about 15 mg/70 kg (0.2 mg/kg/wk), about 20 mg/70 kg (0.3 mg/kg/wk), about 30 mg/70 kg (0.4 mg/kg/wk), about 40 mg/70 kg (0.6 mg/kg/wk), about 50 mg/70 kg (0.7 mg/kg/wk), about 75 mg/70 kg (1.1 mg/kg/wk), about 100 mg/70 kg (1.4 mg/kg/wk), about 125 mg/70 kg (1.8 mg/kg/wk), about 150 mg/70 kg (2.1 mg/kg/wk), about 175 mg/70 kg (2.5 mg/kg/wk), about 200 mg/70 kg (2.9 mg/kg/wk), about 225 mg/70 kg (3.2 mg/kg/wk), about 250 mg/70 kg (3.6 mg/kg/wk), about 275 mg/70 kg (3.9 mg/kg/wk), about 300 mg/70 kg (4.3 mg/kg/wk), about 325 mg/70 kg (4.6 mg/kg/wk), about 350 mg/70 kg (5.0 mg/kg/wk), about 375 mg/70 kg (5.4 mg/kg/wk), about 400 mg/70 kg (5.7 mg/kg/wk), about 425 mg/70 kg (6.1 mg/kg/wk), about 450 mg/70 kg (6.4 mg/kg/wk), about 475 mg/70 kg (6.8 mg/kg/wk), about 500 mg/70 kg (7.1 mg/kg/wk), about 525 mg/70 kg (7.5 mg/kg/wk), about 550 mg/70 kg (7.9 mg/kg/wk), about 575 mg/70 kg (8.2 mg/kg/wk), about 600 mg/70 kg (8.6 mg/kg/wk), about 625 mg/70 kg (8.9 mg/kg/wk), about 650 mg/70 kg (9.3 mg/kg/wk), about 675 mg/70 kg (9.6 mg/kg/wk), about 700 mg/70 kg (10.0 mg/kg/wk), about 725 mg/70 kg (10.4 mg/kg/wk), or about 750 mg/70 kg (10.7 mg/kg/wk). In certain embodiments, body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet.

The compositions described herein may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents. However, such materials, when added, should not unduly interfere with the biological activities of the components of the compositions described herein. The formulations can be sterilized and, if desired, mixed with auxiliary agents, e.g., preservatives, stabilizers, wetting agents, emulsifiers, salts for influencing osmotic pressure, buffers, colorings, and/or aromatic substances and the like which do not deleteriously interact with the oligonucleotide(s) of the formulation.

Antisense oligonucleotides may be covalently linked to one or more moieties or conjugates which enhance the activity, cellular distribution or cellular uptake of the antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense oligonucleotides can also be modified to have one or more stabilizing groups that are generally attached to one or both termini of antisense compounds to enhance properties such as, for example, nuclease stability. Included in stabilizing groups are cap structures. These terminal modifications protect the antisense oligonucleotide having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Certain Treatments

In certain aspects there is provided a method of treating a subject suffering from cancer comprising administering to the subject an antisense compound complementary to human STAT3. In certain embodiments the antisense compound complementary to human STAT3 is as described herein or as disclosed in WO2012/135736.

In certain embodiments the cancer is selected from B-cell lymphoma or hepatocellularcarcinoma. In certain aspects there is provided an antisense compound complementary to human STAT3 for use in treating cancer. In certain embodiments the antisense compound complementary to human STAT3 is as described herein or as disclosed in WO2012/135736. In certain embodiments the cancer is selected from B-cell lymphoma or hepatocellularcarcinoma.

In certain aspects there is provided an antisense compound complementary to human STAT3 for use in a method of treating cancer in a subject in need thereof, wherein the method comprises administering to the subject the antisense compound in a loading phase and then a maintenance phase, wherein the loading phase involves administering a total weekly dose of the compound in the range of about 15-750 mg for the first 1-10 weeks, and the maintenance phase involves administering a total weekly dose in the range of 15-250 mg for at least 1 week after the loading phase. In certain embodiments the antisense compound complementary to human STAT3 is as described herein or as disclosed in WO2012/135736. In certain embodiments the cancer is selected from B-cell lymphoma or hepatocellularcarcinoma.

Certain aspects are directed to use of an antisense compound complementary to human STAT3 for the manufacture of a medicament for treating cancer. In certain embodiments the antisense compound complementary to human STAT3 is as described herein or as disclosed in WO2012/135736. In certain embodiments the cancer is selected from B-cell lymphoma or hepatocellularcarcinoma.

In particular embodiments of any of these aspects, the B-cell lymphoma is a non-Hodgkin's B-cell lymphoma. Examples of non-Hodgkin's B-cell lymphoma of certain aspects include, but are not limited to, diffuse large B cell lymphoma (DLBCL), follicular lymphoma, mucosa-associated lymphatic tissue lymphoma (MALT), small cell lymphocytic lymphoma, chronic lymphocytic leukemia, mantle cell lymphoma (MCL), Burkitt lymphoma, mediastinal large B cell lymphoma, Waldenstrom macroglobulinemia, nodal marginal zone B cell lymphoma (NMZL), splenic marginal zone lymphoma (SMZL), intravascular large B-cell lymphoma, primary effusion lymphoma, and lymphomatoid granulomatosis. In certain embodiments, the non-Hodgkin's B-cell lymphoma is diffuse large B cell lymphoma (DLBCL).

Certain Dosing Regimens

In certain embodiments, pharmaceutical compositions are administered according to a dosing regimen. In certain such embodiments, the dosing regimen comprises a loading phase and a maintenance phase. In certain such embodiments, the dosing regimen is effective to treat cancer and acceptably tolerable in a subject. In certain embodiments, the pharmaceutical composition comprises an antisense oligonucleotide. In certain embodiments, the antisense oligonucleotide has the nucleobase sequence of SEQ ID NO: 12. In certain embodiments, the antisense oligonucleotide is ISIS 481464.

In certain embodiments, the loading phase includes 1, 2, 3, 4, 5, 6, 7, 8, 9, 10, 11, 12, 13, 14, 15, 16, 17, 18, 19, or more than 20 doses.

In certain embodiments, the loading phase lasts from 1 day to 6 months. In certain embodiments a loading phase lasts 1 day, 2 days, 3, days, 4, days, 5 days, 6 days, or 7 days as measured from administration of the first dose of the loading phase to administration of the first dose of the maintenance phase. In certain embodiments a loading phase lasts 1 week, 2 weeks, 3, weeks, 4, weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, or 26 weeks as measured from administration of the first dose of the loading phase to administration of the first dose of the maintenance phase. In certain embodiments, the loading phase lasts 1 month, 2 months, 3 months, 4 months, 5 months, or 6 months as measured from administration of the first dose of the loading phase to administration of the first dose of the maintenance phase.

In certain embodiments, the dose administered during the loading phase is lower than the dose administered during the maintenance phase. In certain embodiments, the dose administered during the loading phase is lower than the dose administered during the maintenance phase to avoid undesired side effects. In certain embodiments, the undesired side effect is increased liver markers. In certain embodiments, the undesired side effect is increased ALT. In certain embodiments, the undesired side effect is increased AST. In certain embodiments, the undesired side effect is thrombocytopenia or neutropenia.

In certain embodiments, the dose administered during the loading phase is higher than the dose administered during the maintenance phase. In certain embodiments, the dose administered during the loading phase is higher than the dose administered during the maintenance phase to quickly achieve steady state reduction of STAT3 mRNA expression, STAT3 protein expression, and/or STAT3 activity. In certain embodiments, the dose administered during the loading phase is higher than the dose administered during the maintenance phase to avoid undesired side effects in the maintenance phase. In certain embodiments, the undesired side effect is increased liver markers. In certain embodiments, the undesired side effect is increased ALT. In certain embodiments, the undesired side effect is increased AST. In certain embodiments, the undesired side effect is thrombocytopenia or neutropenia.

In certain embodiments where the loading phase includes more than one dose, the doses administered during the loading phase are all the same amount as one another. In certain embodiments, the doses administered during the loading phase are not all the same amount. In certain embodiments, the doses given during the loading phase increase over time. In certain embodiments, the doses given during the loading phase decrease over time.

In certain embodiments, a loading dose is administered by parenteral administration. In certain embodiments, the parenteral administration is subcutaneous administration. In certain embodiments, the parenteral administration is intravenous infusion.

In certain embodiments, the doses administered during the loading phase are about 0.2 mg, about 0.3 mg, about 0.4 mg, about 0.5 mg, about 0.6 mg, about 0.7 mg, about 0.8 mg, about 0.9 mg, about 1.0 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, about 2.1 mg, about 2.2 mg, about 2.3 mg, about 2.4 mg, about 2.5 mg, about 2.6 mg, about 2.7 mg, about 2.8 mg, about 2.9 mg, about 3.0 mg, about 3.1 mg, about 3.2 mg, about 3.3 mg, about 3.4 mg, or about 3.5 mg of the antisense compound per kilogram of the subject's body weight. In certain embodiments, the dose is 2.0 milligrams of the antisense compound per kilogram of the subject's body weight per week (2.0 mg/kg/wk). In certain embodiments, the subject's body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet.

In certain embodiments, the doses administered during the loading phase are about 15 mg, about 20 mg, about 30 mg, about 40 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, or about 750 mg. It will be understood that the aforementioned doses of antisense oligonucleotide can be readily represented as milligrams of the antisense compound per kilogram of the subject's body weight per week (mg/kg/wk) by simply dividing the amount by the subject's body weight per week. For example, dividing the aforementioned amounts by an average adult body weight of 70 kg, in certain embodiments the doses can be represented as any of about 15 mg/70 kg (0.2 mg/kg/wk), about 20 mg/70 kg (0.3 mg/kg/wk), about 30 mg/70 kg (0.4 mg/kg/wk), about 40 mg/70 kg (0.6 mg/kg/wk), about 50 mg/70 kg (0.7 mg/kg/wk), about 75 mg/70 kg (1.1 mg/kg/wk), about 100 mg/70 kg (1.4 mg/kg/wk), about 125 mg/70 kg (1.8 mg/kg/wk), about 150 mg/70 kg (2.1 mg/kg/wk), about 175 mg/70 kg (2.5 mg/kg/wk), about 200 mg/70 kg (2.9 mg/kg/wk), about 225 mg/70 kg (3.2 mg/kg/wk), about 250 mg/70 kg (3.6 mg/kg/wk), about 275 mg/70 kg (3.9 mg/kg/wk), about 300 mg/70 kg (4.3 mg/kg/wk), about 325 mg/70 kg (4.6 mg/kg/wk), about 350 mg/70 kg (5.0 mg/kg/wk), about 375 mg/70 kg (5.4 mg/kg/wk), about 400 mg/70 kg (5.7 mg/kg/wk), about 425 mg/70 kg (6.1 mg/kg/wk), about 450 mg/70 kg (6.4 mg/kg/wk), about 475 mg/70 kg (6.8 mg/kg/wk), about 500 mg/70 kg (7.1 mg/kg/wk), about 525 mg/70 kg (7.5 mg/kg/wk), about 550 mg/70 kg (7.9 mg/kg/wk), about 575 mg/70 kg (8.2 mg/kg/wk), about 600 mg/70 kg (8.6 mg/kg/wk), about 625 mg/70 kg (8.9 mg/kg/wk), about 650 mg/70 kg (9.3 mg/kg/wk), about 675 mg/70 kg (9.6 mg/kg/wk), about 700 mg/70 kg (10.0 mg/kg/wk), about 725 mg/70 kg (10.4 mg/kg/wk), or about 750 mg/70 kg (10.7 mg/kg/wk). In certain embodiments, body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet.

In certain embodiments, dose, dose frequency, and duration of the loading phase may be selected to achieve a desired effect. In certain embodiments, those variables are adjusted to result in a desired concentration of pharmaceutical agent in a subject. For example, in certain embodiments, dose and dose frequency are adjusted to provide plasma concentration of a pharmaceutical agent at an amount sufficient to achieve a desired effect. In certain embodiments, the plasma concentration is maintained above the minimal effective concentration (MEC). In certain embodiments, pharmaceutical compositions described herein are administered with a dosage regimen designed to maintain a concentration above the MEC for 10-90% of the time, between 30-90% of the time, or between 50-90% of the time. In certain embodiments, the pharmaceutical composition comprises an antisense oligonucleotide. In certain embodiments, the antisense oligonucleotide has the nucleobase sequence of SEQ ID NO: 12. In certain embodiments, the antisense oligonucleotide is ISIS 481464.

In certain embodiments, doses, dose frequency, and duration of the loading phase may be selected to achieve a desired plasma trough concentration of a pharmaceutical composition. In certain embodiments, the pharmaceutical composition comprises an antisense oligonucleotide. In certain embodiments, the antisense oligonucleotide has the nucleobase sequence of SEQ ID NO: 12. In certain embodiments, the antisense oligonucleotide is ISIS 481464. In certain embodiments, the desired plasma trough concentration is from 5-100 ng/mL. In certain embodiments, the desired plasma trough concentration is from 5-50 ng/mL. In certain embodiments, the desired plasma trough concentration is from 10-40 ng/mL. In certain embodiments, the desired plasma trough concentration is from 15-35 ng/mL. In certain embodiments, the desired plasma trough concentration is from 20-30 ng/mL.

In certain embodiments, dose, dose frequency, and duration of the loading phase may be selected to achieve a desired effect within 1 to 26 weeks. In certain embodiments, the dose is the same and the dose frequency is varied to achieve the desired effect within 1 to 26 weeks. In certain embodiments, the dose increases over time and the dose frequency remains constant. In certain embodiments, one or more doses of the loading phase are greater than one or more doses of the maintenance phase. In certain embodiments, each of the loading doses is greater than each of the maintenance doses. In certain embodiments, it is desirable to achieve a desired effect as quickly as possible. In certain embodiments, a loading phase with a high dose and/or high dose frequency may be desirable.

In certain embodiments, doses, dose frequency, and duration of the loading phase may be selected to achieve an acceptable safety profile. For example, in certain embodiments, such variables may be selected to mitigate toxicity of the pharmaceutical composition. In certain embodiments, such variables are selected to mitigate liver toxicity. In certain embodiments, such variables are selected to mitigate renal toxicity. In certain embodiments, such variables are selected to mitigate thrombocytopenia or neutropenia.

In certain embodiments, doses increase over time. In certain embodiments, one or more doses of the loading phase are lower than one or more doses of the maintenance phase. In certain embodiments, a safety profile is not acceptable when ALT is 5-10 times the upper limit of normal. In certain embodiments, a safety profile is not acceptable when ALT is 5-10 times the upper limit of normal, and bilirubin is elevated two or more times the upper limit of normal. In certain embodiments, an acceptable safety profile comprises ALT elevations that are above three times the upper limit of normal, but do not exceed five times the upper limit of normal. In certain embodiments, an acceptable safety profile comprises ALT elevations that are above three times the upper limit of normal, but do not exceed five times the upper limit of normal, and bilirubin elevations that do not exceed two times the upper limit of normal. In certain embodiments, when administration of a pharmaceutical composition of the invention results in ALT elevations that are above three times the upper limit of normal, the dose and/or dose frequency is adjusted to mitigate the ALT elevation.

In certain embodiments, the maintenance phase includes 1, 2, 3, 4, 5, 6, 7, 8, 9, 10, 11, 12, 13, 14, 15, 16, 17, 18, 19, 20, or more than 20 doses.

In certain embodiments, the maintenance phase lasts from one day to the lifetime of the subject. In certain embodiments, the maintenance phase lasts 1 day, 2 days, 3 days, 4 days, 5 days, 6 days, or 7 days as measured from administration of the last dose of the loading phase to administration of the last dose of the maintenance phase. In certain embodiments, the maintenance phase lasts 1 week, 2 weeks, 3, weeks, 4, weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, or 52 weeks as measured from administration of the last dose of the loading phase to administration of the last dose of the maintenance phase. In certain embodiments, the maintenance phase lasts 1 month, 2 months, 3 months, 4 months, 5 months, 6 months, 7 months, 8 months, 9 months, 10 months, 11 months, or 12 months as measured from administration of the last dose of the loading phase to administration of the last dose of the maintenance phase. In certain embodiments, the maintenance phase lasts 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 21 years, 22 years, 23 years, 24 years, 25 years, 26 years, 27 years, 28 years, 29 years, 30 years, 31 years, 32 years, 33 years, 34 years 35 years, 36 years, 37 years, 38 years, 39 years, 40 years, 41 years, 42 years, 43 years, 44 years, 45 years, 46 years, 47 years, 48 years, 49 years, or 50 years as measured from administration of the last dose of the loading phase to administration of the last dose of the maintenance phase. In certain embodiments, the maintenance phase lasts as long as the dose continues to be needed, effective, and tolerated.

In certain embodiments where the maintenance phase includes more than one dose, the doses administered during the maintenance phase are all the same as one another. In certain embodiments, the doses administered during the maintenance phase are not all the same. In certain embodiments, the doses increase over time. In certain embodiments, the doses decrease over time.

In certain embodiments, a maintenance dose is administered by parenteral administration. In certain embodiments, the parenteral administration is subcutaneous administration. In certain embodiments, the parenteral administration is intravenous infusion.

In certain embodiments, the doses during the maintenance phase are about 0.2 mg, about 0.3 mg, about 0.4 mg, about 0.5 mg, about 0.6 mg, about 0.7 mg, about 0.8 mg, about 0.9 mg, about 1.0 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, about 2.1 mg, about 2.2 mg, about 2.3 mg, about 2.4 mg, about 2.5 mg, about 2.6 mg, about 2.7 mg, about 2.8 mg, about 2.9 mg, about 3.0 mg, about 3.1 mg, about 3.2 mg, about 3.3 mg, about 3.4 mg, or about 3.5 mg of the antisense compound per kilogram of the subject's body weight. In certain embodiments, the dose is 2.0 milligrams of the antisense compound per kilogram of the subject's body weight per week (2.0 mg/kg/wk). In certain embodiments, the subject's body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet.

In certain embodiments, the doses during the maintenance phase are about 15 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, or about 250 mg. It will be understood that the aforementioned doses of antisense oligonucleotide can be readily represented as milligrams of the antisense compound per kilogram of the subject's body weight per week (mg/kg/wk) by simply dividing the amount by the subject's body weight per week. For example, dividing the aforementioned amounts by an average adult body weight of 70 kg, in certain embodiments the doses can be represented as any of about 15 mg/70 kg (0.2 mg/kg/wk), about 20 mg/70 kg (0.3 mg/kg/wk), about 30 mg/70 kg (0.4 mg/kg/wk), about 40 mg/70 kg (0.6 mg/kg/wk), about 50 mg/70 kg (0.7 mg/kg/wk), about 75 mg/70 kg (1.1 mg/kg/wk), about 100 mg/70 kg (1.4 mg/kg/wk), about 125 mg/70 kg (1.8 mg/kg/wk), about 150 mg/70 kg (2.1 mg/kg/wk), about 175 mg/70 kg (2.5 mg/kg/wk), about 200 mg/70 kg (2.9 mg/kg/wk), about 225 mg/70 kg (3.2 mg/kg/wk), or about 250 mg/70 kg (3.6 mg/kg/wk). In certain embodiments, body weight is calculated as the ideal body weight using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet.

In certain embodiments, doses, dose frequency, and duration of the maintenance phase may be selected to achieve a desired effect. In certain embodiments, those variables are adjusted to result in a desired concentration of pharmaceutical agent in a subject. For example, in certain embodiments, dose and dose frequency are adjusted to provide plasma concentration of a pharmaceutical agent described herein at an amount sufficient to achieve a desired effect. In certain embodiments, the plasma concentration is maintained above the minimal effective concentration (MEC). In certain embodiments, pharmaceutical compositions described herein are administered with a dosage regimen designed to maintain a concentration above the MEC for 10-90% of the time, between 30-90% of the time, or between 50-90% of the time.

In certain embodiments, doses, dose frequency, and duration of the maintenance phase may be selected to achieve a desired plasma trough concentration of a pharmaceutical composition. In certain embodiments, the pharmaceutical composition is an antisense oligonucleotide. In certain embodiments, the desired plasma trough concentration is from 5-100 ng/mL. In certain embodiments, the desired plasma trough concentration is from 5-50 ng/mL. In certain embodiments, the desired plasma trough concentration is from 10-40 ng/mL. In certain embodiments, the desired plasma trough concentration is from 15-35 ng/mL. In certain embodiments, the desired plasma trough concentration is from 20-30 ng/mL.

In certain embodiments, doses, dose frequency, and duration of the maintenance phase may be selected to achieve a desired safety profile. For example, in certain embodiments, such variables may be selected to mitigate toxicity of the pharmaceutical composition. In certain embodiments, such variables are selected to mitigate liver toxicity. In certain embodiments, such variables are selected to mitigate renal toxicity. In certain embodiments, such variables are selected to mitigate thrombocytopenia or neutropenia.

In certain embodiments, doses, dose frequency, and duration of the maintenance phase may be adjusted from time to time to achieve a desired effect. In certain embodiments, subjects are monitored for effects (therapeutic and/or toxic effects) and doses, dose frequency, and/or duration of the maintenance phase may be adjusted based on the results of such monitoring.

In certain embodiments, pharmaceutical compositions are administered according to a dosing regimen comprising a first phase and a second phase. In certain embodiments, the pharmaceutical composition comprises an antisense oligonucleotide. In certain embodiments, the antisense oligonucleotide has the nucleobase sequence of SEQ ID NO: 12. In certain embodiments, the antisense oligonucleotide is ISIS 481464.

In certain embodiments, the first phase includes 1, 2, 3, 4, 5, 6, 7, 8, 9, 10, 11, 12, 13, 14, 15, 16, 17, 18, 19, or more than 20 doses.

In certain embodiments, the first phase lasts from 1 day to 6 months. In certain embodiments a first phase lasts 1 day, 2 days, 3, days, 4, days, 5 days, 6 days, or 7 days as measured from administration of the first dose of the first phase to administration of the first dose of the second phase. In certain embodiments a first phase lasts 1 week, 2 weeks, 3, weeks, 4, weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, or 26 weeks as measured from administration of the first dose of the first phase to administration of the first dose of the second phase. In certain embodiments, the first phase lasts 1 month, 2 months, 3 months, 4 months, 5 months, or 6 months as measured from administration of the first dose of the first phase to administration of the first dose of the second phase.

In certain embodiments, the dose administered during the first phase is lower than the dose administered during the second phase. In certain embodiments, the dose administered during the first phase is lower than the dose administered during the second phase to avoid undesired side effects. In certain embodiments, the undesired side effect is increased liver markers. In certain embodiments, the undesired side effect is increased ALT. In certain embodiments, the undesired side effect is increased AST. In certain embodiments, the undesired side effect is thrombocytopenia or neutropenia.

In certain embodiments, the dose administered during the first phase is higher than the dose administered during the second phase. In certain embodiments, the dose administered during the first phase is higher than the dose administered during the second phase to quickly achieve steady state reduction of STAT3 mRNA expression, STAT3 protein expression, and/or STAT3 activity. In certain embodiments, the dose administered during the first phase is higher than the dose administered during the second phase to avoid undesired side effects in the second phase. In certain embodiments, the undesired side effect is increased liver markers. In certain embodiments, the undesired side effect is increased ALT. In certain embodiments, the undesired side effect is increased AST. In certain embodiments, the undesired side effect is thrombocytopenia or neutropenia.

In certain embodiments where the first phase includes more than one dose, the doses administered during the first phase are all the same amount as one another. In certain embodiments, the doses administered during the first phase are not all the same amount. In certain embodiments, the doses given during the first phase increase over time. In certain embodiments, the doses given during the first phase decrease over time.

In certain embodiments, a first dose is administered by parenteral administration. In certain embodiments, the parenteral administration is subcutaneous administration. In certain embodiments, the parenteral administration is intravenous infusion.

The range of dosages capable of being administered during the "first phase" and/or "second phase" are the same as can be used for the "loading phase" and "maintenance phase" referred to above. In certain embodiments, dose, dose frequency, and duration of the first phase and/or second phase may be selected to achieve a desired effect. In certain embodiments, those variables are adjusted to result in a desired concentration of pharmaceutical agent in a subject. For example, in certain embodiments, dose and dose frequency are adjusted to provide plasma concentration of a pharmaceutical agent at an amount sufficient to achieve a desired effect. In certain embodiments, the plasma concentration is maintained above the minimal effective concentration (MEC). In certain embodiments, pharmaceutical compositions described herein are administered with a dosage regimen designed to maintain a concentration above the MEC for 10-90% of the time, between 30-90% of the time, or between 50-90% of the time. In certain embodiments, the pharmaceutical composition comprises an antisense oligonucleotide. In certain embodiments, the antisense oligonucleotide has the nucleobase sequence of SEQ ID NO: 12. In certain embodiments, the antisense oligonucleotide is ISIS 481464. In certain embodiments, doses, dose frequency, and duration of the first phase and/or second phase may be selected to achieve a desired plasma trough concentration of a pharmaceutical composition. In certain embodiments, the pharmaceutical composition comprises an antisense oligonucleotide. In certain embodiments, the antisense oligonucleotide has the nucleobase sequence of SEQ ID NO: 12. In certain embodiments, the antisense oligonucleotide is ISIS 481464. In certain embodiments, the desired plasma trough concentration is from 5-100 ng/mL. In certain embodiments, the desired plasma trough concentration is from 5-50 ng/mL. In certain embodiments, the desired plasma trough concentration is from 10-40 ng/mL. In certain embodiments, the desired plasma trough concentration is from 15-35 ng/mL. In certain embodiments, the desired plasma trough concentration is from 20-30 ng/mL.

In certain embodiments, dose, dose frequency, and duration of the first phase and/or second phase may be selected to achieve a desired effect within 1 to 26 weeks. In certain embodiments, the dose is the same and the dose frequency is varied to achieve the desired effect within 1 to 26 weeks. In certain embodiments, the dose increases over time and the dose frequency remains constant. In certain embodiments, one or more doses of the first phase are greater than one or more doses of the second phase. In certain embodiments, each of the first doses is greater than each of the second doses. In certain embodiments, it is desirable to achieve a desired effect as quickly as possible. In certain embodiments, a first phase with a high dose and/or high dose frequency may be desirable. In certain embodiments, doses, dose frequency, and duration of the first phase and/or second phase may be selected to achieve an acceptable safety profile. For example, in certain embodiments, such variables may be selected to mitigate toxicity of the pharmaceutical composition. In certain embodiments, such variables are selected to mitigate liver toxicity. In certain embodiments, such variables are selected to mitigate renal toxicity. In certain embodiments, such variables are selected to mitigate thrombocytopenia or neutropenia.

In certain embodiments, doses increase over time. In certain embodiments, one or more doses of the first phase are lower than one or more doses of the second phase. In certain embodiments, a safety profile is not acceptable when ALT is 5-10 times the upper limit of normal. In certain embodiments, a safety profile is not acceptable when ALT is 5-10 times the upper limit of normal, and bilirubin is elevated two or more times the upper limit of normal. In certain embodiments, an acceptable safety profile comprises ALT elevations that are above three times the upper limit of normal, but do not exceed five times the upper limit of normal. In certain embodiments, an acceptable safety profile comprises ALT elevations that are above three times the upper limit of normal, but do not exceed five times the upper limit of normal, and bilirubin elevations that do not exceed two times the upper limit of normal. In certain embodiments, when administration of a pharmaceutical composition of the invention results in ALT elevations that are above three times the upper limit of normal, the dose and/or dose frequency is adjusted to mitigate the ALT elevation. In certain embodiments, the second phase includes 1, 2, 3, 4, 5, 6, 7, 8, 9, 10, 11, 12, 13, 14, 15, 16, 17, 18, 19, 20, or more than 20 doses. In certain embodiments, the second phase lasts from one day to the lifetime of the subject. In certain embodiments, the second phase lasts 1 day, 2 days, 3 days, 4 days, 5 days, 6 days, or 7 days as measured from administration of the last dose of the first phase to administration of the last dose of the second phase. In certain embodiments, the second phase lasts 1 week, 2 weeks, 3, weeks, 4, weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, or 52 weeks as measured from administration of the last dose of the first phase to administration of the last dose of the second phase. In certain embodiments, the second phase lasts 1 month, 2 months, 3 months, 4 months, 5 months, 6 months, 7 months, 8 months, 9 months, 10 months, 11 months, or 12 months as measured from administration of the last dose of the first phase to administration of the last dose of the second phase. In certain embodiments, the second phase lasts 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 21 years, 22 years, 23 years, 24 years, 25 years, 26 years, 27 years, 28 years, 29 years, 30 years, 31 years, 32 years, 33 years, 34 years 35 years, 36 years, 37 years, 38 years, 39 years, 40 years, 41 years, 42 years, 43 years, 44 years, 45 years, 46 years, 47 years, 48 years, 49 years, or 50 years as measured from administration of the last dose of the first phase to administration of the last dose of the second phase. In certain embodiments, the second phase lasts as long as the dose continues to be needed, effective, and tolerated.

In certain embodiments where the second phase includes more than one dose, the doses administered during the second phase are all the same as one another. In certain embodiments, the doses administered during the second phase are not all the same. In certain embodiments, the doses increase over time. In certain embodiments, the doses decrease over time.

In certain embodiments, a second dose is administered by parenteral administration. In certain embodiments, the parenteral administration is subcutaneous administration. In certain embodiments, the parenteral administration is intravenous infusion.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a STAT3 nucleic acid is 12 to 30 subunits in length. In certain embodiments, an antisense compound targeted to a STAT3 nucleic acid is 14 to 30 subunits in length. In certain embodiments, an antisense compound targeted to a STAT3 nucleic acid is 12 to 22 subunits in length. In other words, such antisense compounds are from 12 to 30 linked subunits, 14 to 30 linked subunits, or 12 to 22 linked subunits, respectively. In other embodiments, the antisense compound is 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments, the antisense compound is an antisense oligonucleotide, and the linked subunits are nucleotides.

In certain embodiments, antisense oligonucleotides targeted to a STAT3 nucleic acid may be shortened or truncated. For example, a single subunit may be deleted from the 5' end (5' truncation), or alternatively from the 3' end (3' truncation). A shortened or truncated antisense compound targeted to a STAT3 nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al. (*J. Natl. Cancer Inst.* 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (*Nuc. Acid. Res.* 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a STAT3 nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE and 2'-O—$CH_3$, among others), and bicyclic sugar modified nucleosides (such bicyclic sugar modified nucleosides may include those having a constrained ethyl). In certain embodiments, wings may include several modified sugar moieties, including, for example 2'-MOE and constrained ethyl. In certain embodiments, wings may include several modified and unmodified sugar moieties. In certain embodiments, wings may include various combinations of 2'-MOE nucleosides, constrained ethyl nucleosides, and 2'-deoxynucleosides.

Each distinct region may comprise uniform sugar moieties, variants, or alternating sugar moieties. The wing-gap-wing motif is frequently described as "X-Y-Z", where "X" represents the length of the 5'-wing, "Y" represents the length of the gap, and "Z" represents the length of the 3'-wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X-Y-Z" has a configuration such that the gap is positioned immediately adjacent to each of the 5'-wing and the 3' wing. Thus, no intervening nucleotides exist between the 5'-wing and gap, or the gap and the 3'-wing. Any of the antisense compounds described herein can have a gapmer motif. In certain embodiments, "X" and "Z" are the same, in other embodiments they are different. In certain embodiments, "Y" is between 8 and 15 nucleosides. X, Y, or Z can be any of 1, 2, 3, 4, 5, 6, 7, 8, 9, 10, 11, 12, 13, 14, 15, 16, 17, 18, 19, 20, 25, 30 or more nucleosides.

In certain embodiments, gapmers provided herein include, for example, 11-mers having a motif of 1-9-1.

In certain embodiments, gapmers provided herein include, for example, 12-mers having a motif of 1-9-2, 2-9-1, or 1-10-1.

In certain embodiments, gapmers provided herein include, for example, 13-mers having a motif of 1-9-3, 2-9-2, 3-9-1, 1-10-2, or 2-10-1.

In certain embodiments, gapmers provided herein include, for example, 14-mers having a motif of 1-9-4, 2-9-3, 3-9-2, 4-9-1, 1-10-3, 2-10-2, or 3-10-1.

In certain embodiments, gapmers provided herein include, for example, 15-mers having a motif of 1-9-5, 2-9-4, 3-9-3, 4-9-2, 5-9-1, 1-10-4, 2-10-3, 3-10-2, or 4-10-1.

In certain embodiments, gapmers provided herein include, for example, 16-mers having a motif of 2-9-5, 3-9-4, 4-9-3, 5-9-2, 1-10-5, 2-10-4, 3-10-3, 4-10-2, or 5-10-1.

In certain embodiments, gapmers provided herein include, for example, 17-mers having a motif of 3-9-5, 4-9-4, 5-9-3, 2-10-5, 3-10-4, 4-10-3, or 5-10-2.

In certain embodiments, gapmers provided herein include, for example, 18-mers having a motif of 4-9-5, 5-9-4, 3-10-5, 4-10-4, or 5-10-3.

In certain embodiments, gapmers provided herein include, for example, 19-mers having a motif of 5-9-5, 4-10-5, or 5-10-4.

In certain embodiments, gapmers provided herein include, for example, 20-mers having a motif of 5-10-5.

In certain embodiments, the antisense compound has a "wingmer" motif, having a wing-gap or gap-wing configuration, i.e. an X-Y or Y-Z configuration as described above for the gapmer configuration. Thus, wingmer configurations provided herein include, but are not limited to, for example 5-10, 8-4, 4-12, 12-4, 3-14, 16-2, 18-1, 10-3, 2-10, 1-10, 8-2, 2-13, 5-13, 5-8, or 6-8.

In certain embodiments, antisense compound targeted to a STAT3 nucleic acid has a 2-10-2 gapmer motif.

In certain embodiments, the antisense compound targeted to a STAT3 nucleic acid has a 3-10-3 gapmer motif.

In certain embodiments, the antisense compound targeted to a STAT3 nucleic acid has a 5-10-5 gapmer motif.

In certain embodiments, the antisense compound targeted to a STAT3 nucleic acid has a 1-10-5 gapmer motif.

In certain embodiments, the antisense compound targeted to a STAT3 nucleic acid has a 3-10-4 gapmer motif.

In certain embodiments, the antisense compound targeted to a STAT3 nucleic acid has a 2-10-4 gapmer motif.

In certain embodiments, the antisense compound targeted to a STAT3 nucleic acid has a 4-9-3 gapmer motif.

In certain embodiments, the antisense compound targeted to a STAT3 nucleic acid has a gap-widened motif.

In certain embodiments, the antisense compounds targeted to a STAT3 nucleic acid has any of the following sugar motifs:

k-d(10)-k
e-d(10)-k
k-d(10)-e
k-k-d(10)-k-k
k-k-d(10)-e-e
e-e-d(10)-k-k
k-k-k-d(10)-k-k-k
e-e-e-d(10)-k-k-k
k-k-k-d(10)-e-e-e
k-k-k-d(10)-k-k-k
e-k-k-d(10)-k-k-e
e-e-k-d(10)-k-k-e
e-d-k-d(10)-k-k-e
e-k-d(10)-k-e-k-e
k-d(10)-k-e-k-e-e
e-e-k-d(10)-k-e-k-e
e-d-d-k-d(9)-k-k-e
e-e-e-e-d(9)-k-k-e wherein, k is a constrained ethyl nucleoside, e is a 2'-MOE substituted nucleoside, and d is a 2'-deoxynucleoside.

In certain embodiments, the antisense oligonucleotide has a sugar motif described by Formula A as follows:
$(J)_m$-$(B)_n$-$(J)_p$-$(B)_r$-$(A)_t$-$(D)_g$-$(A)_v$-$(B)_w$-$(J)_x$-$(B)_y$-$(J)_z$ wherein:
each A is independently a 2'-substituted nucleoside;
each B is independently a bicyclic nucleoside;
each J is independently either a 2'-substituted nucleoside or a 2'-deoxynucleoside;
each D is a 2'-deoxynucleoside;
m is 0-4; n is 0-2; p is 0-2; r is 0-2; t is 0-2; v is 0-2; w is 0-4; x is 0-2; y is 0-2; z is 0-4; g is 6-14;
provided that:
at least one of m, n, and r is other than 0;
at least one of w and y is other than 0;
the sum of m, n, p, r, and t is from 2 to 5; and
the sum of v, w, x, y, and z is from 2 to 5.

Target Nucleic Acids, Target Regions and Nucleotide Sequences

Nucleotide sequences that encode STAT3 include, without limitation, the following: GENBANK Accession No. NM_139276.2 (incorporated herein as SEQ ID NO: 1) and the complement of GENBANK Accession No. NT_010755.14 truncated from nucleotides 4185000 to U.S. Pat. No. 4,264,000 (incorporated herein as SEQ ID NO: 2).

It is understood that the sequence set forth in each SEQ ID NO contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for STAT3 can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in STAT3 mRNA levels are indicative of inhibition of STAT3 expression. Reductions in levels of a STAT3 protein are also indicative of inhibition of target mRNA expression. Further, phenotypic changes are indicative of inhibition of STAT3 expression. In certain embodiments, reduced cellular growth, reduced tumor growth, and reduced tumor volume can be indicative of inhibition of STAT3 expression. In certain embodiments, amelioration of symptoms associated with cancer can be indicative of inhibition of STAT3 expression. In certain embodiments, reduction of cachexia is indicative of inhibition of STAT3 expression. In certain embodiments, reduction of cancer markers can be indicative of inhibition of STAT3 expression.

Hybridization

In some embodiments, hybridization occurs between an antisense compound disclosed herein and a STAT3 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a STAT3 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a STAT3 nucleic acid).

Non-complementary nucleobases between an antisense compound and a STAT3 nucleic acid may be tolerated provided that the antisense compound remains able to specifically hybridize to a target nucleic acid. Moreover, an antisense compound may hybridize over one or more segments of a STAT3 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a STAT3 nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having four non-complementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.*, 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, an antisense compound may be fully complementary to a STAT3 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a STAT3 nucleic acid, or specified portion thereof.

In certain embodiments, antisense compounds that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a STAT3 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds are complementary to at least an 11 nucleobase portion of a target segment. In certain embodiments, the antisense compounds are complementary to at least a 12 nucleobase portion of a target segment. In certain embodiments, the antisense compounds are complementary to at least a 13 nucleobase portion of a target segment. In certain embodiments, the antisense compounds are complementary to at least a 14 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occuring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a STAT3 nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds provided herein can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise a chemically modified ribofuranose ring moiety. Examples of chemically modified ribofuranose rings include, without limitation, addition of substituent groups (including 5' and 2' substituent groups); bridging of non-geminal ring atoms to form bicyclic nucleic acids (BNA); replacement of the ribosyl ring oxygen atom with S, N(R), or C(R1)(R)2 (R=H, $C_1$-$C_{12}$ alkyl or a protecting group); and combinations thereof. Examples of chemically modified sugars include, 2'-F-5'-methyl substituted nucleoside (see, PCT International Application WO 2008/101157, published on Aug. 21, 2008 for other disclosed 5', 2'-bis substituted nucleosides), replacement of the ribosyl ring oxygen atom with S with further substitution at the 2'-position (see, published U.S. Patent Application US2005/0130923, published on Jun. 16, 2005), or, alternatively, 5'-substitution of a BNA (see, PCT International Application WO 2007/134181, published on Nov. 22, 2007, wherein LNA is substituted with, for example, a 5'-methyl or a 5'-vinyl group).

Examples of nucleosides having modified sugar moieties include, without limitation, nucleosides comprising 5'-vinyl, 5'-methyl (R or S), 4'-S, 2'-F, 2'-$OCH_3$, and 2'-O($CH_2$)$_2OCH_3$ substituent groups. The substituent at the 2' position can also be selected from allyl, amino, azido, thio, O-allyl, O—$C_1$-$C_{10}$ alkyl, $OCF_3$, O($CH_2$)$_2$$SCH_3$, O($CH_2$)$_2$—O—N(Rm)(Rn), and O—$CH_2$—C(=O)—N(Rm)(Rn), where each Rm and Rn is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include, without limitation, nucleosides comprising a bridge between the 4' and the 2' ribosyl ring atoms. In certain embodiments, antisense compounds provided herein include one or more bicyclic nucleosides wherein the bridge comprises a 4' to 2' bicyclic nucleoside. Examples of such 4' to 2' bicyclic nucleosides, include, but are not limited to, one of the formulae: 4'-($CH_2$)—O-2' (LNA); 4'-($CH_2$)—S-2'; 4'-($CH_2$)$_2$—O-2' (ENA); 4'—CH($CH_3$)—O-2' and 4'-C—H($CH_2OCH_3$)—O-2', and analogs thereof (see, U.S. Pat. No. 7,399,845, issued on Jul. 15, 2008); 4'-C($CH_3$)($CH_3$)—O-2', and analogs thereof (see, published PCT International Application WO2009/006478, published Jan. 8, 2009); 4'-$CH_2$—N($OCH_3$)-2', and analogs thereof (see, published PCT International Application WO2008/150729, published Dec. 11, 2008); 4'-$CH_2$-O—N($CH_3$)-2' (see, published U.S. Patent Application US2004/0171570, published Sep. 2, 2004); 4'-$CH_2$—N(R)—O-2', wherein R is H, $C_1$-$C_{12}$ alkyl, or a protecting group (see, U.S. Pat. No. 7,427,672, issued on Sep. 23, 2008); 4'-$CH_2$—C(H)($CH_3$)-2' (see, Chattopadhyaya, et al., *J. Org. Chem.*, 2009, 74, 118-134); and 4'-$CH_2$—C(=$CH_2$)-2', and analogs thereof (see, published PCT International Application WO 2008/154401, published on Dec. 8, 2008). Also see, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 6,670,461, 7,053,207, 6,268,490, 6,770,748, 6,794,499, 7,034,133, 6,525,191, 7,399,845; published PCT International applications WO 2004/106356, WO 94/14226, WO 2005/021570, and WO 2007/134181; U.S. Patent Publication Nos. US2004/0171570, US2007/0287831, and US2008/0039618; and U.S. patent Ser. Nos. 12/129,154, 60/989,574, 61/026,995, 61/026,998, 61/056,564, 61/086,231, 61/097,787, and 61/099,844; and PCT International Application Nos. PCT/US2008/064591, PCT/US2008/066154, and PCT/US2008/068922. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C($R_a$)($R_b$)]$_n$—, —C($R_a$)=C($R_b$)—, —C($R_a$)=N—, —C(=$NR_a$)—, —C(=O)—, —C(=S)—, —O—, —Si($R_a$)$_2$—, —S(=O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

In certain embodiments, the bridge of a bicyclic sugar moiety is, —[C($R_a$)($R_b$)]$_n$—, —[C($R_a$)($R_b$)]n-O—, —C($R_aR_b$)—N(R)—O— or, —C($R_aR_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2', and 4'-CH$_2$—N(R)—O-2'-, wherein each R is, independently, H, a protecting group, or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include, but are not limited to, (A) α-L-Methyleneoxy (4'-CH$_2$—O-2') BNA, (B) β-D-Methyleneoxy (4'-CH$_2$—O-2') BNA, (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl(methyleneoxy) (4'-CH(CH$_3$)—O-2') BNA, (G) methylene-thio (4'-CH$_2$—S-2') BNA, (H) methylene-amino (4'-CH2-N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

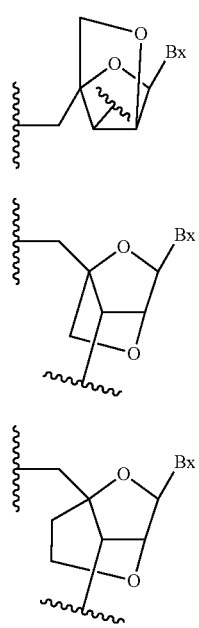

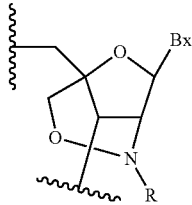

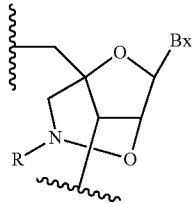

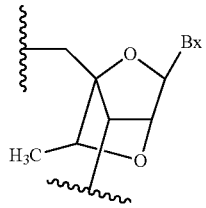

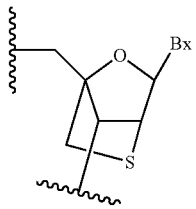

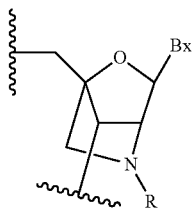

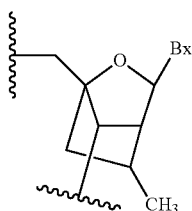

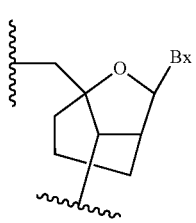

wherein Bx is the base moiety and R is, independently, H, a protecting group or $C_1$-$C_{12}$ alkyl.

In certain embodiments, bicyclic nucleoside having Formula I:

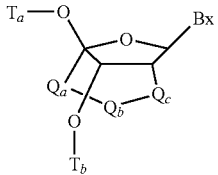

wherein:
Bx is a heterocyclic base moiety;
-$Q_a$-$Q_b$-$Q_c$- is —$CH_2$—N($R_c$)—$CH_2$—, —C(=O)—N($R_c$)—$CH_2$—, —$CH_2$—O—N($R_c$)—, —$CH_2$—N($R_c$)—O—, or —N($R_c$)—O—$CH_2$;
$R_c$ is $C_1$-$C_{12}$ alkyl or an amino protecting group; and
$T_a$ and $T_b$ are each, independently, H, a hydroxyl protecting group, a conjugate group, a reactive phosphorus group, a phosphorus moiety, or a covalent attachment to a support medium.

In certain embodiments, bicyclic nucleoside having Formula II:

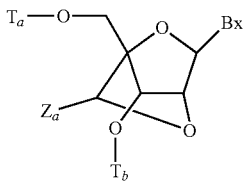

wherein:
Bx is a heterocyclic base moiety;
$T_a$ and $T_b$ are each, independently, H, a hydroxyl protecting group, a conjugate group, a reactive phosphorus group, a phosphorus moiety, or a covalent attachment to a support medium;
$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol, or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, OC(=X)$J_c$, and $NJ_eC$(=X)$NJ_cJ_d$, wherein each $J_c$, $J_d$, and $J_e$ is, independently, H, $C_1$-$C_6$ alkyl, or substituted $C_1$-$C_6$ alkyl and X is O or $NJ_c$.

In certain embodiments, bicyclic nucleoside having Formula III:

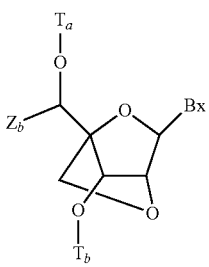

wherein:
Bx is a heterocyclic base moiety;
$T_a$ and $T_b$ are each, independently, H, a hydroxyl protecting group, a conjugate group, a reactive phosphorus group, a phosphorus moiety, or a covalent attachment to a support medium;
$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, or substituted acyl (C(=O)—).

In certain embodiments, bicyclic nucleoside having Formula IV:

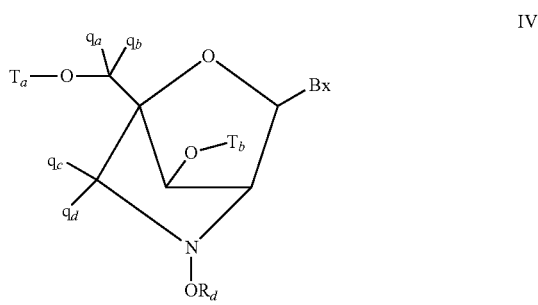

wherein:
Bx is a heterocyclic base moiety;
$T_a$ and $T_b$ are each, independently H, a hydroxyl protecting group, a conjugate group, a reactive phosphorus group, a phosphorus moiety, or a covalent attachment to a support medium;
$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl;
each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl, or substituted $C_1$-$C_6$ aminoalkyl;

In certain embodiments, bicyclic nucleoside having Formula V:

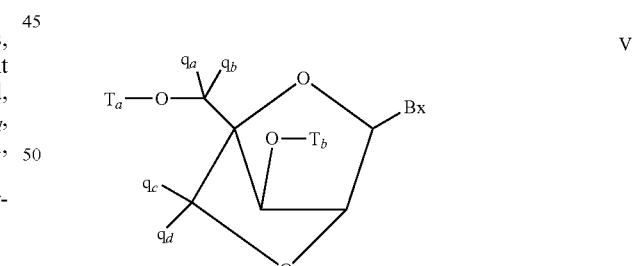

wherein:
Bx is a heterocyclic base moiety;
$T_a$ and $T_b$ are each, independently, H, a hydroxyl protecting group, a conjugate group, a reactive phosphorus group, a phosphorus moiety, or a covalent attachment to a support medium;
$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)

$NJ_jJ_k$, $C(=O)J_j$, $O—C(=O)NJ_jJ_k$, $N(H)C(=NH)NJ_jJ_k$, $N(H)C(=O)NJ_jJ_k$ or $N(H)C(=S)NJ_jJ_k$;

or $q_e$ and $q_f$ together are $=C(q_g)(q_h)$;

$q_g$ and $q_h$ are each, independently, H, halogen, $C_1$-$C_{12}$ alkyl, or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine, and uracil, along with their oligomerization, and nucleic acid recognition properties have been described (see, e.g., Koshkin et al., *Tetrahedron*, 1998, 54, 3607-3630). BNAs and preparation thereof are also described in WO 98/39352 and WO 99/14226.

Analogs of methyleneoxy (4'-$CH_2$—O-2') BNA, methyleneoxy (4'-$CH_2$—O-2') BNA, and 2'-thio-BNAs, have also been prepared (see, e.g., Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (see, e.g., Wengel et al., WO 99/14226). Furthermore, synthesis of 2'-amino-BNA, a novel comformationally restricted high-affinity oligonucleotide analog, has been described in the art (see, e.g., Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleoside having Formula VI:

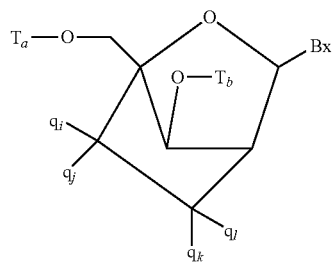

VI wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O—C(=O)NJ_jJ_k$, $N(H)C(=NH)NJ_jJ_k$, $N(H)C(=O)NJ_jJ_k$, or $N(H)C(=S)NJ_jJ_k$; and $q_i$ and $q_j$ or $q_i$ and $q_k$ together are $=C(q_g)(q_h)$, wherein $q_g$ and $q_h$ are each, independently, H, halogen, $C_1$-$C_{12}$ alkyl, or substituted $C_1$-$C_{12}$ alkyl.

One carbocyclic bicyclic nucleoside having a 4'-$(CH_2)_3$-2' bridge and the alkenyl analog, bridge 4'-CH=CH—$CH_2$-2', have been described (see, e.g., Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting the 2' carbon atom and the 4' carbon atom.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nONH_2$, $OCH_2C(=O)N(H)CH_3$, and $O(CH_2)_nON[(CH_2)_nCH_3]_2$, where n and m are from 1 to about 10. Other 2'-substituent groups can also be selected from: $C_1$-$C_{12}$ alkyl; substituted alkyl; alkenyl; alkynyl; alkaryl; aralkyl; O-alkaryl or O-aralkyl; SH; $SCH_3$; OCN; Cl; Br; CN; $CF_3$; $OCF_3$; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving pharmacokinetic properties; and a group for improving the pharmacodynamic properties of an antisense compound, and other substituents having similar properties. In certain embodiments, modified nucleosides comprise a 2'-MOE side chain (see, e.g., Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (see, e.g., Martin, P., *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), or those compounds having Formula X:

Formula X:

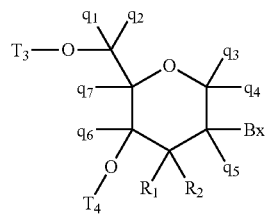

X wherein independently for each of said at least one tetrahydropyran nucleoside analog of Formula X:

Bx is a heterocyclic base moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S, or $NJ_1$, and each $J_1$, $J_2$, and $J_3$ is, independently, H or $C_1$-$C_6$ alkyl.

In certain embodiments, the modified THP nucleosides of Formula X are provided wherein $q_m$, $q_n$, $q_p$, $q_r$, $q_s$, $q_t$, and $q_u$ are each H. In certain embodiments, at least one of $q_m$, $q_n$, $q_p$, $q_r$, $q_s$, $q_t$, and $q_u$ is other than H. In certain embodiments, at least one of $q_m$, $q_n$, $q_p$, $q_r$, $q_s$, $q_t$ and $q_u$ is methyl. In certain embodiments, THP nucleosides of Formula X are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring and nucleosides with non-bridging 2'substituents, such as allyl, amino, azido, thio, O-allyl, O—$C_1$-$C_{10}$ alkyl, —$OCF_3$, O—$(CH_2)_2$—O—$CH_3$, 2'—$O(CH_2)_2SCH_3$, O—$(CH_2)_2$—O—$N(R_m)(R_n)$, or O—$CH_2$—C(=O)—$N(R_m)(R_n)$, where each $R_m$ and $R_n$ is, independently, H or substituted or unsubstituted $C_1$-$C_{10}$ alkyl. 2'-modified nucleosides may further comprise other modifications, for example, at other positions of the sugar and/or at the nucleobase.

As used herein, "2'-F" refers to a sugar comprising a fluoro group at the 2' position.

As used herein, "2'-OMe" or "2'-OCH$_3$" or "2'-O-methyl" each refers to a nucleoside comprising a sugar comprising an —OCH$_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry*, 2002, 10, 841-854).

Such ring systems can undergo various additional substitutions to enhance activity.

Methods for the preparations of modified sugars are well known to those skilled in the art.

In nucleotides having modified sugar moieties, the nucleobase moieties (natural, modified, or a combination thereof) are maintained for hybridization with an appropriate nucleic acid target.

In certain embodiments, antisense compounds comprise one or more nucleotides having modified sugar moieties. In certain embodiments, the modified sugar moiety is 2'-MOE. In certain embodiments, the 2'-MOE modified nucleotides are arranged in a gapmer motif. In certain embodiments, the modified sugar moiety is a cEt. In certain embodiments, the cEt modified nucleotides are arranged throughout the wings of a gapmer motif.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to a STAT3 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a STAT3 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Certain Antisense Compounds

In certain embodiments, antisense compounds useful for treating B-cell lymphoma at the doses and dosing regimens described above include any of the antisense oligonucleotides described in WO 2012/135736, which is incorporated by reference in its 5 entirety herein. Examples of antisense compounds described in WO 2012/135736 suitable for treating B-cell lymphoma include, but are not limited to, those described in Tables 1 & 2 below:

TABLE 1 cEt and MOE chimeric antisense oligonucleotides targeted to STAT3 (SEQ ID NO: 1)

| ISIS NO | Human Start Site | Human Stop Site | Sequence | Motif | Wing Chem | SEQ ID NO |
|---|---|---|---|---|---|---|
| 481355 | 322 | 337 | ACTGCCGCAGCTCCAT | 3-10-3 | cEt | 3 |
| 481597 | 731 | 744 | GAGATTCTCTACCA | 2-10-2 | cEt | 4 |
| 481374 | 788 | 803 | AGATCTTGCATGTCTC | 3-10-3 | cEt | 5 |
| 481390 | 1305 | 1320 | ATAATTCAACTCAGGG | 3-10-3 | cEt | 6 |
| 481420 | 1948 | 1963 | ACTTTTTCACAAGGTC | 3-10-3 | cEt | 7 |
| 481431 | 2206 | 2221 | CCATGATCTTATAGCC | 3-10-3 | cEt | 8 |
| 481453 | 2681 | 2696 | GATAGCAGAAGTAGGA | 3-10-3 | cEt | 9 |
| 481463 | 3001 | 3016 | CAAGGTTAAAAAGTGC | 3-10-3 | cEt | 10 |
| 481688 | 3002 | 3015 | AAGGTTAAAAAGTG | 2-10-2 | cEt | 11 |
| 481464 | 3016 | 3031 | CTATTTGGATGTCAGC | 3-10-3 | cEt | 12 |
| 481689 | 3017 | 3030 | TATTTGGATGTCAG | 2-10-2 | cEt | 13 |
| 481465 | 3032 | 3047 | TAGATAGTCCTATCTT | 3-10-3 | cEt | 14 |
| 481690 | 3033 | 3046 | AGATAGTCCTATCT | 2-10-2 | cEt | 15 |
| 481466 | 3047 | 3062 | AAGAAACCTAGGGCTT | 3-10-3 | cEt | 16 |
| 481691 | 3048 | 3061 | AGAAACCTAGGGCT | 2-10-2 | cEt | 17 |
| 481467 | 3097 | 3112 | GCTGATACAGTGTTTT | 3-10-3 | cEt | 18 |
| 481692 | 3098 | 3111 | CTGATACAGTGTTT | 2-10-2 | cEt | 19 |
| 481468 | 3112 | 3127 | ATACAGAAAGGCTATG | 3-10-3 | cEt | 20 |
| 481693 | 3113 | 3126 | TACAGAAAGGCTAT | 2-10-2 | cEt | 21 |
| 481469 | 3127 | 3142 | GCTTAAGTTTCTTAAA | 3-10-3 | cEt | 22 |
| 481694 | 3128 | 3141 | CTTAAGTTTCTTAA | 2-10-2 | cEt | 23 |
| 481470 | 3461 | 3476 | AGCACCAAGGAGGCTG | 3-10-3 | cEt | 24 |
| 481695 | 3462 | 3475 | GCACCAAGGAGGCT | 2-10-2 | cEt | 25 |
| 481471 | 3476 | 3491 | AAGCTGAATGCTTAAA | 3-10-3 | cEt | 26 |
| 481696 | 3477 | 3490 | AGCTGAATGCTTAA | 2-10-2 | cEt | 27 |
| 481472 | 3491 | 3506 | TTACCAGCCTGAAGGA | 3-10-3 | cEt | 28 |
| 481697 | 3492 | 3505 | TACCAGCCTGAAGG | 2-10-2 | cEt | 29 |
| 481473 | 3506 | 3521 | CAGGGATTATATAAAT | 3-10-3 | cEt | 30 |
| 481698 | 3507 | 3520 | AGGGATTATATAAA | 2-10-2 | cEt | 31 |
| 481474 | 3521 | 3536 | ACCTGAAGCCCGTTTC | 3-10-3 | cEt | 32 |
| 481699 | 3522 | 3535 | CCTGAAGCCCGTTT | 2-10-2 | cEt | 33 |
| 481475 | 3536 | 3551 | TGTCTTAAGGGTTTGA | 3-10-3 | cEt | 34 |
| 481700 | 3537 | 3550 | GTCTTAAGGGTTTG | 2-10-2 | cEt | 35 |

TABLE 1-continued cEt and MOE chimeric antisense oligonucleotides targeted to STAT3
(SEQ ID NO: 1)

| ISIS NO | Human Start Site | Human Stop Site | Sequence | Motif | Wing Chem | SEQ ID NO |
|---|---|---|---|---|---|---|
| 481476 | 3551 | 3566 | GGTTGCAGCTTCAGAT | 3-10-3 | cEt | 36 |
| 481701 | 3552 | 3565 | GTTGCAGCTTCAGA | 2-10-2 | cEt | 37 |
| 481477 | 3567 | 3582 | TCAACACCAAAGGCCA | 3-10-3 | cEt | 38 |
| 481702 | 3568 | 3581 | CAACACCAAAGGCC | 2-10-2 | cEt | 39 |
| 481478 | 3585 | 3600 | TCCTTAAACCTTCCTA | 3-10-3 | cEt | 40 |
| 481703 | 3586 | 3599 | CCTTAAACCTTCCT | 2-10-2 | cEt | 41 |
| 481479 | 3600 | 3615 | AAAATGCTTAGATTCT | 3-10-3 | cEt | 42 |
| 481704 | 3601 | 3614 | AAATGCTTAGATTC | 2-10-2 | cEt | 43 |
| 481480 | 3628 | 3643 | AAATAAGTCTATTTAT | 3-10-3 | cEt | 44 |
| 481705 | 3629 | 3642 | AATAAGTCTATTTA | 2-10-2 | cEt | 45 |
| 481481 | 3648 | 3663 | GGCCAATACATTACAA | 3-10-3 | cEt | 46 |
| 481706 | 3649 | 3662 | GCCAATACATTACA | 2-10-2 | cEt | 47 |
| 481482 | 3670 | 3685 | TGCCCAGCCTTACTCA | 3-10-3 | cEt | 48 |
| 481707 | 3671 | 3684 | GCCCAGCCTTACTC | 2-10-2 | cEt | 49 |
| 481483 | 3685 | 3700 | GTTGTAAGCACCCTCT | 3-10-3 | cEt | 50 |
| 481708 | 3686 | 3699 | TTGTAAGCACCCTC | 2-10-2 | cEt | 51 |
| 481484 | 3700 | 3715 | AGAAAGGGAGTCAAGG | 3-10-3 | cEt | 52 |
| 481709 | 3701 | 3714 | GAAAGGGAGTCAAG | 2-10-2 | cEt | 53 |
| 481485 | 3717 | 3732 | GCAGATCAAGTCCAGG | 3-10-3 | cEt | 54 |
| 481710 | 3718 | 3731 | CAGATCAAGTCCAG | 2-10-2 | cEt | 55 |
| 481486 | 3730 | 3745 | AGCCTCTGAAACAGCA | 3-10-3 | cEt | 56 |
| 481711 | 3731 | 3744 | GCCTCTGAAACAGC | 2-10-2 | cEt | 57 |
| 481487 | 3746 | 3761 | CCCACAGAAACAACCT | 3-10-3 | cEt | 58 |
| 481712 | 3747 | 3760 | CCACAGAAACAACC | 2-10-2 | cEt | 59 |
| 481488 | 3761 | 3776 | AGCCCTGATAAGGCAC | 3-10-3 | cEt | 60 |
| 481713 | 3762 | 3775 | GCCCTGATAAGGCA | 2-10-2 | cEt | 61 |
| 481489 | 3776 | 3791 | AATCAGAAGTATCCCA | 3-10-3 | cEt | 62 |
| 481714 | 3777 | 3790 | ATCAGAAGTATCCC | 2-10-2 | cEt | 63 |
| 481490 | 3833 | 3848 | GCCTCTAGCAGGATCA | 3-10-3 | cEt | 64 |
| 481715 | 3834 | 3847 | CCTCTAGCAGGATC | 2-10-2 | cEt | 65 |
| 481491 | 3848 | 3863 | CACGCAAGGAGACATG | 3-10-3 | cEt | 66 |
| 481716 | 3849 | 3862 | ACGCAAGGAGACAT | 2-10-2 | cEt | 67 |
| 481492 | 3863 | 3878 | TGAGGGACCTTTAGAC | 3-10-3 | cEt | 68 |
| 481717 | 3864 | 3877 | GAGGGACCTTTAGA | 2-10-2 | cEt | 69 |
| 481493 | 3886 | 3901 | CAGGATTCCTAAAACA | 3-10-3 | cEt | 70 |
| 481718 | 3887 | 3900 | AGGATTCCTAAAAC | 2-10-2 | cEt | 71 |

TABLE 1-continued cEt and MOE chimeric antisense oligonucleotides targeted to STAT3
(SEQ ID NO: 1)

| ISIS NO | Human Start Site | Human Stop Site | Sequence | Motif | Wing Chem | SEQ ID NO |
|---|---|---|---|---|---|---|
| 481494 | 3901 | 3916 | ATGAGGTCCTGAGACC | 3-10-3 | cEt | 72 |
| 481719 | 3902 | 3915 | TGAGGTCCTGAGAC | 2-10-2 | cEt | 73 |
| 481495 | 3940 | 3955 | CATCATGTCCAACCTG | 3-10-3 | cEt | 74 |
| 481720 | 3941 | 3954 | ATCATGTCCAACCT | 2-10-2 | cEt | 75 |
| 481496 | 3955 | 3970 | GGGCCCCATAGTGTGC | 3-10-3 | cEt | 76 |
| 481721 | 3956 | 3969 | GGCCCCATAGTGTG | 2-10-2 | cEt | 77 |
| 481497 | 3977 | 3992 | AGCTCAACCAGACACG | 3-10-3 | cEt | 78 |
| 481722 | 3978 | 3991 | GCTCAACCAGACAC | 2-10-2 | cEt | 79 |
| 481498 | 3992 | 4007 | GAACCATATTCCCTGA | 3-10-3 | cEt | 80 |
| 481723 | 3993 | 4006 | AACCATATTCCCTG | 2-10-2 | cEt | 81 |
| 481499 | 4007 | 4022 | CAAGAAACTGGCTAAG | 3-10-3 | cEt | 82 |
| 481724 | 4008 | 4021 | AAGAAACTGGCTAA | 2-10-2 | cEt | 83 |
| 481500 | 4022 | 4037 | GCCACTGGATATCACC | 3-10-3 | cEt | 84 |
| 481501 | 4048 | 4063 | AACTGAATGAAGACGC | 3-10-3 | cEt | 85 |
| 481523 | 4489 | 4504 | GCTTATTATGTACTGA | 3-10-3 | cEt | 86 |
| 481748 | 4490 | 4503 | CTTATTATGTACTG | 2-10-2 | cEt | 87 |
| 481524 | 4530 | 4545 | GCCCAAGTCTCACCTT | 3-10-3 | cEt | 88 |
| 481749 | 4531 | 4544 | CCCAAGTCTCACCT | 2-10-2 | cEt | 89 |
| 481525 | 4541 | 4556 | CCCAATGGTAAGCCCA | 3-10-3 | cEt | 90 |
| 481750 | 4542 | 4555 | CCAATGGTAAGCCC | 2-10-2 | cEt | 91 |
| 481526 | 4543 | 4558 | AACCCAATGGTAAGCC | 3-10-3 | cEt | 92 |
| 481751 | 4544 | 4557 | ACCCAATGGTAAGC | 2-10-2 | cEt | 93 |
| 481527 | 4560 | 4575 | TAGGTCCCTATGATTT | 3-10-3 | cEt | 94 |
| 481752 | 4561 | 4574 | AGGTCCCTATGATT | 2-10-2 | cEt | 95 |
| 481528 | 4579 | 4594 | AAGCCCTGAACCCTCG | 3-10-3 | cEt | 96 |
| 481753 | 4580 | 4593 | AGCCCTGAACCCTC | 2-10-2 | cEt | 97 |
| 481529 | 4615 | 4630 | CCTAAGGCCATGAACT | 3-10-3 | cEt | 98 |
| 481754 | 4616 | 4629 | CTAAGGCCATGAAC | 2-10-2 | cEt | 99 |
| 481530 | 4630 | 4645 | ACCAGATACATGCTAC | 3-10-3 | cEt | 100 |
| 481755 | 4631 | 4644 | CCAGATACATGCTA | 2-10-2 | cEt | 101 |
| 481531 | 4646 | 4661 | TACAATCAGAGTTAAG | 3-10-3 | cEt | 102 |
| 481756 | 4647 | 4660 | ACAATCAGAGTTAA | 2-10-2 | cEt | 103 |
| 481532 | 4664 | 4679 | TCCTCTCAGAACTTTT | 3-10-3 | cEt | 104 |
| 481757 | 4665 | 4678 | CCTCTCAGAACTTT | 2-10-2 | cEt | 105 |
| 481533 | 4666 | 4681 | GCTCCTCTCAGAACTT | 3-10-3 | cEt | 106 |
| 481758 | 4667 | 4680 | CTCCTCTCAGAACT | 2-10-2 | cEt | 107 |
| 481534 | 4693 | 4708 | TTCTTTAATGGGCCAC | 3-10-3 | cEt | 108 |

TABLE 1-continued cEt and MOE chimeric antisense oligonucleotides targeted to STAT3 (SEQ ID NO: 1)

| ISIS NO | Human Start Site | Human Stop Site | Sequence | Motif | Wing Chem | SEQ ID NO |
|---|---|---|---|---|---|---|
| 481759 | 4694 | 4707 | TCTTTAATGGGCCA | 2-10-2 | cEt | 109 |
| 481535 | 4767 | 4782 | ACGGGATTCCCTCGGC | 3-10-3 | cEt | 110 |
| 481760 | 4768 | 4781 | CGGGATTCCCTCGG | 2-10-2 | cEt | 111 |
| 481536 | 4782 | 4797 | GTAGGTAAGCAACCCA | 3-10-3 | cEt | 112 |
| 481761 | 4783 | 4796 | TAGGTAAGCAACCC | 2-10-2 | cEt | 113 |
| 481537 | 4830 | 4845 | GAATTTGAATGCAGTG | 3-10-3 | cEt | 114 |
| 481762 | 4831 | 4844 | AATTTGAATGCAGT | 2-10-2 | cEt | 115 |
| 481538 | 4844 | 4859 | TGAAGTACACATTGGA | 3-10-3 | cEt | 116 |
| 481763 | 4845 | 4858 | GAAGTACACATTGG | 2-10-2 | cEt | 117 |
| 481539 | 4860 | 4875 | ATAAATTTTACACTA | 3-10-3 | cEt | 118 |
| 481764 | 4861 | 4874 | TAAATTTTACACT | 2-10-2 | cEt | 119 |
| 481765 | 4869 | 4882 | CAATAATATAAATT | 2-10-2 | cEt | 120 |
| 481541 | 4934 | 4949 | CTGGAAGTTAAAGTAG | 3-10-3 | cEt | 121 |
| 481766 | 4935 | 4948 | TGGAAGTTAAAGTA | 2-10-2 | cEt | 122 |

TABLE 2

Chimeric antisense oligonucleotides targeted to STAT3 (SEQ ID NO: 2)

| Human Start Site | Human Stop Site | ISIS No | Sequence | Chemistry | SEQ ID NO |
|---|---|---|---|---|---|
| 5701 | 5716 | GTACTCTTTCAGTGGT | 529962 | e-e-e-d(10)-k-k-k | 123 |
| 74784 | 74799 | ATGCTTAGATTCTCCT | 529979 | k-k-k-d(10)-e-e-e | 124 |
| 74905 | 74920 | AGCAGATCAAGTCCAG | 529982 | k-k-k-d(10)-e-e-e | 125 |
| 75423 | 75438 | AGGTGTTCCCATACGC | 529983 | k-k-k-d(10)-e-e-e | 126 |
| 75424 | 75439 | TAGGTGTTCCCATACG | 529984 | k-k-k-d(10)-e-e-e | 127 |
| 5701 | 5716 | GTACTCTTTCAGTGGT | 529999 | k-k-k-d(10)-e-e-e | 123 |
| 9878 | 9893 | GGTTCCTCCTGTTGGC | 530006 | k-k-k-d(10)-e-e-e | 128 |
| 12361 | 12376 | GGTTCCTCCTGTTGGC | 530006 | k-k-k-d(10)-e-e-e | 128 |
| 74783 | 74799 | ATGCTTAGATTCTCCTT | 530020 | e-e-k-d(10)-k-e-k-e | 129 |

Certain Combination Therapies

In certain embodiments, one or more pharmaceutical compositions provided herein are co-administered with one or more other pharmaceutical agents. In certain embodiments, such one or more other pharmaceutical agents are designed to treat the same disease, disorder, or condition as the one or more pharmaceutical compositions provided herein. In certain embodiments, such one or more other pharmaceutical agents are designed to treat a different disease, disorder, or condition as the one or more pharmaceutical compositions provided herein. In certain embodiments, such one or more other pharmaceutical agents are designed to treat an undesired side effect of one or more pharmaceutical compositions provided herein. In certain embodiments, one or more pharmaceutical compositions provided herein are co-administered with another pharmaceutical agent to treat an undesired effect of that other pharmaceutical agent. In certain embodiments, one or more pharmaceutical compositions provided herein are co-administered with another pharmaceutical agent to produce a combinational effect. In certain embodiments, one or more pharmaceutical compositions provided herein are co-administered with another pharmaceutical agent to produce a synergistic effect.

In certain embodiments, one or more pharmaceutical compositions provided herein and one or more other pharmaceutical agents are administered at the same time. In certain embodiments, one or more pharmaceutical compositions provided herein and one or more other pharmaceutical agents are administered at different times. In certain embodiments, one or more pharmaceutical compositions provided herein and one or more other pharmaceutical agents are prepared together in a single formulation. In certain embodiments, one or more pharmaceutical compositions provided herein and one or more other pharmaceutical agents are prepared separately. In certain embodiments, one or more other pharmaceutical agents include all-trans retinoic acid, azacitidine, azathioprine, bleomycin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, mechlorethamine, mercaptopurine, methotrexate, mitoxantrone, oxaliplatin, paclitaxel, pemetrexed, teniposide, tioguanine, valrubicin, vinblastine, vincristine, vindesine, or vinorelbine. In certain embodiments, one or more other pharmaceutical agents include a combination of cyclophosphamide, hydroxydanuorubicin, oncovin (vincristine), prednisone or prednisolone (CHOP). In certain embodiments, one or more other pharmaceutical agents include a combination of rituximab and CHOP (R-CHOP). In certain embodiments, one or more other pharmaceutical agents include another antisense oligonucleotide. In certain embodiments, another antisense oligonucleotide is a second STAT3 antisense oligonucleotide.

In certain embodiments, one or more other pharmaceutical agents include molecular targeted therapies. In certain embodiments, the molecular targeted therapy is an EGFR inhibitor, a mTOR inhibitor, a HER2 inhibitor, or a VEGF/VEGFR inhibitor. In certain embodiments, EGFR inhibitors include gefitinib, erlotinib, lapatinib, cetuximab, panitumumbo. In certain embodiments, mTOR inhibitors include everolimus and temsirolimus. In certain embodiments, HER2 inhibitors include trastuzumab and lapatinib. In certain embodiments, VEGF/VEGFR inhibitors include pazopanib, bevacizumab, sunitinib, and sorafenib.

In certain embodiments, one more pharmaceutical compositions provided herein are administered with radiation therapy. In certain embodiments, one or more pharmaceutical compositions are administered at the same time as radiation therapy. In certain embodiments, one or more pharmaceutical compositions are administered before radiation therapy. In certain embodiments, one or more pharmaceutical compositions are administered after radiation therapy. In certain embodiments, one or more pharmaceutical compositions are administered at various time points throughout a radiation therapy regimen.

In certain embodiments, radiation therapy is useful for inhibiting tumor growth. In certain embodiments, radiation therapy is useful for increasing overall survival. In certain embodiments, radiation therapy used in conjunction with administration of one or more pharmaceuticals provided herein is advantageous over using either therapy alone because both radiation therapy and administration with one or more pharmaceuticals can be limited to achieve effective antiproliferative response with limited toxicity.

In certain embodiments, a physician designs a therapy regimen including both radiation therapy and administration of one more pharmaceutical compositions provided herein. In certain embodiments, a physician designs a therapy regimen including radiation therapy, administration of one or more pharmaceutical compositions provided herein, and administration of one or more other chemotherapeutic agents.

EXAMPLES

Non-limiting Disclosure and Incorporation by Reference

While certain compounds, compositions and methods described herein have been described with specificity in accordance with certain embodiments, the following examples serve only to illustrate certain embodiments described herein and are not intended to limit the same. Each of the references recited in the present application is incorporated herein by reference in its entirety.

Example 1

Phase 1, Open-label, Study for Treating a Patient Having Advanced B Cell Lymphoma with a STAT3 Antisense Oligonucleotide The effect of intravenous infusion of the STAT3 antisense oligonucleotide, ISIS 481464, in patients with advanced B cell lymphomas was studied. Patients with diffuse large B-cell lymphomas (DLBCL) were recruited for this study.

The criteria for patient inclusion with respect to their tumor status was that the tumors should be relapsed or refractory to at least one prior anti-cancer systemic therapy, and/or for which no standard therapy exists; that their disease should be measurable or evaluable, according to RECIST version 1.1 for solid tumors, or according to the International Workshop Response Criteria for Non-Hodgkin's Lymphoma for NHL tumors (Cheson, B. D. et al., J. Clin. Oncol. 1999, 17: 1244; Cheson, B. D. et al., J. Clin. Oncol. 2007, 25(5):579-86), or according to appropriate criteria for other advanced cancers. RECIST (Response Evaluation Criteria in Solid Tumors) is an internationally accepted set of guidelines used in clinical trials for solid tumor disease.

One patient fitting the criteria above is a 63 year old female with DLBCL designated herein as Patient #1001. Prior to commencing therapy, Patient #1001 showed multiple areas of hypermetabolic adenopathy, both above and below the diaphragm, including the supraclavicular, left paratracheal, right internal mammary, pericardial, left intramammary, pre-hepatic, retroperitoneal, and mesenteric regions. In addition, the patient suffered from fatigue, nausea, night sweats, shortness of breath on exertion, and peripheral neuropathy. The patient also noted 5-6 days of right-sided abdominal fullness and associated pain. Patient therapy was commenced with a treatment period comprising administration during a first phase of 3 loading doses of ISIS 481464: a 3-hr intravenous infusion of 2 mg/kg ideal body weight of ISIS 481464 administered on days 1, 3, and 5 of cycle 0. The ideal body weight was determined using the Devine formula (Pai, M. P. and Paloucek, F. P. Ann. Pharmacol. 2000. 34: 1066-1069): for men (in kg)=50+2.3 kg/inch over 5 feet; for women (in kg)=45.5+2.3 kg/inch over 5 feet. Treatment was then continued in a second phase by once-weekly administrations (Cycle 1 and beyond) of 2 mg/kg ideal body weight of ISIS 481464 until disease progression, unacceptable toxicity, or patient discontinuation for any other reason occurred. Disease assessments were performed at the end of even cycles.

Tumor lesions were evaluated on each even-numbered cycle, starting with Cycle 2, day 15, by positron emission tomography (PET) scan. According to RECIST guidelines, a complete tumor response is achieved when all target lesions have disappeared. Partial response is achieved when the sum of the diameters of all tumor lesions is reduced at least 30% compared to the sum of the tumor lesion diameters at pre-dose. The sum of the lesion diameters, if any, was calculated, per RECIST guidelines (Eisenhauer, E. A. et al., Eur. J. Cancer 45: 228-247, 2009).

After 28 days of treatment with ISIS 481464, the patient reported reduced fatigue and night sweats, and was tolerating the treatment well.

After 49 days of treatment with ISIS 481464, a PET scan was performed and revealed a 55% reduction in tumor size. Tumors were reduced in all compartments, but most notably, in the supraclavicular, paratracheal, pericardial, and mesenteric regions.

After 91 days of treatment with ISIS 481464, Patient #1001 had a second PET scan and the partial response observed in the first scan was found to be maintained at a 55% reduction in tumor size.

After 133 days of treatment with ISIS 481464, Patient #1001 had a third PET scan and the partial response was found to be maintained at a 55% reduction in tumor size.

After 162 days of treatment with ISIS 481464, further treatment was paused for a month during which Patient #1001 had a fourth PET scan, and the partial response was maintained at a 55% reduction in tumor size. Patient #1001 is scheduled for further scans.

Example 2

Phase 1, Open-label, Study for Treating a Patient Having Advanced/Metastatic Hepatocellular Carcinoma with a STAT3 Antisense Oligonucleotide The effect of intravenous infusion of the STAT3 antisense oligonucleotide, ISIS 481464, in patients with advanced/metastatic hepatocellular carcinoma is being studied in an on-going clinical trial.

In the study described in this protocol, AZD9150 will be administered to patients with advanced/metastatic hepatocellular carcinoma at a starting dose of 1 mg/kg intravenously 3× during week 1 followed by 1× weekly and dose intensity will be escalated or de-escalated in subsequent cohorts through modification of unit dose administered and/or interval of administration to determine a maximum tolerated dose and recommended phase II dose in patients with advanced/metastatic hepatocellular carcinoma (HCC).

Following the dose escalation phase of the study additional patients will be enrolled to a dose expansion phase to explore further the safety, tolerability, pharmacokinetics and biological activity at selected dose(s)/schedules. Patients included in the study are relapsed, refractory, intolerant or unlikely to benefit from first-line systemic therapy (sorafenib).

To date, the 1 mg/kg and 1.5 mg/kg cohorts have completed. From the 1 mg/kg cohort 4 patients remain on study with stable disease in excess of 3 months. Stable disease has also been seen in 1.5 mg/kg cohort. These patients and future patients will be monitored further for clinical activity as the trial progresses.

The invention claimed is:

1. A method of treating cancer comprising administering to a subject having cancer a pharmaceutical composition comprising a sodium salt of a single stranded compound comprising a modified oligonucleotide consisting of 12 to 30 linked nucleosides having a nucleobase sequence comprising at least 12 contiguous nucleobases of the nucleobase sequence of SEQ ID NO: 12, wherein administering the antisense compound comprises:
 a loading phase comprising a total weekly dose in the range of about 100-750 mg for the first 1-10 weeks, and
 a maintenance phase comprising a total weekly dose in the range of 100-250 mg for at least 1 week after the loading phase.

2. The method of claim 1, wherein the dose is administered for at least 1-52 weeks.

3. The method of claim 1, wherein the dose is administered to the subject 1-6 times per week.

4. The method of claim 1, wherein the dose is administered 1-6 times during the first week and 1 time each subsequent week.

5. The method of claim 1, wherein the loading phase is 1 week.

6. The method of claim 1, wherein the total weekly dose of the antisense compound in the loading phase is an amount of any of about 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, or 750 mg.

7. The method of claim 6, wherein the total weekly dose of the antisense compound in the loading phase is an amount of about 600 mg.

8. The method of claim 1, wherein the total weekly dose of the antisense compound in the maintenance phase is an amount of any of about 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, or 250 mg.

9. The method of claim 8, wherein the total weekly dose of the antisense compound in the maintenance phase is about 200 mg.

10. The method of claim 1, wherein the cancer is B-cell lymphoma or hepatocellular carcinoma (HCC).

11. The method of claim 10, wherein the B-cell lymphoma is a non-Hodgkin's B-cell lymphoma.

12. The method of claim 11, wherein the non-Hodgkin's B-cell lymphoma is selected from the group consisting of: diffuse large B cell lymphoma (DLBCL), follicular lymphoma, mucosa-associated lymphatic tissue lymphoma (MALT), small cell lymphocytic lymphoma, chronic lymphocytic leukemia, mantle cell lymphoma (MCL), Burkitt lymphoma, mediastinal large B cell lymphoma, Waldenström macroglobulinemia, nodal marginal zone B cell lymphoma (NMZL), splenic marginal zone lymphoma (SMZL), intravascular large B-cell lymphoma, primary effusion lymphoma, and lymphomatoid granulomatosis.

13. The method of claim 12, wherein the non-Hodgkin's B-cell lymphoma is diffuse large B cell lymphoma (DLBCL).

14. The method of claim 1, wherein the nucleobase sequence of the modified oligonucleotide comprises the sequence of SEQ ID NO: 12.

15. The method of claim 1, wherein the nucleobase sequence of the modified oligonucleotide consists of the sequence of SEQ ID NO: 12.

16. The method of claim 1, wherein the nucleobase sequence of the modified oligonucleotide consists of the sequence of SEQ ID NO: 12, and comprises:
- a gap segment consisting often linked deoxynucleosides;
- a 5' wing segment consisting of 3 linked nucleosides; and
- a 3' wing segment consisting of 3 linked nucleosides;
- wherein the gap segment is positioned between the 5' wing segment and the 3' wing segment; wherein each nucleoside of each wing segment comprises a constrained ethyl nucleoside; wherein each internucleoside linkage of the modified oligonucleotide is a phosphorothioate linkage; and wherein each cytosine of the modified oligonucleotide is a 5-methylcytosine.

17. A method of treating cancer comprising administering to a subject having cancer a pharmaceutical composition comprising a potassium salt of a single stranded compound comprising a modified oligonucleotide consisting of 12 to 30 linked nucleosides having a nucleobase sequence comprising at least 12 contiguous nucleobases of the nucleobase sequence of SEQ ID NO: 12, wherein administering the antisense compound comprises:
- a loading phase comprising a total weekly dose in the range of about 100-750 mg for the first 1-10 weeks, and
- a maintenance phase comprising a total weekly dose in the range of 100-250 mg for at least 1 week after the loading phase.

18. The method of claim 17, wherein the dose is administered for at least 1-52 weeks.

19. The method of claim 17, wherein the dose is administered to the subject 1-6 times per week.

20. The method of claim 17, wherein the dose is administered 1-6 times during the first week and 1 time each subsequent week.

21. The method of claim 17, wherein the loading phase is 1 week.

22. The method of claim 17, wherein the total weekly dose of the antisense compound in the loading phase is an amount of any of about 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, or 750 mg.

23. The method of claim 22, wherein the total weekly dose of the antisense compound in the loading phase is an amount of about 600 mg.

24. The method of claim 17, wherein the total weekly dose of the antisense compound in the maintenance phase is an amount of any of about 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, or 250 mg.

25. The method of claim 24, wherein the total weekly dose of the antisense compound in the maintenance phase is an amount of about 200 mg.

26. The method of claim 17, wherein the cancer is B-cell lymphoma or hepatocellular carcinoma (HCC).

27. The method of claim 26, wherein the B-cell lymphoma is a non-Hodgkin's B-cell lymphoma.

28. The method of claim 27, wherein the non-Hodgkin's B-cell lymphoma is selected from the group consisting of: diffuse large B cell lymphoma (DLBCL), follicular lymphoma, mucosa-associated lymphatic tissue lymphoma (MALT), small cell lymphocytic lymphoma, chronic lymphocytic leukemia, mantle cell lymphoma (MCL), Burkitt lymphoma, mediastinal large B cell lymphoma, Waldenström macroglobulinemia, nodal marginal zone B cell lymphoma (NMZL), splenic marginal zone lymphoma (SMZL), intravascular large B-cell lymphoma, primary effusion lymphoma, and lymphomatoid granulomatosis.

29. The method of claim 28, wherein the non-Hodgkin's B-cell lymphoma is diffuse large B cell lymphoma (DLBCL).

30. The method of claim 17, wherein the nucleobase sequence of the modified oligonucleotide comprises the sequence of SEQ ID NO: 12.

31. The method of claim 17, wherein the nucleobase sequence of the modified oligonucleotide consists of the sequence of SEQ ID NO: 12.

32. The method of claim 17, wherein the nucleobase sequence of the modified oligonucleotide consists of the sequence of SEQ ID NO: 12, and comprises:
- a gap segment consisting often linked deoxynucleosides;
- a 5' wing segment consisting of 3 linked nucleosides; and
- a 3' wing segment consisting of 3 linked nucleosides;
- wherein the gap segment is positioned between the 5' wing segment and the 3' wing segment; wherein each nucleoside of each wing segment comprises a constrained ethyl nucleoside; wherein each internucleoside linkage of the modified oligonucleotide is a phosphorothioate linkage; and wherein each cytosine of the modified oligonucleotide is a 5-methylcytosine.

* * * * *